(12) United States Patent
Deng et al.

(10) Patent No.: US 12,157,755 B2
(45) Date of Patent: Dec. 3, 2024

(54) CD73 INHIBITOR, PREPARATION METHOD THEREFOR AND APPLICATION THEREOF

(71) Applicant: Abbisko Therapeutics Co., Ltd., Shanghai (CN)

(72) Inventors: Haibing Deng, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

(*) Notice: Subject to any disclaimer, the term of this patent is extended or adjusted under 35 U.S.C. 154(b) by 423 days.

(21) Appl. No.: 17/438,770

(22) PCT Filed: Apr. 27, 2020

(86) PCT No.: PCT/CN2020/087259
§ 371 (c)(1),
(2) Date: Sep. 13, 2021

(87) PCT Pub. No.: WO2020/221209
PCT Pub. Date: Nov. 5, 2020

(65) Prior Publication Data
US 2022/0162253 A1    May 26, 2022

(30) Foreign Application Priority Data

| Apr. 28, 2019 | (CN) | 201910350348.6 |
| Jun. 13, 2019 | (CN) | 201910510367.0 |
| Dec. 27, 2019 | (CN) | 201911375322.3 |

(51) Int. Cl.
*C07H 19/207* (2006.01)

(52) U.S. Cl.
CPC .............................. *C07H 19/207* (2013.01)

(58) Field of Classification Search
None
See application file for complete search history.

(56) References Cited

FOREIGN PATENT DOCUMENTS

| WO | 2017120508 A1 | 7/2017 | |
| WO | 2018067424 A1 | 4/2018 | |
| WO | 2018183635 A1 | 10/2018 | |
| WO | 2018208727 A1 | 11/2018 | |
| WO | WO-2018208980 A1 * | 11/2018 | ........... A61K 31/675 |
| WO | 2019129059 A1 | 7/2019 | |
| WO | 2019173682 A1 | 9/2019 | |
| WO | 2019232319 A1 | 12/2019 | |
| WO | 2019246403 A1 | 12/2019 | |
| WO | 2020051686 A1 | 3/2020 | |
| WO | 2020185859 A1 | 9/2020 | |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al., "Modern Pharmaceutics, 3ed.", Marcel Dekker, New York, 1996, p. 596 (Year: 1996).*
Bhattarai et al., "α,ß-Methylene-ADP (AOPCP) Derivatives and Analogues: Development of Potent and Selective ecto-5'-Nucleotidase (CD73) Inhibitors", J. Med. Chem., vol. 58, No. 15, pp. 6248-6263 (2015).
Examination Report issued Oct. 10, 2022 in Australia Application No. 2020264642.
Office Action issued Oct. 4, 2022 in Japan Application No. 2021-556880, with English translation.
Int'l Search Report issued Jul. 28, 2020 in Int'l Application No. PCT/CN2020/087259.
Office Action issued Jul. 6, 2021 in TW Application No. 11020529680.
Patani et al., "Bioisosterism: A Rational Approach in Drug Design," Chemical Reviews, vol. 96, No. 8, pp. 3147-3176 (1996).
Examination Report issued Dec. 13, 2021 in IN Application No. 202137036357.

* cited by examiner

Primary Examiner — Traviss C McIntosh, III
(74) Attorney, Agent, or Firm — Panitch Schwarze Belisario & Nadel LLP

(57) ABSTRACT

A CD73 inhibitor having the structure represented by formula (I), a preparation method therefor and an application thereof are provided. The series of compounds can be widely applied in the preparation of drugs for treating cancers or tumors that are at least partially mediated by CD73, autoimmune diseases and disorders and metabolic diseases, in particular drugs for treating melanoma, colon cancer, pancreatic cancer, breast cancer, prostate cancer, lung cancer, leukemia, brain tumor, lymphoma, ovarian cancer and Kaposi's sarcoma. A new generation of CD73 inhibitor drugs is expected to be developed.

(I)

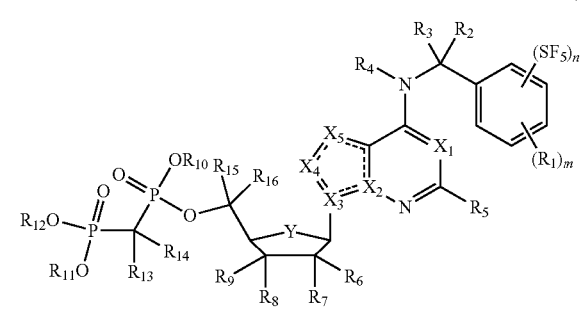

8 Claims, No Drawings

CD73 INHIBITOR, PREPARATION METHOD THEREFOR AND APPLICATION THEREOF

CROSS-REFERENCE TO RELATED APPLICATIONS

This application is a Section 371 of International Application No. PCT/CN2020/087259, filed Apr. 27, 2020, which was published in the Chinese language on Nov. 5, 2020, under International Publication No. WO 2020/221209 A1, which claims priority under 35 U.S.C. § 119(b) to Chinese Application No. 201910350348.6, filed Apr. 28, 2019, Chinese Application No. 201910510367.0, filed Jun. 13, 2019, and Chinese Application No. 201911375322.3, filed Dec. 27, 2019, the disclosure of each of which is incorporated herein by reference in their entireties.

TECHNICAL FIELD

The present invention belongs to the field of pharmaceutical synthesis, and in particular, relates to a CD73 inhibitor, a preparation method therefor and application thereof.

BACKGROUND

CD73, also known as Ecto-5'-nucleotidase (eNT), is a 70-kDa protein. It is expressed on endothelial cells and certain leukocytes under normal circumstances. Anchored to the cell membrane surface via a glycosylphosphatidylinositol (GPI) linkage, it plays a role in the metabolic regulation of adenosine triphosphate (ATP) together with CD39, which is also known as ecto-nucleoside triphosphate diphosphohydrolase (NTPDase)-1, catalyzes the hydrolysis of ATP to generate adenosine monophosphate (AMP) and only little adenosine diphosphate (ADP) while CD73 plays a major role in catalyzing the conversion of extracellular monophosphate (such as 5'AMP) into their corresponding nucleosides (such as adenosine).

The nucleosides produced by CD73, particularly adenosine, are considered to be endogenous modulator of diverse physiological functions including the cardiovascular system central nervous system, the respiratory system, the kidney, the fat cells, the platelets and the immune system. In the immune system, extracellular adenosine acts on a variety of immune cells and mediate anti-inflammatory responses. In a variety of tissues, adenosine can also promote fibrosis.

The expression of CD73 has been found in many types of cancer cells, including leukemia, bladder cancer, glioma, glioblastoma, ovarian cancer, melanoma, prostate cancer, thyroid cancer, esophageal cancer and breast cancer. Meanwhile, the expression of CD73 has been also found on the surface of immunosuppressive cells (including regulatory T cells (Treg) and myeloid suppressor cells (MDSC). The high expression of CD73 has also been found to be associated with angiogenesis, invasiveness, resistance to chemotherapy, tumor metastasis, and shorter survival time of cancer patients of a variety of tumors including breast cancer and melanoma.

Mechanism-based studies have shown that malignant tumor cells may release a large amount of ATP under the action of chemotherapy and other stresses, and the ATP may be quickly converted into adenosine and accumulated in a tumor microenvironment. The release of extracellular ATP due to cell death or intracellular stresses may activate immune responses, but adenosine, the metabolite of ATP, is immunosuppressive. Most importantly, adenosine in tumors can inhibit the infiltrating effector T lymphocytes by activating adenosine receptors (such as A2A), thereby promoting the tumor progression. Therefore, the accumulation of extracellular adenosine in tumor tissues is an important mechanism of tumor immune escape.

Reducing the expression of CD73 with interfering RNA or by overexpressing CD73 in tumor cells can modulate tumor growth and migration; CD73-knockout mice are less prone to organ transplant rejection and spontaneous tumorigenesis; and genetic deletion of A2A receptors may induce T-cell-dependent tumor rejection. In a mouse model, treatment with an antibody that binds to mouse CD73 can inhibit the tumor growth and metastasis of breast cancer.

Hence, targeting CD73 represents a potential therapeutic strategy that can enhances anti-tumor efficacy and provide a new therapeutic strategy for inhibiting tumor progression. Moreover, targeting CD73 can also be used to treat other adenosine-mediated diseases, such as enhancement of immune responses, immune effect and inflammatory responses, and treatment of diseases including neurological disorders, neurodegenerative diseases, and central nervous system (CNS) diseases, such as depression, Parkinson's disease, sleep disorder, fibrosis, and other immuno-inflammatory diseases.

Therefore, the development of CD73-targeted drug candidates will meet the needs of target therapy in the treatment of cancer and other associated diseases thereof, and bring the benefit of great safety and specificity.

SUMMARY

After an extensive and intensive research, the inventor of the present invention developed a CD73 inhibitor of formula (I), and a preparation method therefor and a use thereof. The series of compounds of the present invention have a strong inhibitory effect on the enzymatic activity of CD73, can be widely applied to the preparation of drug for treating cancers or tumors, immune-related diseases and disorders or metabolic diseases, which are at least partially mediated by CD73, particularly for treating melanoma, colon cancer, pancreatic cancer, breast cancer, prostate cancer, lung cancer, leukemia, brain tumor, lymphoma, ovarian cancer and Kaposi's sarcoma, and show promise for the development of a new generation of CD73 inhibitor drug. On such basis, the present invention has been completed.

The first aspect of the present invention provides a compound of formula (I), a stereoisomer, prodrug or pharmaceutically acceptable salt thereof:

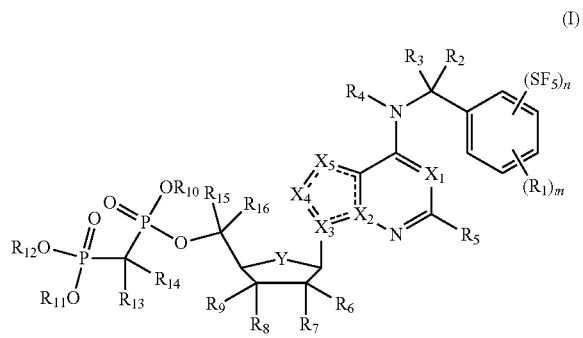

wherein, "═" is double bond or single bond;
$X_1$ is N or $CR_{17}$;
$X_2$ and $X_3$ are each independently N or C;
$X_4$ and $X_5$ are each independently N or $CR_{18}$;

Y is $CH_2$, NH, O or S;

m is 0, 1, 2 or 3; n is 0, 1, 2 or 3, provided that m+n≤5;

$R_1$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, $-C_{0-8}-SF_5$, $-C_{0-8}-S(O)_rR_{19}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$, or, when m≥2, two of $R_1$ together with the moiety directly attached thereto form 4-10 membered cycloalkyl, 4-10 membered aryl, 4-10 membered heterocyclyl or 4-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{20}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$;

$R_2$ and $R_3$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-C(O)NR_{22}R_{23}$ and $-C_{0-8}-NR_{22}R_{23}$, or, $R_2$ and $R_3$, together with the carbon atom directly attached thereto, form 3-10 membered cycloalkyl or 3-10 membered heterocyclyl, or, one of $R_2$ and $R_3$, together with $R_1$ and the group directly attached thereto, form 4-10 membered cycloalkyl or 4-10 membered heterocyclyl, and the other one is selected from the group consisting of hydrogen, deuterium, halogen and $C_{1-10}$alkyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$;

$R_4$ is selected from the group consisting of hydrogen, deuterium, $C_{1-10}$ alkyl, $C_{2-10}$ alkenyl, $C_{3-10}$ cycloalkyl, 3-10 membered heterocyclyl, $C_{5-10}$ aryl, 5-10 membered heteroaryl, $-C_{0-8}-S(O)_rR_{19}$, $-C_{0-8}-C(O)OR_{20}$, $-C_{0-8}-C(O)R_{21}$, $-C_{0-8}-C(=NR\sim)R_{21}$ and $-C_{0-8}-C(O)NR_{22}R_{23}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_2$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$;

$R_5$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, $-SF_5$, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$;

$R_6$ and $R_7$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-C(O)NR_{22}R_{23}$ and $-C_{0-8}-NR_{22}R_{23}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$;

$R_8$ and $R_9$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-C(O)NR_{22}R_{23}$ and $-C_{0-8}-NR_{22}R_{23}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$;

$R_{10}$, $R_{11}$ and $R_{12}$ are each independently selected from the group consisting of hydrogen, deuterium, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, $-C_{0-8}-C(O)OR_{20}$, $-C_{0-8}-C(O)R_{21}$ and $-C_{0-8}-C(O)NR_{22}R_{23}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-4}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$;

$R_{13}$ and $R_{14}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—C(O)NR$_{22}$R$_{23}$ and —$C_{0-8}$—NR$_{22}$R$_{23}$, or, $R_{13}$ and $R_{14}$, together with the carbon atom directly attached thereto, form 3-10 membered cycloalkyl or 3-10 membered heterocyclyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$;

$R_{15}$ and $R_{16}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$, or, $R_{15}$ and $R_{16}$, together with the carbon atom directly attached thereto, form 3-10 membered cycloalkyl or 3-10 membered heterocyclyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$;

$R_{17}$ and $R_{18}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —SF$_5$, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$;

each $R_{19}$ is independently selected from the group consisting of hydrogen, deuterium, hydroxy, $C_{1-10}$ alkyl, $C_{2-10}$ alkenyl, $C_{3-10}$ cycloalkyl, 3-10 membered heterocyclyl, $C_{5-10}$ aryl, 5-10 membered heteroaryl and —NR$_{22}$R$_{23}$, above groups are optionally further substituted by one or more substituents selected from the group consisting of deuterium, halogen, hydroxy, =O, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{1-10}$ aryl, $C_{5-10}$ aryloxy, 5-10 membered heteroaryl, 5-10 membered heteroaryloxy and —NR$_{22}$R$_{23}$;

each $R_{20}$ is independently selected from the group consisting of hydrogen, deuterium, $C_{1-10}$ alkyl, $C_{2-10}$ alkenyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, hydroxy, =O, cyano, $C_{1-10}$ alkyl, $C_{2-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{22}$R$_{23}$;

each $R_{21}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{22}$R$_{23}$, above groups are optionally further substituted by one or more substituents selected from the group consisting of deuterium, halogen, hydroxy, cyano, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{22}$R$_{23}$;

$R_{22}$ and $R_{23}$ are each independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, sulfonyl, methylsulfonyl, isopropylsulfonyl, cyclopropylsulfonyl, p-toluenesulfonyl, amino, monoalkylamino, dialkylamino and $C_{1-10}$ alkanoyl, above groups are optionally further substituted by one or more substituents selected from the group consisting of deuterium, halogen, hydroxy, $C_{1-8}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl;

or, $R_{22}$ and $R_{23}$, together with the nitrogen atom directly attached thereto, form 4-10 membered heterocyclyl, above groups are optionally further substituted by one or more substituents selected from the group consisting of deuterium, halogen, hydroxy, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-10}$ alkanoyl; and each r is independently 0, 1 or 2.

As a preferred embodiment, in the compound of formula (I), the stereoisomer, prodrug or pharmaceutically acceptable salt thereof, $R_{15}$ and $R_{16}$ are each independently selected from the group consisting of hydrogen, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, —$C_{0-4}$—O—$R_{20}$, —$C_{0-4}$—C(O)O$R_{20}$ and —$C_{0-4}$—N$R_{22}R_{23}$, or, $R_{15}$ and $R_{16}$, together with the carbon atom directly attached thereto, form 3-8 membered cycloalkyl or 3-8 membered heterocyclyl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, —$C_{0-4}$—O—$R_{20}$, —$C_{0-4}$—C(O)O$R_{20}$ and —$C_{0-4}$—N$R_{22}R_{23}$, wherein, $R_{20}$, $R_{22}$ and $R_{23}$ are defined as in the compound of formula (I).

As a preferred embodiment, in the compound of formula (I), the stereoisomer, prodrug or pharmaceutically acceptable salt thereof, $R_{15}$ and $R_{16}$ are each independently selected from the group consisting of hydrogen, deuterium, F, cyano, methyl, ethyl, isopropyl, allyl, ethynyl, cyclopropyl, trifluoromethyl, trideuteriomethyl, methoxy, trifluoromethoxy, trideuteriomethoxy, amino and dimethylamino, or, $R_{15}$ and $R_{16}$, together with the carbon atom directly attached thereto, form 3-4 membered cycloalkyl or 4-5 membered heterocyclyl.

As a preferred embodiment, in the compound of formula (I), the stereoisomer, prodrug or pharmaceutically acceptable salt thereof, $R_{13}$ and $R_{14}$ are each independently selected from the group consisting of hydrogen, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, —$C_{0-4}$—O—$R_{20}$, —$C_{0-4}$—C(O)O$R_{20}$ and —$C_{0-4}$—N$R_{22}R_{23}$, or, $R_{13}$ and $R_{14}$, together with the carbon atom directly attached thereto, form 3-8 membered cycloalkyl or 3-8 membered heterocyclyl, above groups are optionally further substituted by one or more substituents selected from the group consisting of deuterium, halogen, cyano, $C_{1-4}$ alkyl, $C_{2-4}$ alkenyl, $C_{24}$ alkynyl, $C_{1-4}$ haloalkyl, $C_{1-4}$ deuterioalkyl, $C_{3-8}$ cycloalkyl, 3-8 membered heterocyclyl, —$C_{0-4}$—O—$R_{20}$, —$C_{0-4}$—C(O)O$R_{20}$ and —$C_{0-4}$—N$R_{22}R_{23}$, wherein, $R_{20}$, $R_{22}$ and $R_{23}$ are defined as those in the compound of formula (I).

As a further preferred embodiment, in the compound of formula (I), the stereoisomer, prodrug or pharmaceutically acceptable salt thereof, $R_{13}$ and $R_{14}$ are each independently selected from the group consisting of hydrogen, deuterium, F, cyano, methyl, ethyl, isopropyl, allyl, ethynyl, cyclopropyl, trifluoromethyl, trideuteriomethyl, methoxy, trifluoromethoxy, trideuteriomethoxy, amino and dimethylamino, or, $R_{13}$ and $R_{14}$, together with the carbon atom directly attached thereto, form 3-4 membered cycloalkyl or 4-5 membered heterocyclyl.

As a preferred embodiment, in the compound of formula (I), the stereoisomer, prodrug or pharmaceutically acceptable salt thereof, $R_{17}$ and $R_{18}$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —SF$_5$, —$C_{0-4}$—S(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, wherein, $R_{19}$, $R_{20}$, $R_{21}$, $R_{22}$, $R_{23}$ and r are defined as those in the compound of formula (I).

As a preferred embodiment, in the compound of formula (I), the stereoisomer, prodrug or pharmaceutically acceptable salt thereof, $R_6$ and $R_7$ are each independently selected from the group consisting of hydrogen, deuterium, halogen, cyano, nitro, azido. $C_{0-4}$ alkyl, $C_{2-4}$ alkenyl, $C_{2-4}$ alkynyl, —$C_{0-4}$—S(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$ and —$C_{0-4}$—C(O)N$R_{22}R_{23}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—S(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$;

$R_8$ and $R_9$ are each independently selected from the group consisting of hydrogen, deuterium, halogen, cyano, nitro, azido, $C_{1-4}$ alkyl, $C_{2-4}$ alkenyl, $C_{2-4}$ alkynyl, —$C_{0-4}$—S(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$ and —$C_{0-4}$—C(O)N$R_{22}R_{23}$, above groups are optionally further substituted by one or more substituents selected from the group consisting of deuterium, halogen, cyano, nitro, azido, $C_{0-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—S(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, wherein, $R_{10}$, $R_{20}$, $R_{21}$, $R_{22}$, $R_{23}$ and r are defined as those in the compound of formula (I).

As a preferred embodiment, in the compound of formula (I), the stereoisomer, prodrug or pharmaceutically acceptable salt thereof, $R_{10}$, $R_{11}$, and $R_{12}$ are each independently selected from the group consisting of hydrogen, deuterium, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—C(O)O$R_{20}$, —$C_{0-4}$—C(O)$R_{21}$ and —$C_{0-4}$—C(O)N$R_{22}R_{23}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—S(O)$_r$$R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, wherein, $R_{19}$, $R_{20}$, $R_{21}$, $R_{22}$, $R_{23}$ and r are defined those in the compound of formula (I).

As a preferred embodiment, in the compound of formula (I), the stereoisomer, prodrug or pharmaceutically acceptable salt thereof, $R_2$ and $R_3$ are each independently selected from the group consisting of hydrogen, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, —$C_{0-4}$—O—$R_{20}$, —$C_{0-4}$—C(O)O$R_{20}$ and —$C_{0-4}$—N$R_{22}R_{23}$, or, $R_2$ and $R_3$, together with the carbon atom directly attached thereto, form 3-8 membered cycloalkyl or 3-8 membered heterocyclyl, or, one of $R_2$ and $R_3$, together with $R_1$ and the group directly attached thereto, form 4-10 membered cycloalkyl or 4-10 membered heterocyclyl, and the other one is selected from the group consisting of hydrogen, deuterium, F and $C_{1-4}$alkyl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{0-4}$ haloalkyl, $C_{1-4}$ deuterioalkyl, $C_{3-8}$ cycloalkyl, 3-8 membered heterocyclyl, —$C_{0-4}$—O—$R_{20}$, —$C_{0-4}$—C(O)O$R_{20}$ and —$C_{0-4}$—N$R_{22}R_{23}$, wherein, $R_1$, $R_{20}$, $R_{22}$ and $R_{23}$ are defined as those in the compound of formula (I).

As a further preferred embodiment, in the compound of formula (I), the stereoisomer, prodrug or pharmaceutically acceptable salt thereof, $R_2$ and $R_3$ are each independently selected from the group consisting of hydrogen, deuterium, F, Cl, cyano, methyl, ethyl, isopropyl, allyl, ethynyl, cyclopropyl, hydroxymethyl, cyanomethyl, trifluoromethyl, trideuteriomethyl, trifluoromethoxy, trideuteriomethoxy, methoxy, amino, methylamino and dimethylamino, or, $R_2$ and $R_3$, together with the carbon atom directly attached thereto, form 3-4 membered cycloalkyl or 4-5 membered heterocyclyl, or, one of $R_2$ and $R_3$, together with $R_1$ and the group directly attached thereto, form 4-6 membered cycloalkyl or 4-6 membered heterocyclyl, the other one is selected from the group consisting of hydrogen, deuterium and methyl; wherein, $R_1$ is defined as those in the compound of formula (I).

As a preferred embodiment, in the compound of formula (I), the stereoisomer, prodrug or pharmaceutically acceptable salt thereof, $R_4$ is selected from the group consisting of hydrogen, deuterium, $C_{1-4}$ alkyl, $C_{2-4}$ alkenyl, $C_{3-8}$ cycloalkyl, 3-8 membered heterocyclyl, $C_{5-8}$ aryl, 5-8 membered heteroaryl, —$C_{0-4}$—S(O)$_r R_{19}$, —$C_{0-4}$—C(O)O$R_2$O, —$C_{0-4}$—C(O)$R_{21}$, —$C_{0-4}$—C(=N$R_{22}$)$R_{21}$ and —$C_{0-4}$—C(O)N$R_{22}R_{23}$, above groups are optionally further substituted by one or more substituents selected from the group consisting of deuterium, halogen, cyano, nitro, azido. $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—S(O)$_r R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, wherein, $R_{19}$, $R_{20}$, $R_{21}$, $R_{22}$, $R_{23}$ and r are defined as those in the compound of formula (I).

As a preferred embodiment, in the compound of formula (I), the stereoisomer, prodrug or pharmaceutically acceptable salt thereof, $R_1$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—SF$_5$, —$C_{0-4}$—S(O)$_r R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, or, when m≥2, two of $R_1$ together with the moiety directly attached thereto form 4-8 membered cycloalkyl, 5-8 membered aryl, 4-8 membered heterocyclyl or 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—S(O)$_r R_{19}$, —$C_{0-4}$—O—$R_{20}$, —$C_{0-4}$—C(O)O$R_{20}$, —$C_{0-4}$—C(O)$R_{21}$, —$C_{0-4}$—O—C(O)$R_{21}$, —$C_{0-4}$—N$R_{22}R_{23}$, —$C_{0-4}$—C(=N$R_{22}$)$R_{21}$, —$C_{0-4}$—N($R_{22}$)—C(=N$R_{23}$)$R_{21}$, —$C_{0-4}$—C(O)N$R_{22}R_{23}$ and —$C_{0-4}$—N($R_{22}$)—C(O)$R_{21}$, wherein, $R_{19}$, $R_{20}$, $R_{21}$, $R_{22}$, $R_{23}$ and r are defined as those in the compound of formula (I).

As a further preferred embodiment, in the compound of formula (I), the stereoisomer, prodrug or pharmaceutically acceptable salt thereof, the compound of formula (I) is a compound having formula (IIa), formula (IIb) or formula (IIc);

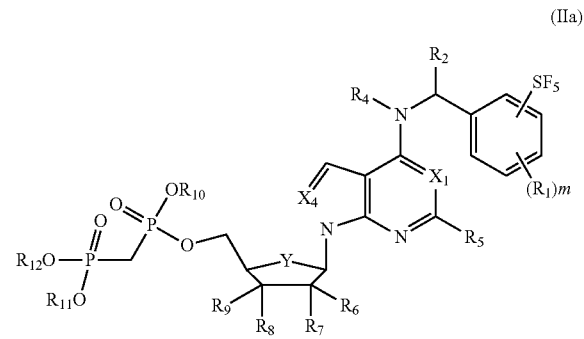

(IIa)

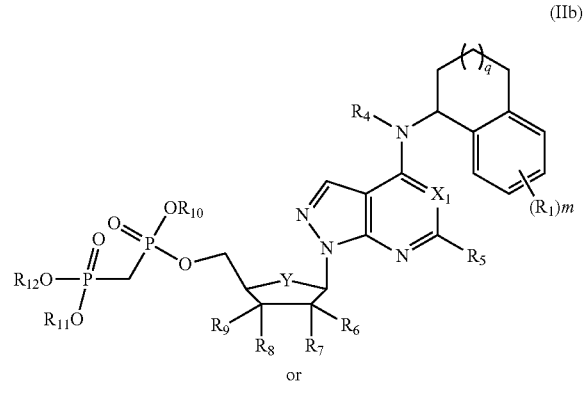

(IIb)

or

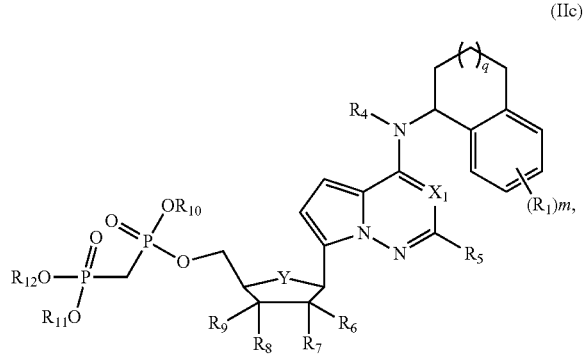

(IIc)

wherein, each $X_1$ is independently N or CH; each $X_4$ is independently N or CH; each Y is independently $CH_2$ or O;

each $R_1$ is independently selected from the group consisting of hydrogen, deuterium, halogen, cyano, nitro, $C_{1-4}$ alkyl, $C_{3-6}$ cycloalkyl, 3-6 membered heterocyclyl, $C_{5-6}$ aryl, 5-6 membered heteroaryl, —SF$_5$, —S(O)$_r R_{19}$, —O—$R_{20}$, —C(O)O$R_{20}$, —C(O)$R_{21}$, —O—C(O)$R_{21}$ and —N$R_{22}R_{23}$, or, when m≥2, two of $R_1$ together with the moiety directly attached thereto form 5-6 membered cycloalkyl, 5-6 membered aryl, 5-6 membered heterocyclyl or 5-6 membered heteroaryl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-6}$ aryl, 5-6 membered heteroaryl, =O, —S(O)$_r R_{19}$, —O—$R_{20}$, —C(O)O$R_{20}$, —C(O)$R_{21}$, —O—C(O)$R_{21}$ and —N$R_{22}R_{23}$;

$R_2$ is selected from the group consisting of hydrogen, deuterium, F, Cl, cyano, methyl, ethyl, isopropyl, allyl, ethynyl, cyclopropyl, hydroxymethyl, cyanomethyl, trifluoromethyl, trideuteriomethyl, methoxy, trifluoromethoxy, trideuteriomethoxy, amino, methylamino and dimethylamino;

each $R_4$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-6}$ aryl and 5-6 membered heteroaryl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-6}$ aryl, 5-6 membered heteroaryl, =O, —S(O)$_r R_{19}$, —O—$R_{20}$, —C(O)O$R_{20}$, —C(O)$R_{21}$, —O—C(O)$R_{21}$ and —N$R_{22}R_{23}$;

each $R_5$ is independently selected from the group consisting of hydrogen, deuterium, halogen, cyano, $C_{1-4}$ alkyl, $C_{3-6}$ cycloalkyl, 3-6 membered heterocyclyl, phenyl, 5-6 membered heteroaryl, —SF$_5$, methylthio, methylsulfonyl, isopropylsulfonyl, aminosulfonyl, methoxy, ethyoxyl, isopropoxy, hydroxy, —C(O)OH, methoxycarbonyl, ethoxycarbonyl, formyl, acetyl, acetoxyl, amino, dimethylamino, —C(=N$R_{22}$)$R_{21}$, —N($R_{22}$)—C(=N$R_{23}$)$R_{21}$, aminocarbonyl, dimethylaminocarbonyl and acetylamino, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{0-4}$ deuterioalkyl, $C_{3-6}$ cycloalkyl, 3-6 membered heterocyclyl, phenyl, 5-6 membered heteroaryl, =O, methylthio, methylsulfonyl, isopropylsulfonyl, aminosulfonyl, methoxy, ethyoxyl, isopropoxy, hydroxy, —C(O)OH, methoxycarbonyl, ethoxycarbonyl, formyl, acetyl, acetoxyl, amino, dimethylamino, aminocarbonyl, dimethylaminocarbonyl and acetylamino;

$R_6$ and $R_7$ are each independently selected from the group consisting of hydrogen, deuterium, halogen, cyano, nitro, azido, methyl, ethyl, n-propyl, isopropyl, vinyl, 1-propenyl, 2-propenyl, ethynyl, hydroxy, methoxy and acetoxyl, above groups are optionally further substituted by one or more substituents selected from the group consisting of deuterium, halogen, cyano, methyl, ethyl, n-propyl, isopropyl, vinyl, ethynyl, cyclopropyl, trifluoromethyl, trideuteriomethyl, hydroxy, methoxy and acetoxyl;

$R_8$ and $R_9$ are each independently selected from the group consisting of hydrogen, deuterium, halogen, cyano, nitro, azido, methyl, ethyl, n-propyl, isopropyl, vinyl, 1-propenyl, 2-propenyl, ethynyl, cyclopropyl, hydroxy, methoxy and acetoxyl, above groups are optionally further substituted by one or more substituents selected from the group consisting of deuterium, halogen, cyano, methyl, ethyl, n-propyl, isopropyl, vinyl, ethynyl, cyclopropyl, trifluoromethyl, trideuteriomethyl, hydroxy, methoxy and acetoxyl;

$R_{10}$, $R_{11}$ and $R_{12}$ are each independently selected from the group consisting of hydrogen, deuterium, $C_{1-4}$ alkyl, $C_{3-6}$ cycloalkyl, 3-6 membered heterocyclyl, $C_{5-6}$ aryl, 5-6 membered heteroaryl, —C(O)O$R_{20}$, —C(O)$R_{21}$ and —C(O)N$R_{22}R_{23}$, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-6}$ aryl, 5-6 membered heteroaryl, =O, —S(O)$_r R_{19}$, —O—$R_{20}$, —C(O)O$R_{20}$, —C(O)$R_{21}$, —O—C(O)$R_{21}$, —N$R_{22}R_{23}$, —C(O)N$R_{22}R_{23}$ and —N($R_{22}$)—C(O)$R_{21}$;

each $R_{19}$ is independently selected from the group consisting of hydrogen, deuterium, hydroxy, $C_{1-4}$ alkyl, $C_{2-6}$ alkenyl, $C_{3-6}$ cycloalkyl, 3-6 membered heterocyclyl, $C_{5-6}$ aryl, 5-6 membered heteroaryl and —N$R_{22}R_{23}$, above groups are optionally further substituted by one or more substituents selected from the group consisting of deuterium, halogen, hydroxy, =O, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —N$R_{22}R_{23}$;

each $R_{20}$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-6}$ aryl and 5-6 membered heteroaryl, above groups are optionally further substituted by one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —N$R_{22}R_{23}$;

each $R_{21}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —N$R_{22}R_{23}$, above groups are optionally further substituted by one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —N$R_{22}R_{23}$;

$R_{22}$ and $R_{23}$ are each independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{5-6}$ aryl, 5-6 membered heteroaryl, sulfonyl, methylsulfonyl, isopropylsulfonyl, cyclopropylsulfonyl, p-toluenesulfonyl, amino, monoalkylamino, dialkylamino and $C_{1-4}$ alkanoyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy, amino, monoalkylamino, dialkylamino and $C_{1-4}$ alkanoyl;

or, $R_{22}$ and $R_{23}$, together with the nitrogen atom directly attached thereto, form 4-6 membered heterocyclyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy, amino, monoalkylamino, dialkylamino and $C_{1-4}$ alkanoyl;

each q is independently 0, 1, 2 or 3;

each m is independently 0, 1, 2 or 3; and each r is independently 0, 1 or 2.

As a further preferred embodiment, in the compound of formula (I), the stereoisomer, prodrug or pharmaceutically acceptable salt thereof, each $R_1$ is independently selected from the group consisting of hydrogen, deuterium, halogen, cyano, nitro, $C_{1-4}$ alkyl, $C_{3-6}$ cycloalkyl, 3-6 membered heterocyclyl, $C_{5-6}$ aryl, 5-6 membered heteroaryl, —$SF_5$, —$S(O)_rR_{19}$, —O—$R_{20}$, —C(O)O$R_{20}$, —C(O)$R_{21}$, —O—C(O)$R_{21}$ and —$NR_{22}R_{23}$, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —O—$R_{20}$, —C(O)O$R_{20}$ and —C(O)$R_{21}$;

each $R_4$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-6}$ aryl and 5-6 membered heteroaryl, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —O—$R_{20}$, —C(O)O$R_{20}$ and —C(O)$R_{21}$;

each $R_5$ is independently selected from the group consisting of hydrogen, deuterium, halogen, cyano, $C_{1-4}$ alkyl, $C_{3-6}$ cycloalkyl, 3-6 membered heterocyclyl, phenyl, 5-6 membered heteroaryl, —$SF_5$, methylthio, methylsulfonyl, isopropylsulfonyl, aminosulfonyl, methoxy, ethyoxyl, isopropoxy, hydroxy, —C(O)OH, methoxycarbonyl, ethoxycarbonyl, formyl, acetyl, acetoxyl, amino, dimethylamino, aminocarbonyl, dimethylaminocarbonyl and acetylamino, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, methoxy, ethyoxyl, isopropoxy, hydroxy, —C(O)OH, methoxycarbonyl, ethoxycarbonyl, formyl, acetyl and acetoxyl;

$R_6$ and $R_7$ are each independently selected from the group consisting of hydrogen, deuterium, halogen, cyano, nitro, azido, methyl, ethyl, n-propyl, isopropyl, hydroxy, methoxy and acetoxyl, above groups are optionally further substituted by one or more substituents selected from the group consisting of deuterium, halogen, cyano, methyl, ethyl, n-propyl, isopropyl, vinyl, ethynyl, cyclopropyl, trifluoromethyl, trideuteriomethyl, hydroxy, methoxy and acetoxyl;

$R_8$ and $R_9$ are each independently selected from the group consisting of hydrogen, deuterium, halogen, cyano, nitro, azido, methyl, ethyl, n-propyl, isopropyl, cyclopropyl, hydroxy, methoxy and acetoxyl, above groups are optionally further substituted by one or more substituents selected from the group consisting of deuterium, halogen, cyano, methyl, ethyl, n-propyl, isopropyl, cyclopropyl, trifluoromethyl, trideuteriomethyl, hydroxy, methoxy and acetoxyl;

$R_{10}$, $R_{11}$ and $R_{12}$ are each independently selected from the group consisting of hydrogen, deuterium, $C_{0-4}$ alkyl, $C_{3-6}$ cycloalkyl, 3-6 membered heterocyclyl, $C_{5-6}$ aryl, 5-6 membered heteroaryl, —C(O)O$R_{20}$, —C(O)$R_{21}$ and —C(O)$NR_{22}R_{23}$, above groups are optionally further substituted by one or more substituents selected from the group consisting of deuterium, halogen, cyano, $C_{0-4}$ alkyl, $C_{1-4}$ haloalkyl, $C_{1-4}$ deuterioalkyl, $C_{3-6}$ cycloalkyl, 3-6 membered heterocyclyl, =O, —S(O)$_rR_{19}$, —O—$R_{20}$, —C(O)O$R_{20}$, —C(O)$R_{21}$ and —O—C(O)$R_{21}$;

each $R_{19}$ is independently selected from the group consisting of hydrogen, deuterium, hydroxy, $C_{1-4}$ alkyl and $C_{3-6}$ cycloalkyl, above groups are optionally further substituted by one or more substituents selected from the group consisting of deuterium, halogen, hydroxy, =O, $C_{1-4}$ alkyl, $C_{1-4}$ alkoxy and $C_{3-6}$ cycloalkyl;

each $R_{20}$ is independently selected from the group consisting of hydrogen, deuterium, $C_{1-4}$ alkyl and $C_{3-6}$ cycloalkyl, above groups are optionally further substituted by one or more substituents selected from the group consisting of deuterium, halogen, hydroxy, =O, cyano, $C_{1-4}$ alkyl, $C_{1-4}$ alkoxy and $C_{3-6}$ cycloalkyl;

each $R_{21}$ is independently selected from the group consisting of hydrogen, deuterium, hydroxy, $C_{1-4}$ alkyl and $C_{1-4}$ alkoxy, above groups are optionally further substituted by one or more substituents selected from the group consisting of deuterium, halogen, hydroxy, cyano, $C_{1-4}$ alkyl, $C_{1-4}$ alkoxy and $C_{3-6}$ cycloalkyl;

$R_{22}$ and $R_{23}$ are each independently selected from the group consisting of hydrogen, deuterium, hydroxy, $C_{1-4}$ alkyl, $C_{3-6}$ cycloalkyl, 3-6 membered heterocyclyl and $C_{1-4}$ alkanoyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkoxy, 3-6 membered heterocyclyl and $C_{1-4}$ alkanoyl.

As a more further preferred embodiment, in the compound of formula (I), the stereoisomer, prodrug or pharmaceutically acceptable salt thereof, the compound of the formula (I) is a compound of the formula (IIIa1) or formula (IIIa2):

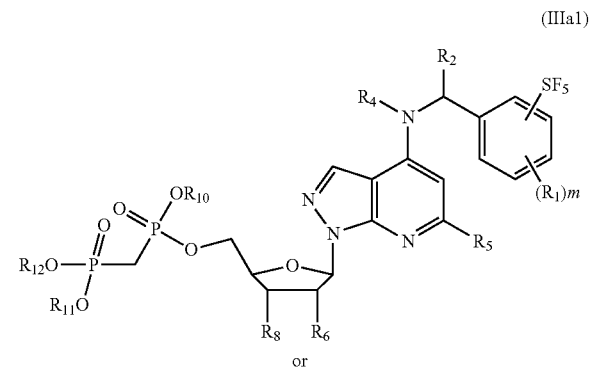

(IIIa1)

or

-continued

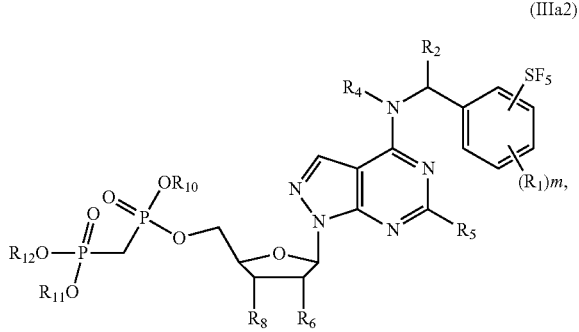

(IIIa2)

wherein, each $R_1$ is independently selected from the group consisting of hydrogen, deuterium, F, Cl, cyano, methyl, ethyl, n-propyl, isopropyl, difluoromethyl, trifluoromethyl, dideuterio methyl, trideuteriomethyl, $C_{3-6}$ cycloalkyl and 3-6 membered heterocyclyl;

each $R_2$ is independently selected from the group consisting of hydrogen, deuterium, F, Cl, cyano, methyl, ethyl, n-propyl, isopropyl, allyl, ethynyl, cyclopropyl and hydroxymethyl;

each $R_4$ is independently selected from the group consisting of hydrogen, deuterium, methyl, ethyl, n-propyl, isopropyl, $C_{2-4}$ alkenyl and $C_{3-6}$ cycloalkyl;

each $R_5$ is independently selected from the group consisting of hydrogen, deuterium, F, Cl, cyano, azido, methyl, ethyl, n-propyl, isopropyl, $C_{2-6}$ alkenyl, $C_{2-6}$ alkynyl and $C_{3-6}$ cycloalkyl;

each $R_6$ is independently selected from the group consisting of hydrogen, deuterium, halogen, methyl, ethyl, n-propyl, isopropyl and hydroxy;

each $R_8$ is independently selected from the group consisting of hydrogen, deuterium, halogen, methyl, ethyl, n-propyl, isopropyl and hydroxy;

$R_{10}$, $R_{11}$ and $R_{12}$ are each independently selected from the group consisting of hydrogen, deuterium, methyl, ethyl, n-propyl and isopropyl; and each m is independently 0, 1, 2 or 3.

As a more further preferred embodiment, in the compound of the formula (I), the stereoisomer, prodrug or pharmaceutically acceptable salt thereof, the compound of formula (I) is a compound of formula (IIIb):

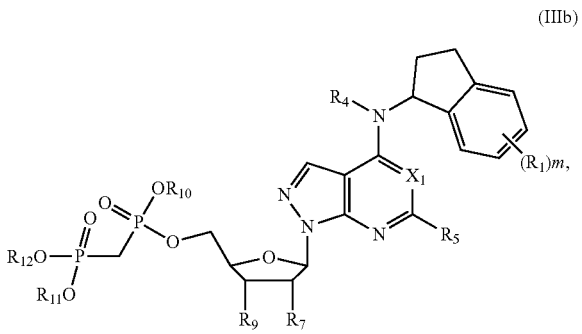

(IIIb)

wherein, $X_1$ is N or CH;
wherein, $R_1$ is selected from the group consisting of hydrogen, deuterium, F, Cl, cyano, methyl, ethyl, n-propyl, isopropyl, difluoromethyl, trifluoromethyl, dideuteriomethyl, trideuteriomethyl, $C_{3-6}$ cycloalkyl and 3-6 membered heterocyclyl;

$R_4$ is selected from the group consisting of hydrogen, deuterium, methyl, ethyl, n-propyl, isopropyl, $C_{2-4}$ alkenyl and $C_{3-6}$ cycloalkyl;

$R_5$ is selected from the group consisting of hydrogen, deuterium, F, Cl, cyano, azido, methyl, ethyl, n-propyl, isopropyl, $C_{2-4}$ alkenyl, $C_{2-4}$ alkynyl and $C_{3-6}$ cycloalkyl;

$R_7$ is selected from the group consisting of hydrogen, deuterium, halogen, methyl, ethyl, n-propyl, isopropyl and hydroxy;

$R_9$ is selected from the group consisting of hydrogen, deuterium, halogen, methyl, ethyl, n-propyl, isopropyl and hydroxy;

$R_{10}$, $R_{11}$ and $R_{12}$ are each independently selected from the group consisting of hydrogen, deuterium, methyl, ethyl, n-propyl and isopropyl; and m is 0, 1, 2 or 3.

As a more further preferred embodiment, in the compound of the formula (I), the stereoisomer, prodrug or pharmaceutically acceptable salt thereof, the compound of formula (I) is a compound of formula (IIIc):

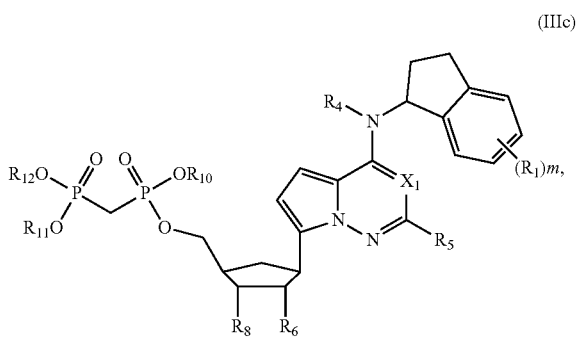

(IIIc)

wherein, $X_1$ is N or CH;

$R_1$ is selected from the group consisting of hydrogen, deuterium, F, Cl, cyano, methyl, ethyl, n-propyl, isopropyl, difluoromethyl, trifluoromethyl, dideuteriomethyl, trideuteriomethyl, $C_{3-6}$ cycloalkyl and 3-6 membered heterocyclyl;

$R_4$ is selected from the group consisting of hydrogen, deuterium, methyl, ethyl, n-propyl, isopropyl, $C_{2-4}$ alkenyl and $C_{3-6}$ cycloalkyl;

$R_5$ is selected from the group consisting of hydrogen, deuterium, F, Cl, cyano, azido, methyl, ethyl, n-propyl, isopropyl, $C_{2-6}$ alkenyl, $C_{2-6}$ alkynyl and $C_{3-6}$ cycloalkyl;

$R_6$ is selected from the group consisting of hydrogen, deuterium, halogen, methyl, ethyl, n-propyl, isopropyl and hydroxy;

$R_8$ is selected from the group consisting of hydrogen, deuterium, halogen, methyl, ethyl, n-propyl, isopropyl and hydroxy;

$R_{10}$, $R_{11}$ and $R_{12}$ are each independently selected from the group consisting of hydrogen, deuterium, methyl, ethyl, n-propyl and isopropyl; and m is 0, 1, 2 or 3.

As the most preferred embodiment, the compound of formula (I), the stereoisomer, prodrug or pharmaceutically acceptable salt thereof includes, but is not limited to, the following compounds:

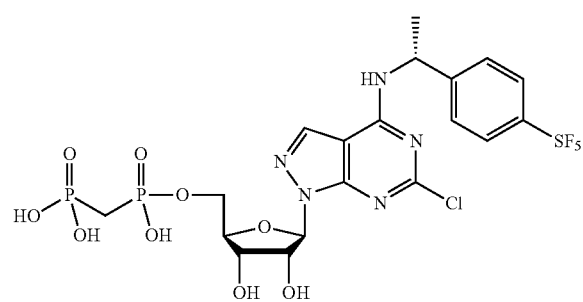
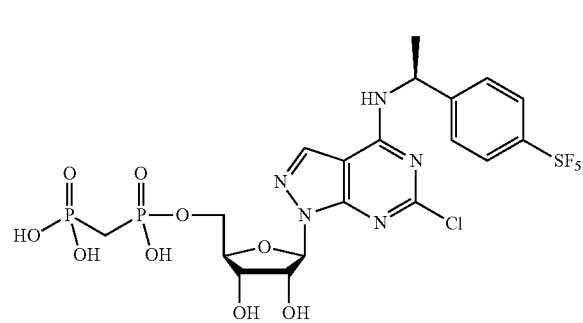
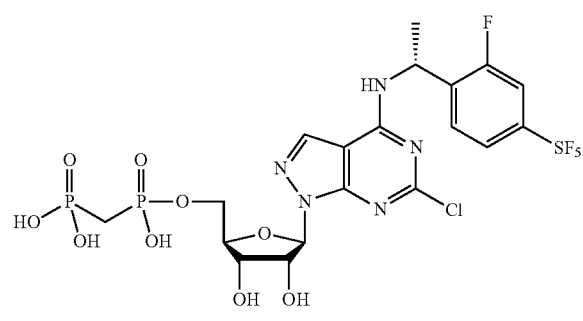
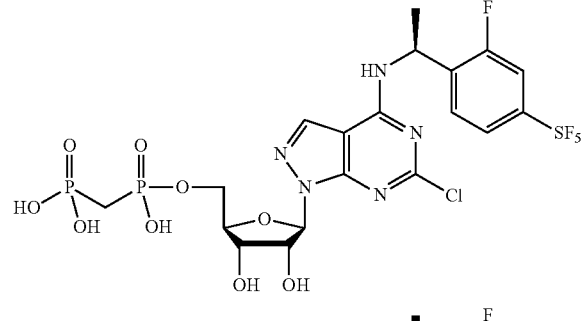
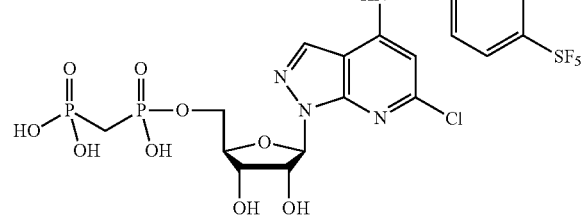
-continued
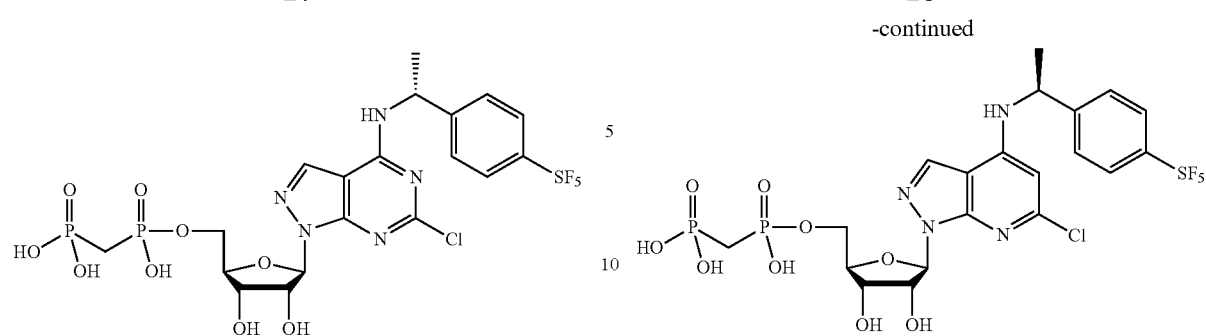
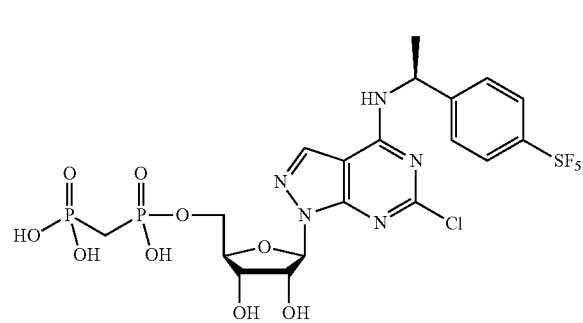
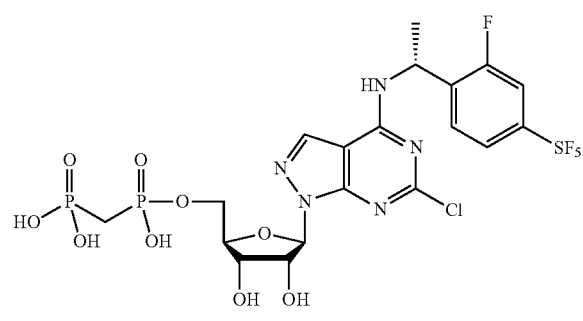
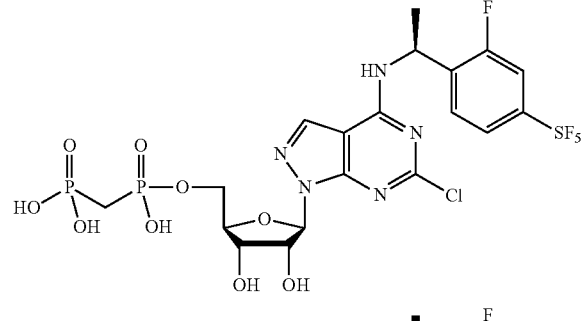
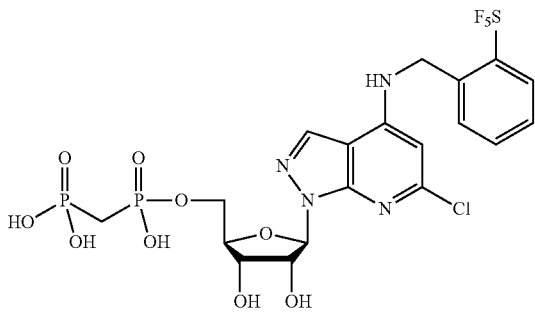

19
-continued
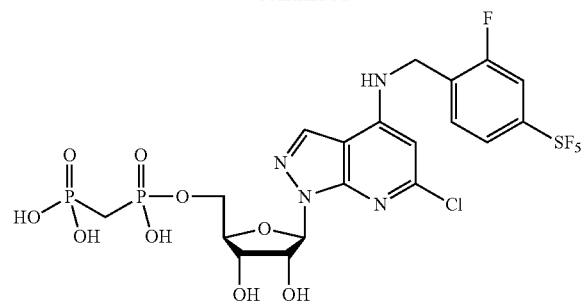
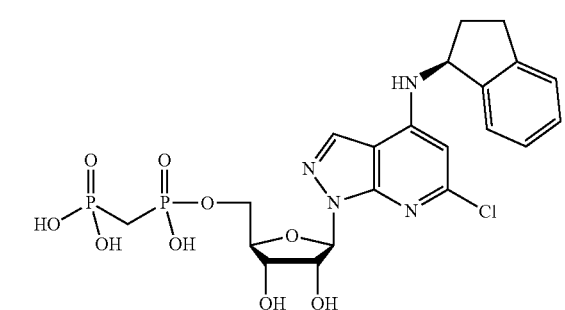
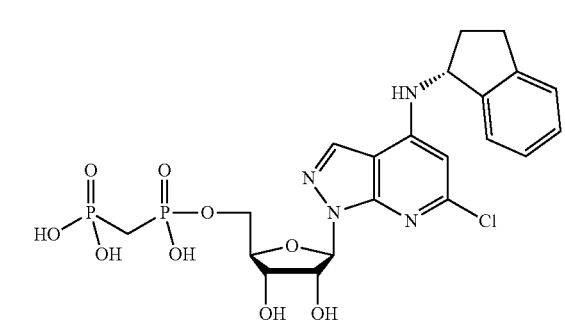
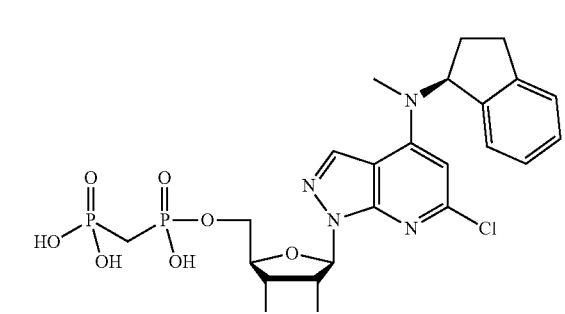
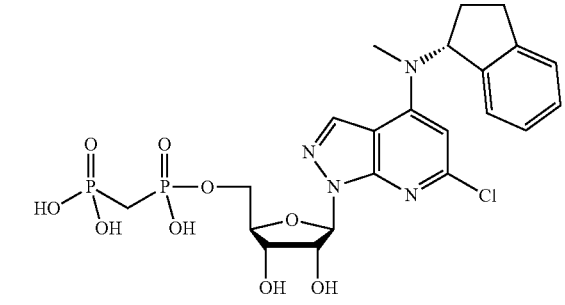
20
-continued
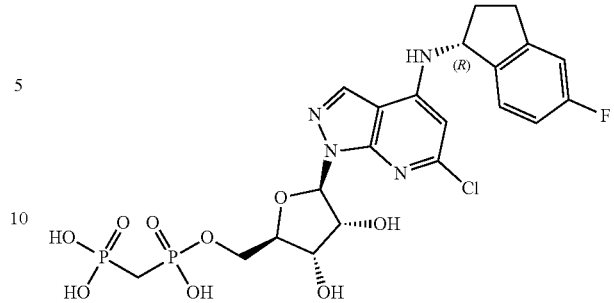
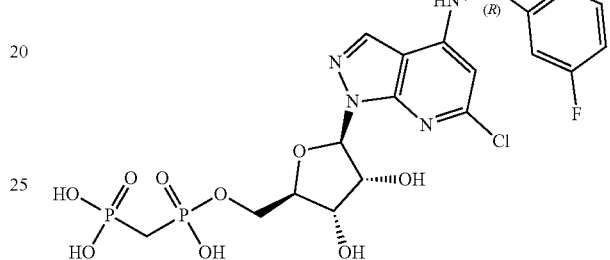
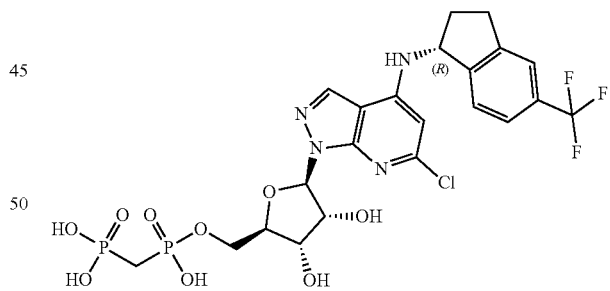
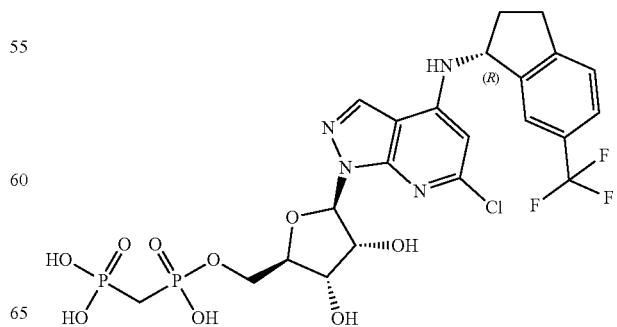

21
-continued
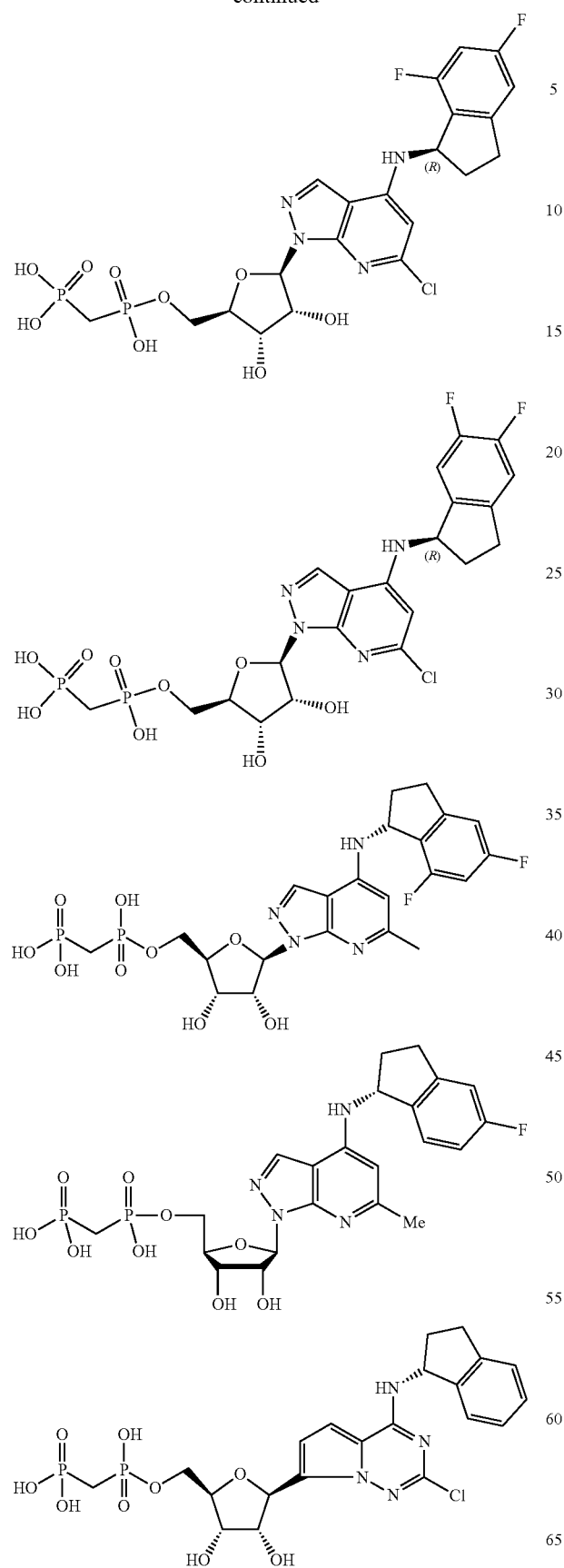
22
-continued
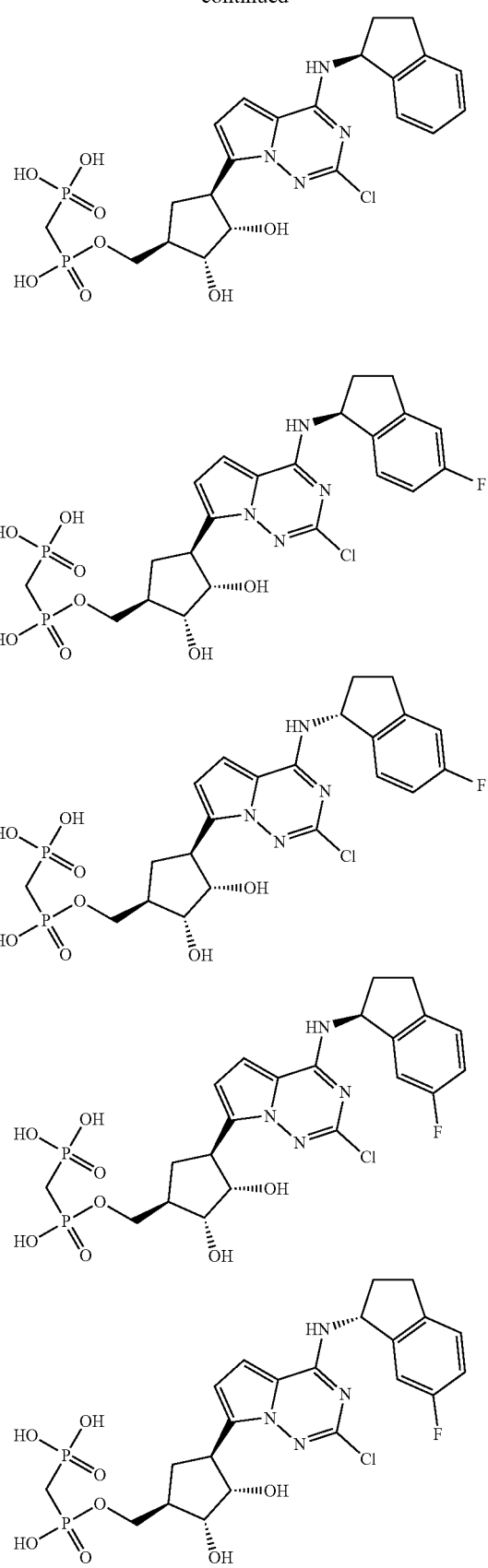

23
-continued
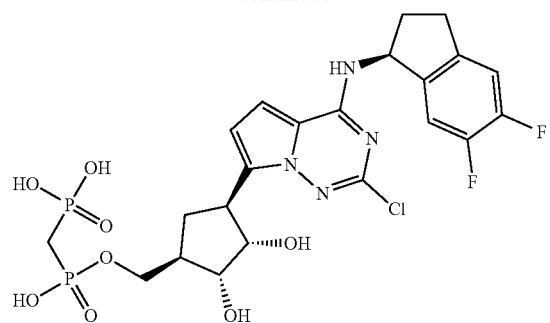
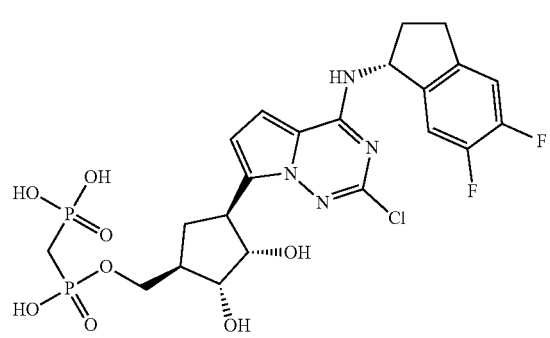
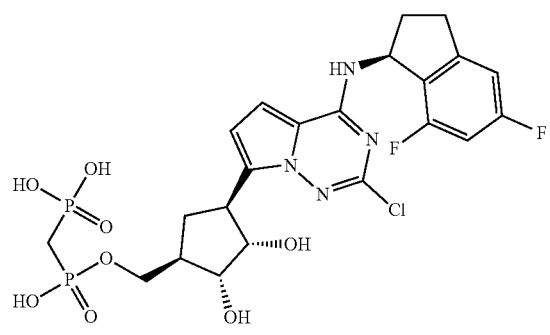
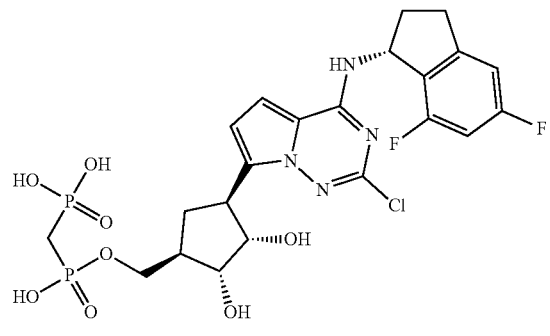
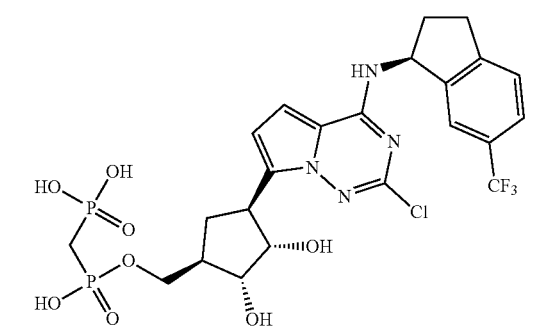
24
-continued
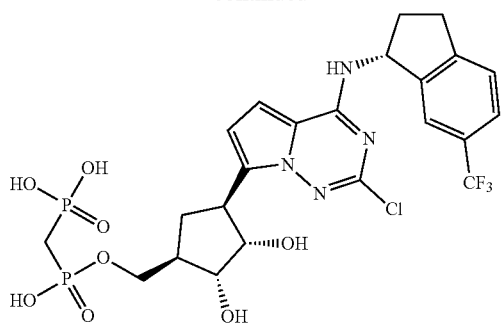
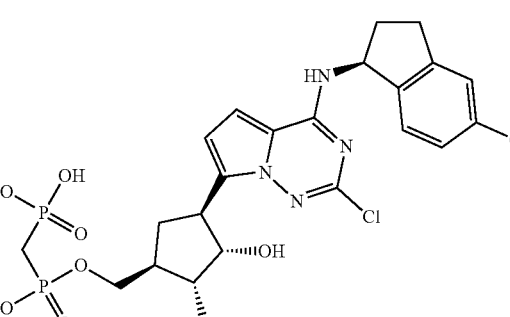
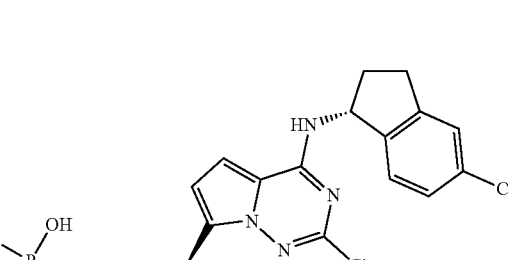
or
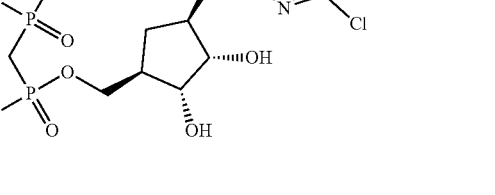
The second aspect of the present invention provides a process for preparing the compound of formula (I), the stereoisomer, prodrug or pharmaceutically acceptable salt therefore, which comprises the following steps:

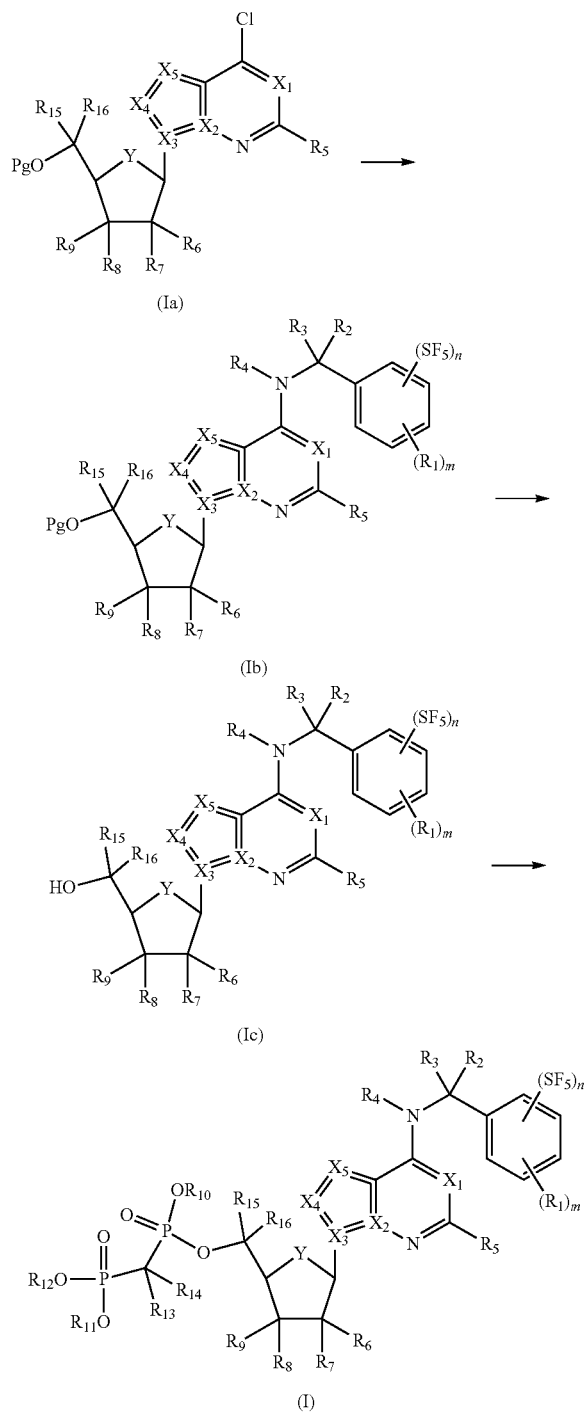

wherein, Pg is a hydroxy protecting group preferably selected from the group consisting of an alkanoyl or silicane protecting group; $X_1$, $X_2$, $X_3$, $X_4$, $X_5$, Y, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, m and n are defined as those in the compound of formula (I).

The third aspect of the present invention provides a pharmaceutical composition comprising the compound of formula (I), the stereoisomer, prodrug or pharmaceutically acceptable salt thereof, and a pharmaceutically acceptable carrier.

The fourth aspect of the present invention provides a use of the compound of formula (I), the stereoisomer, prodrug or pharmaceutically acceptable salt thereof in the preparation of a medicament for treating cancer or tumor, immune-related disease and disorder or metabolic disease, which is at least partially mediated by CD73.

As a preferred embodiment, the cancer or tumor is selected from the group consisting of prostate cancer, colon cancer, rectal cancer, pancreatic cancer, gastric cancer, endometrial cancer, cervical cancer, brain cancer, liver cancer, bladder cancer, ovarian cancer, testicular cancer, head cancer, neck cancer, skin cancer (including melanoma and basal cell carcinoma), mesothelial lining cancer, white blood cell cancer (including lymphoma and leukemia), esophageal cancer, breast cancer, muscle cancer, connective tissue cancer, lung cancer (including small cell lung cancer and non-small cell lung cancer), adrenal cancer, thyroid cancer, kidney cancer, bone cancer, brain tumor, glioblastoma, mesothelioma, renal cell carcinoma, sarcoma (including Kaposi's sarcoma), choriocarcinoma, epidermal basal cell carcinoma and testicular seminoma.

As a further preferred embodiment, the cancer or tumor are selected from the group consisting of melanoma, colon cancer, pancreatic cancer, breast cancer, prostate cancer, lung cancer, leukemia, brain tumor, lymphoma, ovarian cancer and Kaposi's sarcoma.

As a preferred embodiment, the immune-related disease and disorder is selected from the group consisting of rheumatoid arthritis, renal failure, lupus erythematosus, asthma, psoriasis, ulcerative colitis, pancreatitis, allergy, fibrosis, anemia fibromyalgia, Alzheimer's disease, congestive heart failure, stroke, aortic stenosis, arteriosclerosis, osteoporosis, Parkinson's disease, infection, Crohn's disease, ulcerative colitis, allergic contact dermatitis and eczema, systemic sclerosis and multiple sclerosis.

A fifth aspect of the present invention provides the compound of formula (I), the stereoisomer, prodrug or pharmaceutically acceptable salt thereof for use as a medicament for treating cancer or tumor, autoimmune disease and disorder or metabolic disease, which is at least partially mediated by CD73.

The sixth aspect of the present invention provides the compound of formula (I), the stereoisomer, prodrug or pharmaceutically acceptable salt thereof as described above for use as a medicament for treating prostate cancer, colon cancer, rectal cancer, pancreatic cancer, gastric cancer, endometrial cancer, cervical cancer, brain cancer, liver cancer, bladder cancer, ovarian cancer, testicular cancer, head cancer, neck cancer, skin cancer (including melanoma and basal cell carcinoma), mesothelial lining cancer, white blood cell cancer (including lymphoma and leukemia), esophageal cancer, breast cancer, muscle cancer, connective tissue cancer, lung cancer (small cell lung cancer and non-small cell lung cancer), adrenal cancer, thyroid cancer, kidney cancer, bone cancer, brain tumor, glioblastoma, mesothelioma, renal cell carcinoma, sarcoma (comprising Kaposi's sarcoma), choriocarcinoma, epidermal basal cell carcinoma, testicular seminoma, rheumatoid arthritis, renal failure, lupus erythematosus, asthma, psoriasis, ulcerative colitis, pancreatitis, allergy, fibrosis, anemia fibromyalgia, Alzheimer's disease, congestive heart failure, stroke, aortic stenosis, arteriosclerosis, osteoporosis, Parkinson's disease, infection, Crohn's disease, ulcerative colitis, allergic contact dermatitis and eczema, systemic sclerosis and multiple sclerosis.

DETAILED DESCRIPTION OF THE INVENTION

Detailed description: Unless otherwise stated, the following terms used in the specification and claims have the following meanings.

"Alkyl" refers to a straight or branched saturated aliphatic hydrocarbon group, for example, "$C_{1-10}$ alkyl" refers to a straight or branched alkyl having 1 to 10 carbon atoms, including but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof and so on. "$C_{0-8}$" refers to $C_{0-8}$ alkyl, "$C_{0-4}$" refers to $C_{0-4}$ alkyl, $C_0$ refers to 0 carbon atom, "$C_{1-4}$" refers to $C_{1-4}$ alkyl, and alkyl is as defined above.

The alkyl group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—NR$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$.

"Cycloalkyl" refers to a saturated or partially unsaturated monocyclic or polycyclic hydrocarbon substituent, for example, "$C_{3-10}$ cycloalkyl" refers to a cycloalkyl having 3-10 carbon atoms, which may be a monocyclic cycloalky and a polycyclic cycloalkyl, wherein,
  monocyclic cycloalkyl includes, but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and the like;
  and polycyclic cycloalkyl includes spiro, fused, and bridged cycloalkyls. "Spirocycloalkyl" refers to a polycyclic group that shares a carbon atom (called a spiro atom) between the monocyclic rings. These groups may contain one or more (preferably, 1, 2 or 3) double bonds, but none of the rings have a fully conjugated π-electron system. The spirocycloalkyl may be a monospirocycloalkyl, a bispirocycloalkyl or a polyspirocycloalkyl according to the number of common spiro atoms between the rings, spirocycloalkyl includes, but is not limited to:

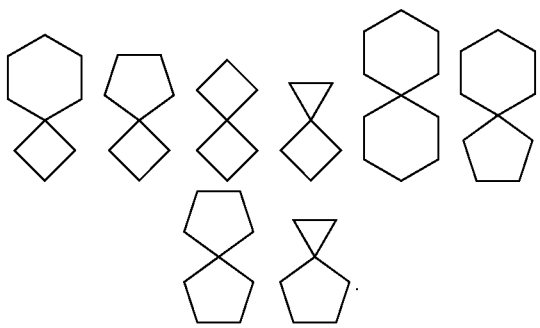

"Fused cycloalkyl" refers to an all-carbon polycyclic group in which each ring shares an adjacent pair of carbon atoms with other rings in the system, wherein one or more of the rings may contain one or more (preferably, 1, 2 or 3) double bonds, but none of the rings have a fully conjugated π-electron system. Depending on the number of rings, it may be bicyclic, tricyclic, tetracyclic or polycyclic, fused cycloalkyl includes but is not limited to:

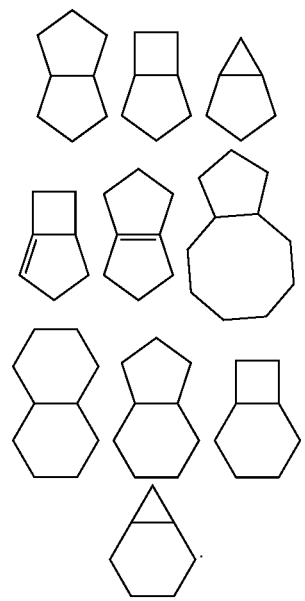

"Bridged cycloalkyl" refers to an all-carbon polycyclic group in which any two rings share two carbon atoms that are not directly bonded, which may contain one or more (preferably, 1, 2 or 3) double bonds, but none of the rings have a fully conjugated R-electron system. Depending on the number of rings, it may be bicyclic, tricyclic, tetracyclic or polycyclic, bridged cycloalkyl includes but is not limited to: Depending on the number of rings, it may be bicyclic, tricyclic, tetracyclic or polycyclic, fused cycloalkyl includes but is not limited to:

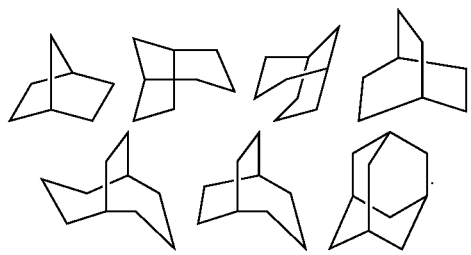

The ring of the cycloalkyl may be fused to a ring of aryl, heteroaryl or heterocycloalkyl, wherein the ring attached to the parent structure is a cycloalkyl, includes, but is not limited to indanyl, tetrahydronaphthyl, benzocycloheptyl and the likes.

The cycloalkyl group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, —$C_{0-8}$—$S(O)_rR_{19}$, —$C_{0-8}$—O—$R_{20}$, —$C_{0-8}$—C(O)O$R_{20}$, —$C_{0-8}$—C(O)$R_{21}$, —$C_{0-8}$—O—C(O)$R_{21}$, —$C_{0-8}$—N$R_{22}R_{23}$, —$C_{0-8}$—C(=N$R_{22}$)$R_{21}$, —$C_{0-8}$—N($R_{22}$)—C(=N$R_{23}$)$R_{21}$, —$C_{0-8}$—C(O)N$R_{22}R_{23}$ and —$C_{0-8}$—N($R_{22}$)—C(O)$R_{21}$.

"Heterocyclyl" refers to a saturated or partially unsaturated monocyclic or polycyclic cyclic hydrocarbon substituent wherein one or more (preferably, 1, 2, 3 or 4) of the ring atoms are heteroatoms selected from nitrogen, oxygen or $S(O)_r$ (wherein r is an integer of 0, 1, 2), but excluding ring moiety of —O—O—, —O—S— or S—S—, and the remaining ring atoms are carbon atoms. For example, "5-10 membered heterocyclyl" refers to a cyclic group containing 5 to 10 ring atoms, and "3-10 membered heterocyclyl" refers to a cyclic group containing 3 to 10 ring atoms.

Monocyclic heterocyclyl includes, but is not limited to pyrrolidinyl, piperidinyl, piperazinyl, morpholinyl, thiomorpholinyl, homopiperazinyl and the likes.

and polycyclic heterocyclyl includes spiro, fused, and bridged heterocyclyls. "Spiroheterocyclyl" refers to a polycyclic heterocyclyl that shares a carbon atom (called a spiro atom) between the monocyclic rings, wherein one or more (preferably, 1, 2, 3 or 4) of the ring atoms are heteroatoms selected from nitrogen, oxygen or $S(O)_r$ (wherein r is an integer of 0, 1, 2), and the remaining ring atoms are carbon atoms. These groups may contain one or more double bonds, but none of the rings have a fully conjugated π-electron system. The spiroheterocyclyl may be a monospiroheterocyclyl, a bispiroheterocyclyl or a polyspiroheterocyclyl according to the number of common spiro atoms between the rings, spiroheterocyclyl includes, but is not limited to:

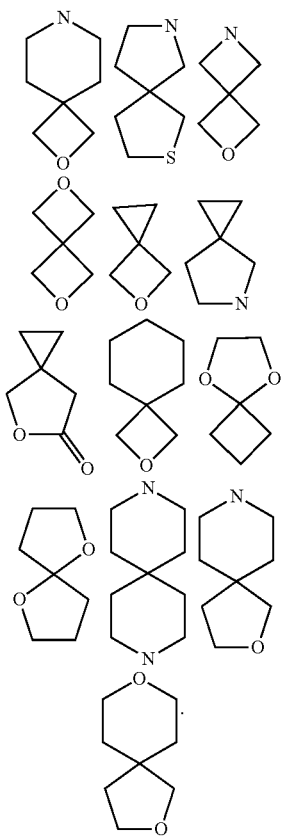

"Fused heterocyclyl" refers to a polycyclic heterocyclyl in which each ring shares an adjacent pair of carbon atoms with other rings in the system, wherein one or more (preferably, 1, 2, 3 or 4) of the rings may contain one or more (preferably, 1, 2 or 3) double bonds, but none of the rings have a fully conjugated π-electron system, wherein one or more (preferably, 1, 2, 3 or 4) of the ring atoms are heteroatoms selected from nitrogen, oxygen or $S(O)_r$ (wherein r is an integer of 0, 1, 2), and the remaining ring atoms are carbon atoms. Depending on the number of rings, it may be bicyclic, tricyclic, tetracyclic or polycyclic, fused heterocyclyl includes, but is not limited to:

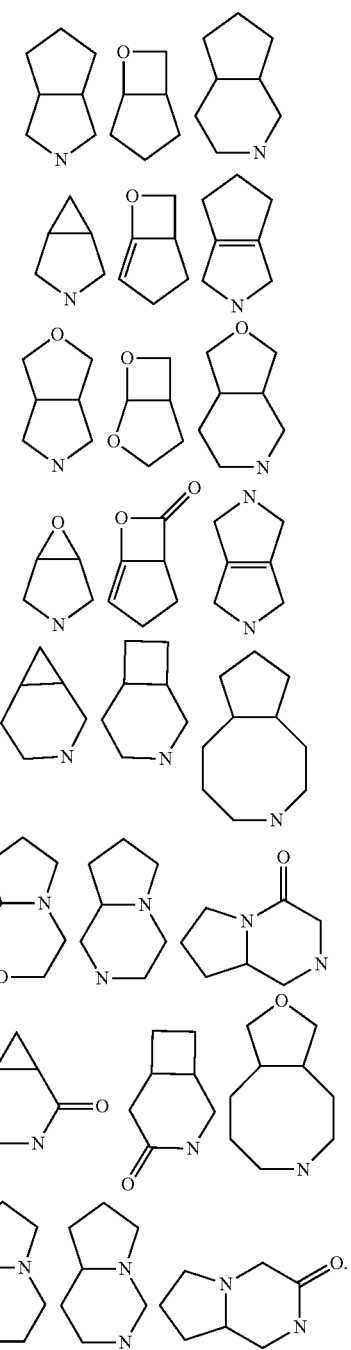

"Bridged heterocyclyl" refers to a polycyclic heterocyclyl in which any two rings share two carbon atoms that are not directly bonded, which may contain one or more (preferably, 1, 2 or 3) double bonds, but none of the rings have a fully conjugated pi-electron system, wherein one or more (preferably, 1, 2, 3 or 4) of the ring atoms are heteroatoms selected from nitrogen, oxygen or S(O)$_r$ (wherein r is an integer of 0, 1, 2), and the remaining ring atoms are carbon atoms. Depending on the number of rings, it may be bicyclic, tricyclic, tetracyclic or polycyclic, bridged heterocyclyl includes, but is not limited to:

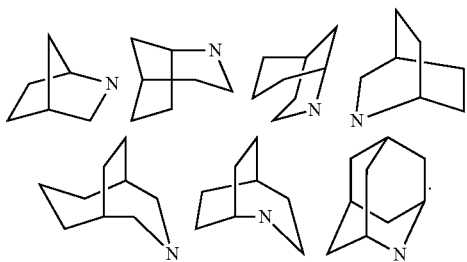

The ring of the heterocyclyl may be fused to a ring of aryl, heteroaryl or cycloalkyl wherein the ring attached to the parent structure is a heterocyclyl, includes, but is not limited to:

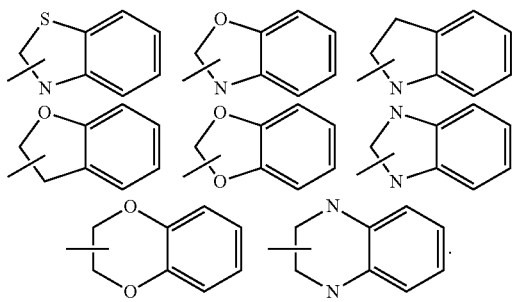

The heterocyclyl group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(=NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$.

"Aryl" refers to an all-carbon monocyclic or fused polycyclic (ie, a ring that shares a pair of adjacent carbon atoms) group, and a polycyclic group having a conjugated π-electron system (i.e., a ring with adjacent pairs of carbon atoms), for example, "$C_{5-10}$ aryl" refers to an all-carbon aryl having 5-10 carbons, and "5-10 membered aryl" refers to an all-carbon aryl having 5-10 carbons, including but not limited to phenyl and naphthyl. The aryl ring may be fused to a ring of heteroaryl, heterocyclyl or cycloalkyl, wherein the ring attached to the parent structure is an aryl ring, includes, but is not limited to:

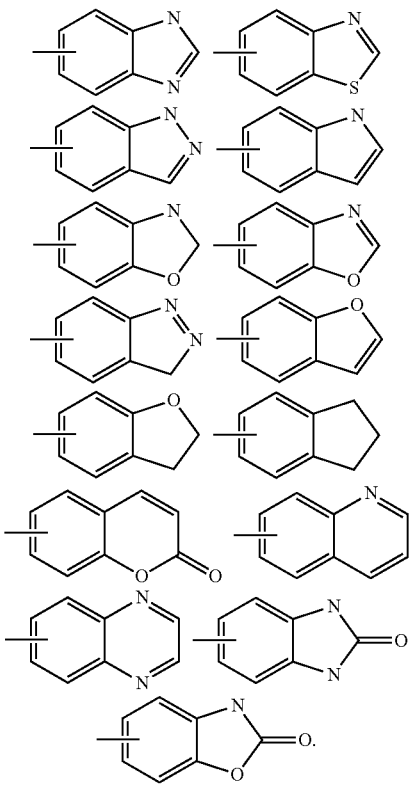

The Aryl group can be substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{7-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, —$C_{0-8}$—S(O)$_r$R$_{19}$, —$C_{0-8}$—O—R$_{20}$, —$C_{0-8}$—C(O)OR$_{20}$, —$C_{0-8}$—C(O)R$_{21}$, —$C_{0-8}$—O—C(O)R$_{21}$, —$C_{0-8}$—NR$_{22}$R$_{23}$, —$C_{0-8}$—C(NR$_{22}$)R$_{21}$, —$C_{0-8}$—N(R$_{22}$)—C(=NR$_{23}$)R$_{21}$, —$C_{0-8}$—C(O)NR$_{22}$R$_{23}$ and —$C_{0-8}$—N(R$_{22}$)—C(O)R$_{21}$.

"Heteroaryl" refers to a heteroaromatic system containing one or more (preferably, 1, 2, 3 or 4) heteroatoms including a hetero atom selected from nitrogen, oxygen or S(O)r (wherein r is an integer of 0, 1, 2), for example, 5-8 membered heteroaryl refers to a heteroaromatic system containing 5 to 8 ring atoms, and 5-10 membered heteroaryl refers to a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl group or the like. The heteroaryl ring may be fused to a ring of aryl, heterocyclyl or cycloalkyl wherein the ring attached to the parent structure is a heteroaryl ring, includes, but is not limited to:

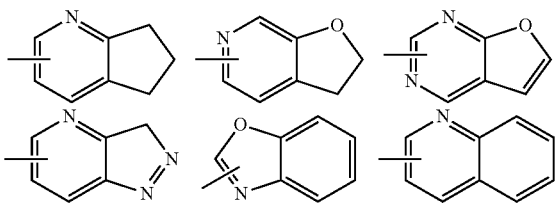

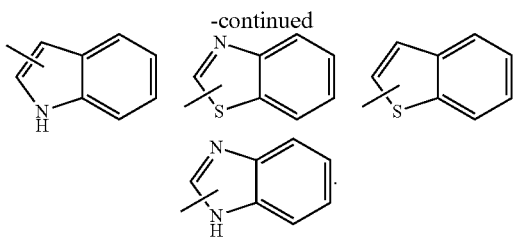

The heteroaryl group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$.

"Alkenyl" refers to an alkyl group as defined above consisting of at least two carbon atoms and at least one carbon-carbon double bond, for example, $C_{2-10}$ alkenyl refers to a straight or branched alkenyl containing 2 to 10 carbons. Alkenyl includes, but is not limited to vinyl, 1-propenyl, 2-propenyl, 1-, 2- or 3-butenyl, and the likes.

The alkenyl group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$.

"Alkynyl" refers to an alkyl group as defined above consisting of at least two carbon atoms and at least one carbon-carbon triple bond, for example, $C_{2-10}$ alkynyl refers to a straight or branched alkynyl containing 2 to 10 carbons. Alkynyl includes, but is not limited to ethynyl, 1-propynyl, 2-propynyl, 1-, 2- or 3-butynyl, and the likes.

The alkynyl group can be optionally substituted or unsubstituted, and when substituted, the substituent is preferably one or more (preferably, 1, 2, 3 or 4) of the following groups, and independently selected from the group consisting of deuterium, halogen, cyano, nitro, azido $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$.

"Alkoxy" refers to $-O$-(alkyl), wherein alkyl is as defined above, for example, "$C_{1-10}$ alkoxy" refers to an alkyloxy containing 1 to 10 carbons. Alkoxy includes, but is not limited to methoxy, ethoxy, propoxy, butoxy, and the likes.

The alkoxy group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{7-10}$ alkenyl, $C_{7-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$.

"Cycloalkyloxy" refers to $-O$-(unsubstituted cycloalkyl), wherein cycloalkyl is as defined above, for example, "C3-10 cycloalkyloxy" refers to a cycloalkyloxy containing 3 to 10 carbon atoms. Cycloalkyloxy includes, but is not limited to, cyclopropyloxy, cyclobutyloxy, cyclopentyloxy, cyclohexyloxy and the likes.

The cycloalkoxy group can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{10}$, $-C_{0-8}-O-R_{20}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$.

"3-10 membered heterocyclyloxy" refers to $-O$-(unsubstituted 3-10 membered heterocyclyl), wherein 3-10 membered heterocyclyl is defined above; 3-10 membered heterocyclyloxy can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-C(O)OR_{20}$, $-C_{0-8}-C(O)R_{21}$, $-C_{0-8}-O-C(O)R_{21}$, $-C_{0-8}-NR_{22}R_{23}$, $-C_{0-8}-C(=NR_{22})R_{21}$, $-C_{0-8}-N(R_{22})-C(NR_{23})R_{21}$, $-C_{0-8}-C(O)NR_{22}R_{23}$ and $-C_{0-8}-N(R_{22})-C(O)R_{21}$.

"$C_{5-10}$ aryloxy" refers to $-O$-(unsubstituted $C_{5-10}$ aryl), wherein $C_{5-10}$ aryl is defined above; $C_{5-10}$ aryloxy can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-C(O)OR_{20}$, $-C_{0-7}-C(O)R_{21}$, $-C_{0-8}-S-O-C(O)R_{21}$, $-C_{0-8}-NR_{22}R_{23}$, $-C_{0-8}-C(=NR_{22})R_{21}$, $-C_{0-8}-N(R_{22})-C(=NR_{23})R_{21}$, $-C_{0-8}-C(O)NR_{22}R_{23}$ and $-C_{0-8}-N(R_{22})-C(O)R_{21}$.

"5-10 membered heteroaryloxy" refers to $-O$-(unsubstituted 5-10 membered heteroaryl), wherein 5-10 membered heteroaryl is defined above; 5-10 membered heteroaryloxy can be optionally substituted or unsubstituted, and when substituted, the substituent is preferably one or more (preferably, 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ cycloalkyl, 3-10 membered heterocyclyl, $C_{5-10}$ aryl, 5-10 membered heteroaryl, =O, $-C_{0-8}-S(O)_rR_{19}$, $-C_{0-8}-O-R_{20}$, $-C_{0-8}-C(O)OR_{20}$, $-C_{0-8}-C(O)R_{21}$, $-C_{0-8}-O-

$C(O)R_{21}$, $—C_{0-8}—NR_{22}R_{23}$, $—C_{0-8}—C(=NR_{22})R_{21}$, $—C_{0-8}—N(R_{22})—C(=NR_{23})R_{21}$, $—C_{0-8}—C(O)NR_{22}R_{23}$ and $—C_{0-8}—N(R_{22})—C(O)R_{21}$, "$C_{1-8}$ alkanoyl" refers to a monovalent atomic group obtained by removing hydroxyl from $C_{1-8}$ alkyl acid, is also generally referred to as "$C_{0-8}—C(O)—$", for example, "$C_1—C(O)—$" refers to acetyl; "$C_2—C(O)—$" refers to propionyl; and "$C_3—C(O)—$" refers to butyryl or isobutyryl.

"$—C_{0-8}—S(O)_rR_{19}$" means that the sulfur atom in $—S(O)_rR_{19}$ is bonded to $C_{0-8}$ alkyl, wherein $C_0$ alkyl means a bond, and $C_{1-8}$ alkyl is as defined above.

"$—C_{0-8}—O—R_{20}$" means that the oxygen atom in $—O—R_{20}$ is bonded to $C_{0-8}$ alkyl, wherein $C_0$ alkyl means a bond, and $C_{1-8}$ alkyl is as defined above.

"$—C_{0-8}—C(O)OR_{20}$" means that the carbonyl group in $—C(O)OR_{20}$ is bonded to $C_{0-8}$ alkyl, wherein $C_0$ alkyl means a bond, and $C_{1-8}$ alkyl is as defined above.

"$—C_{0-8}—C(O)R_{21}$" means that the carbonyl group in $—C(O)R_{21}$ is bonded to $C_{0-8}$ alkyl, wherein $C_0$ alkyl means a bond, and $C_{1-8}$ alkyl is as defined above.

"$—C_{0-8}—O—C(O)R_{21}$" means that the oxygen atom in $—O—C(O)R_{21}$ is bonded to $C_{0-8}$ alkyl, wherein $C_0$ alkyl means a bond, and $C_{1-8}$ alkyl is as defined above.

"$—C_{0-8}—NR_{22}R_{23}$" means that the nitrogen atom in $—NR_{22}R_{23}$ is bonded to $C_{0-8}$ alkyl, wherein $C_0$ alkyl means a bond, and $C_{1-8}$ alkyl is as defined above.

"$—C_{0-8}—C(=NR_{22})R_{21}$" means that the carbonyl in $—C(=NR_{22})R_{21}$ is bonded to $C_{0-8}$ alkyl, wherein $C_0$ alkyl means a bond, and $C_{1-8}$ alkyl is as defined above.

"$—C_{0-8}—N(R_{22})—C(=NR_{23})R_{21}$" means that the carbonyl in $—N(R_{22})—C(=NR_{23})R_{21}$ is bonded to $C_{0-8}$ alkyl, wherein $C_0$ alkyl means a bond, and $C_{1-8}$ alkyl is as defined above.

"$—C_{0-8}—C(O)NR_{22}R_{23}$" means that the carbonyl in $—C(O)NR_{22}R_{23}$ is bonded to $C_{0-8}$ alkyl, wherein $C_0$ alkyl means a bond, and $C_{is}$ alkyl is as defined above.

"$—C_{0-8}—N(R_{22})—C(O)R_{21}$" means that the nitrogen atom in $—N(R_{22})—C(O)R_{21}$ is bonded to $C_{0-8}$ alkyl, wherein $C_0$ alkyl means a bond, and $C_{1-8}$ alkyl is as defined above.

"$C_{1-10}$ haloalkyl" refers to a alkyl group having 1 to 10 carbon atoms, wherein any hydrogen atom on which is optionally substituted with F, Cl, Br or I, and includes, but is not limited to difluoromethyl, dichloromethyl, dibromomethyl, trifluoromethyl, trichloromethyl, tribromomethyl, and the like.

"$C_{1-10}$ haloalkoxy" refers to an alkoxy having 1 to 10 carbon atoms, wherein any hydrogen atom on which is optionally substituted with F, Cl, Br or I, and includes, but is not limited to difluoromethoxy, dichloromethoxy, dibromomethoxy, trifluoromethoxy, trichloromethoxy, tribromomethoxy, and the likes.

"Halogen" refers to F, Cl, Br or I.

"MeOH" refers to methanol. "DMF" refers to N,N-dimethylformamide. "DCE" refers to 1,2-dichloroethane. "TEM" refers to tetrahydrofuran. "PE" refers to petroleum ether. "EA/EtOAc" refers to ethyl acetate. "DCM" refers to dichloromethane. "LiOH" refers to lithium hydroxide. "NaOH" refers to sodium hydroxide. "NaNO$_2$" refers to sodium nitrite. "CuI" refers to cuprous iodide. "Na$_2$SO$_4$" refers to sodium sulfate. "HOAc" refers to acetic acid. "NH$_4$Oac" refers to ammonium acetate. "Et$_3$N" refers to triethylamine. "NH$_4$Cl" refers to ammonium chloride. "TFA" refers to trifluoroacetic acid. "m-CPBA" refers to m-chloroperoxybenzoic acid. "Pd(PPh$_3$)$_4$" refers to tetrakis (triphenylphosphine) palladium. "Pd(PPh$_3$)$_2$Cl$_2$" refers to palladium bis(triphenylphosphine) dichloride.

"Optional" or "optionally" means that the event or environment subsequently described may, but need not, occur, including where the event or environment occurs or does not occur, that is, including both substituted and unsubstituted situations. For example, "heterocyclyl optionally substituted by alkyl" means that an alkyl group may be, but is not necessarily, present, and the description includes the case where the heterocyclyl is substituted with an alkyl and the case where the heterocyclyl is not substituted with an alkyl.

"Substituted" means that one or more hydrogen atoms in a group are each independently substituted with a corresponding number of substituents. It goes without saying that a substituent is only in its possible chemical position, and those skilled in the art will be able to determine (by experiment or theory) possible or impossible substitution without undue efforts. For example, it may be unstable that an amino group or a hydroxyl group having a free hydrogen is attached with a carbon atom having an unsaturated bond (such as an olefin).

"Stereoisomer" refers to an isomer produced due to a different spatial arrangement of atoms in the molecules, and can be classified into either cis-trans isomers and enantiomers, or enantiomers and diastereomers. Stereoisomers resulting from the rotation of a single bond are called conformational stereo-isomers, and sometimes also called rotamers. Stereoisomers induced by reasons such as bond lengths, bond angles, double bonds in molecules and rings are called configuration stereo-isomers, which are classified into two categories. Among them, isomers induced by the double bonds or single bonds of ring-forming carbon atoms that cannot rotate freely are called geometric isomers, also known as cis-trans isomers, which are divided into two configurations including Z and E. For example: cis-2-butene and trans-2-butene are a pair of geometric isomers. Stereoisomers with different optical activities due to the absence of anti-axial symmetry in the molecules are called optical isomers, which are classified into two configurations including R and S. Unless otherwise specified, the "stereoisomer" in the present invention can be understood to include one or several of the above-mentioned enantiomers, configurational isomers and conformational isomers.

"Pharmaceutically acceptable salt" in the present invention refers to pharmaceutically acceptable acid addition salts, including inorganic acid salts and organic acid salts, and these salts can be prepared by methods known in the art.

"Pharmaceutical composition" refers to a mixture comprising one or more of the compounds described herein, or a physiologically/pharmaceutically acceptable salt or prodrug thereof, and other chemical components, for example physiological/pharmaceutically acceptable carriers and excipients. The purpose of the pharmaceutical composition is to promote the administration to an organism, which facilitates the absorption of the active ingredient thereby exerting biological activities.

The present invention will be further described in detail below in conjunction with the embodiments which is not intended to limit the present invention. The present invention is also not limited to the contents of the embodiments.

The structure of the compound of the present invention is determined by nuclear magnetic resonance (NMR) or/and liquid chromatography-mass spectrometry (LC-MS). The NMR chemical shift (δ) is given in parts per million (ppm). The NMR is measured by a Bruker AVANCE-400 nuclear magnetic apparatus, and the solvent is deuterated dimethyl sulfoxide (DMSO-$d_6$), deuterated methanol (CD$_3$OD) and deuterated chloroform (CDCl$_3$), and the internal standard is tetramethylsilane (TMS).

The measurement of LC-MS is performed by using an Agilent 6120 mass spectrometer. The measurement of HPLC is performed by using an Agilent 1200 DAD high pressure liquid chromatograph (Sunfire C18 150×4.6 mm column) and a Waters 2695-2996 high pressure liquid chromatograph (Gimini C18 150×4.6 mm column)

The thin layer chromatography silica gel plate is Yantai Yellow Sea HSGF254 or Qingdao GF254 silica gel plate. The specification of TLC is 0.15 mm-0.20 mm, and the specification for thin layer chromatography separation and purification is 0.4 mm-0.5 mm. 200-300 mesh silica gel (Yantai Huanghai silica gel) as a carrier is generally used in column chromatography.

The starting materials in the examples of the present invention are known and commercially available or can be synthesized according to methods known in the art.

Unless otherwise stated, all reactions of the present invention are carried out under continuous magnetic stirring in a dry nitrogen or argon atmosphere, the solvent is a dry solvent, and the unit of the reaction temperature is degrees Celsius (° C.).

I. Preparation of Intermediates

Preparation of Intermediate 1(R)-1-(3-(pentafluoro-$\lambda^6$-sulfanyl)phenyl)ethan-1-amine

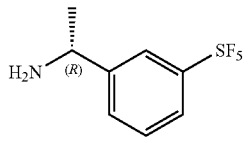

Step 1: Synthesis of (3-(1-ethoxyvinyl)phenyl)pentafluoro-$\lambda^6$-sulfane

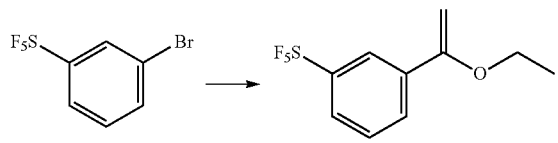

(3-bromophenyl)pentafluoro-$\lambda^6$-sulfane (1.0 g, 3.53 mmol) was dissolved in N,N-dimethylformamide (20 mL), and tributyl(1-ethoxyvinyl)tin (1.4 g, 3.89 mmol) and bis-triphenylphosphine palladium dichloride (248 mg, 0.353 mmol) were added. The reaction solution was heated to 80° C. and stirred for 18 hours. After the reaction was completed, the reaction solution was directly used in the next step of reaction.

Step 2: Synthesis of 1-(3-(pentafluoro-$\lambda^6$-sulfanyl)phenyl)ethan-1-one

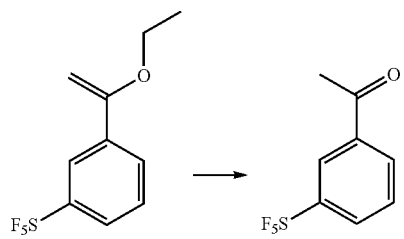

A dioxane hydrochloride solution (4N, 2 mL) was dropwise added to the above reaction solution, which was then stirred at 0° C. for 2 hours. After the reaction is completed, the reaction solution was quenched with a saturated sodium bicarbonate solution, and extracted twice with ethyl acetate. The organic phases were combined, washed with a saturated brine, dried over anhydrous sodium sulfate, concentrated to dryness, and separated by column chromatography [eluent: ethyl acetate/petroleum ether=0-10/]1 to obtain 1-(3-(pentafluoro-$\lambda^6$-sulfanyl)phenyl)ethan-1-one (670 mg, yield: 77%).

Step 3: Synthesis of (R,Z)-2-methyl-N-(1-(3-(pentafluoro-$\lambda^6$-sulfanyl)phenyl)ethylidene)propane-2-sulfinamide

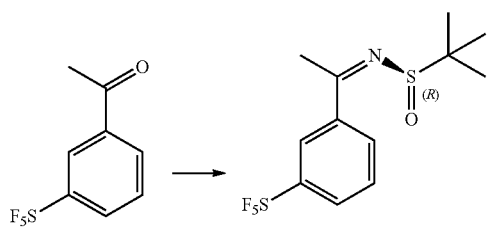

1-(3-(pentafluoro-$\lambda^6$-sulfanyl)phenyl)ethan-1-one (670 mg, 2.72 mmol), (R)-(+)-tert-butylsulfinamide (396 mg, 3.27 mmol), and tetraethyl titanate (3.76 g, 5.44 mmol) were dissolved in tetrahydrofuran (10 mL), then heated to 70° C. and stirred for 2 hours. After the reaction was completed, the reaction solution was diluted with ethyl acetate (150 mL), quenched with saturated sodium bicarbonate solution, and filtered. The filtrate was washed with a saturated brine, dried over anhydrous sodium sulfate, concentrated to dryness, and separated by column chromatography [eluent: ethyl acetate/petroleum ether=0-30%] to obtain (R,Z)-2-methyl-N-(1-(3-(pentafluoro-$\lambda^6$-sulfanyl)phenyl)ethylidene)propane-2-sulfinamide (789 mg, yield: 83%). MS m/z (ESI): 350 [M+H]$^+$.

Step 4: Synthesis of (R)-2-methyl-N—((R)-1-(3-(pentafluoro-λ⁶-sulfanyl)phenyl)ethyl)propane-2-sulfinamide

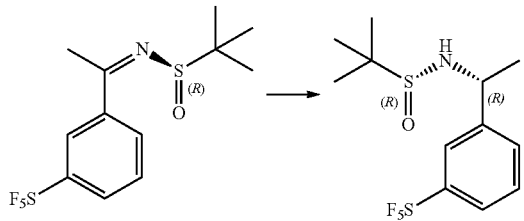

(R,Z)-2-methyl-N-(1-(3-(pentafluoro-λ⁶-sulfanyl)phenyl)ethylidene)propane-2-sulfinamide (400 mg, 1.15 mmol) was dissolved in tetrahydrofuran (10 mL, water content: 20%), and cooled to −50'C. Sodium borohydride (130 mg, 3.44 mmol) was added. The reaction solution was stirred for 1 hour while being held at the current temperature, and then stirred again at room temperature for 1 hour. After the reaction was completed, the reaction solution was diluted with dichloromethane, filtered to remove insoluble substances, dried over anhydrous sodium sulfate, concentrated to dryness, and then separated by column chromatography [eluent: ethyl acetate/petroleum ether=0-80%] to obtain (R)-2-methyl-N—((R)-1-(3-(pentafluoro-λ⁶-sulfanyl)phenyl)ethyl)propane-2-sulfinamide (300 mg, yield: 74%). MS m/z (ESI): 352 [M+H]⁺.

Step 5: Synthesis of (R)-1-(3-(pentafluoro-λ⁶-sulfanyl)phenyl)ethan-1-amine hydrochloride

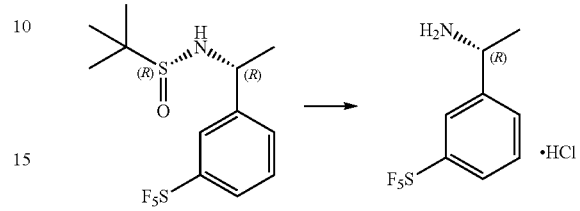

(R)-2-methyl-N—((R)-1-(3-(pentafluoro-λ⁶-sulfanyl)phenyl)ethyl)propane-2-sulfinamide (300 mg, 0.85 mmol) was dissolved in dioxane hydrochloride solution (4N, 5 mL) and stirred overnight at room temperature. After the reaction was completed, the reaction solution was concentrated to dryness to obtain (R)-1-(3-(pentafluoro-λ⁶-sulfanyl)phenyl)ethan-1-amine hydrochloride (270 mg), which was used directly in the next step of reaction. MS m/z (ESI): 248 [M+H]⁺.

Intermediates 2-4 were prepared according to the synthesis method of Intermediate I.

| Intermediate No. | Structural Formula | Chemical Name | MS[M + H]⁺. m/z (ESI): |
|---|---|---|---|
| 2 | ![structure] | (S)-1-(4-(pentafluoro-λ⁶-sulfanyl)phenyl)ethan-1-amine | 248 |
| 3 | ![structure] | (R)-1-(4-(pentafluoro-λ⁶-sulfanyl)phenyl)ethan-1-amine | 248 |
| 4 | ![structure] | (S)-1-(3-(pentafluoro-λ⁶-sulfanyl)phenyl)ethan-1-amine | 248 |

Preparation of Intermediate 5 (S)-1-(2-fluoro-4-(pentafluoro-λ⁶-sulfanyl)phenyl)ethan-1-amine

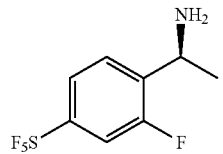

Step 1: Synthesis of 2-fluoro-N-methoxy-N-methyl-4-(pentafluoro-λ⁶-sulfanyl)benzamide

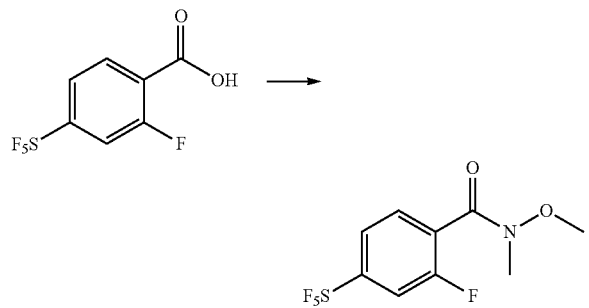

2-fluoro-4-(pentafluoro-λ⁶-sulfanyl)benzoic acid (2 g, 7.6 mmol) was dissolved in N-methylpyrrolidone (10 mL) and then O-(7-azabenzotriazole)-1-YL)-N,N,N,N-tetramethylaldehyde cationic hexafluorophosphate (4.32 g, 11.3 mmol), methoxymethylamine hydrochloride (1.08 g, 11.3 mmol) and triethylamine (1.53 g, 15.2 mmol) were added. The reaction solution was stirred at room temperature for 16 hours. After the reaction was completed, the reaction solution was quenched with water and extracted twice with ethyl acetate.

The organic phases were combined, washed with a saturated brine and dried over anhydrous sodium sulfate. The reaction solution was concentrated to dryness, and then separated by column chromatography [eluent: petroleum ether/ethyl acetate (30%)] to obtain 2-fluoro-N-methoxy-N-methyl-4-(pentafluoro-λ⁶-sulfanyl) benzamide (1.8 g, yield: 76%). MS m/z (ESI): 309.8 [M+H]+.

Step 2: Synthesis of 1-(2-fluoro-4-(pentafluoro-λ⁶-sulfanyl)phenyl)ethane-1-one

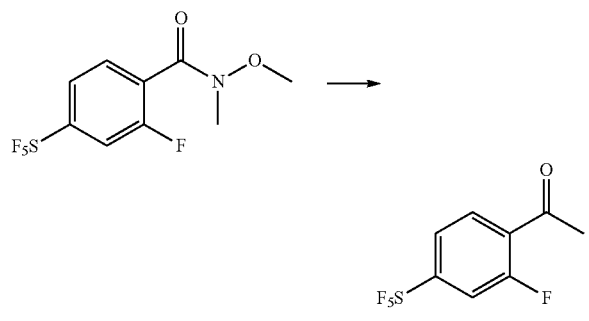

2-fluoro-N-methoxy-N-methyl-4-(pentafluoro-λ⁶-sulfanyl)benzamide (1.8 g, 5.8 mmol) was dissolved in tetrahydrofuran (40 mL). A methylmagnesium bromide solution (12 mL, 12 mmol) was added under an ice bath. The reaction solution was stirred for 1 hour. After the reaction was completed, the reaction solution was quenched with a saturated ammonium chloride solution and extracted twice with ethyl acetate. The organic phases were combined, washed with a saturated brine, and dried over anhydrous sodium sulfate. The reaction solution was concentrated to dryness, and then separated by column chromatography [eluent: petroleum ether-petroleum ether/ethyl acetate (5%)] to obtain 1-(2-fluoro-4-(pentafluoro-λ⁶-sulfanyl)phenyl)ethan-1-one (1.2 g, yield: 78%).

Step 3: Synthesis of (S,E)-N-(1-(2-fluoro-4-(pentafluoro-λ⁶-sulfanyl)phenyl)ethylidene)-2-methylpropane-2-sulfinamide

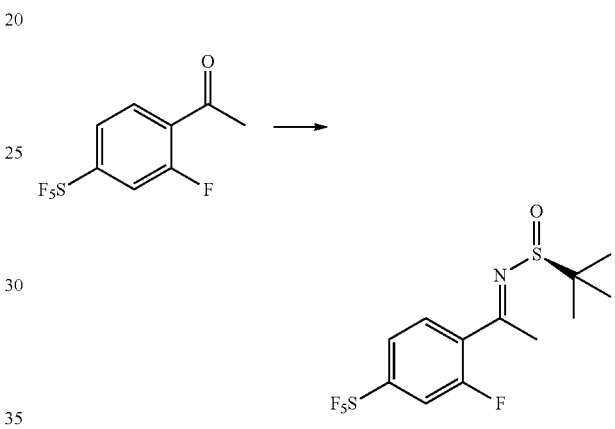

1-(2-fluoro-4-(pentafluoro-λ⁶-sulfanyl)phenyl)ethan-1-one (700 mg, 2.65 mmol), (S)-2-methylpropane-2-sulfinamide (417 mg, 3.44 mmol) and tetraethyl titanate (2 mL) were dissolved in tetrahydrofuran (30 mL), and then heated to 50° C. and stirred for 5 hours. After the reaction was completed, the reaction solution was quenched with a saturated sodium carbonate solution, filtered, and extracted twice with ethyl acetate. The organic phases were combined, washed with a saturated brine, dried over anhydrous sodium sulfate, concentrated to dryness, and separated by column chromatography [eluent: petroleum ether-petroleum ether/ethyl acetate (30%)] to obtain (S,E)-N-(1-(2-fluoro-4-(pentafluoro-λ⁶-sulfanyl)phenyl)ethylidene)-2-methylpropane-2-sulfinamide (700 mg, yield: 72%). MS m/z (ESI): 367 [M+H]⁺.

Step 4: (S)—N—((S)-1-(2-fluoro-4-(pentafluoro-λ⁶-sulfanyl)phenyl)ethyl)-2-methylpropane-2-sulfinamide

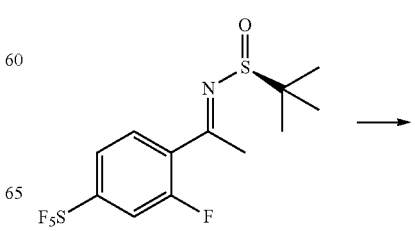

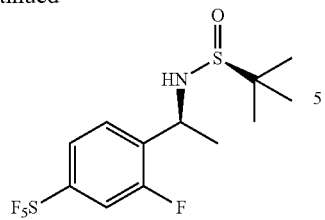

(S,E)-N-(1-(2-fluoro-4-(pentafluoro-λ⁶-sulfanyl)phenyl)ethylidene)-2-methylpropane-2-sulfinamide (700 mg, 1.91 mmol) was dissolved in tetrahydrofuran (20 mL), and cooled to −50° C. Sodium borohydride (195 mg, 5.73 mmol) was added. The reaction solution was stirred for half an hour while being held at the current temperature. After the reaction was completed, the reaction solution was quenched with a saturated brine and extracted twice with ethyl acetate. The organic phases were combined, washed with a saturated brine, dried over anhydrous sodium sulfate, concentrated to dryness, and separated by column chromatography [eluent: petroleum ether-petroleum ether/ethyl acetate (60/6)] to obtain (S)—N—((S)-1-(2-fluoro-4-(pentafluoro-λ⁶-sulfanyl)phenyl)ethyl)-2-methylpropane-2-sulfinamide (700 mg, yield: 99%). MS m/z (ESI): 370 [M+H]⁺.

Step 5: Synthesis of (S)-1-(2-fluoro-4-(pentafluoro-λ⁶-sulfanyl)phenyl)ethan-1-amine

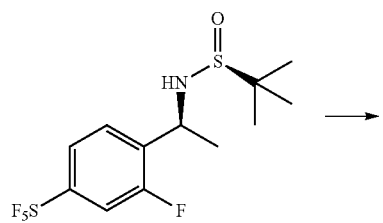

(S)—N—((S)-1-(2-fluoro-4-(pentafluoro-λ⁶-sulfanyl)phenyl)ethyl)-2-methylpropane-2-sulfinamide (700 mg, 1.89 mmol) was dissolved in a dioxane hydrochloride solution (2N, 30 mL), and stirred at room temperature for 4 hours. After the reaction was completed, the reaction solution was concentrated to dryness to obtain (S)-1-(2-fluoro-4-(pentafluoro-λ⁶-sulfanyl)phenyl)ethan-1-amine (600 mg, yield: 95%). MS m/z (ESI): 266 [M+H]⁺.

Preparation of Intermediate 6 (R)-1-(2-fluoro-4-(pentafluoro-λ⁶-sulfanyl)phenyl)ethan-1-amine

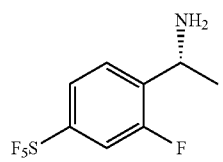

Step 1: Synthesis of (R,E)-N-(1-(2-fluoro-4-(pentafluoro-1'-sulfanyl)phenyl)ethylidene)-2-methylpropane-2-sulfinamide

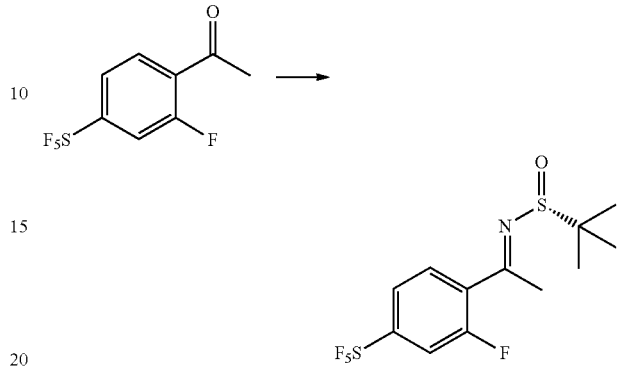

1-(2-fluoro-4-(pentafluoro-λ⁶-sulfanyl)phenyl)ethan-1-one (500 mg, 1.89 mmol), (R)-2-methylpropane-2-sulfinamide (291 mg, 2.46 mmol) and tetraethyl titanate (2 mL) were dissolved in tetrahydrofuran (30 mL), then heated to 50° C. and stirred for 5 hours. After the reaction was completed, the reaction solution was quenched with a saturated sodium carbonate solution, filtered, and extracted twice with ethyl acetate. The organic phases were combined, washed with a saturated brine, dried over anhydrous sodium sulfate, concentrated to dryness, and separated by column chromatography [eluent: petroleum ether-petroleum ether/ethyl acetate (30%)] to obtain (R,E)-N-(1-(2-fluoro-4-(pentafluoro-λ⁶-sulfanyl)phenyl)ethylidene)-2-methylpropane-2-sulfinamide (450 mg, 65% yield). MS m/z (ESI): 368 [M+H]⁺.

Step 2: Synthesis of (R)—N—((R)-1-(2-fluoro-4-(pentafluoro-λ⁶-sulfanyl)phenyl)ethyl)-2-methylpropane-2-sulfinamide

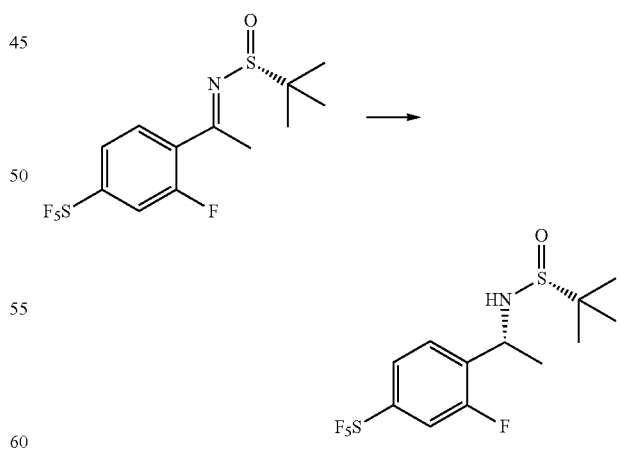

(R,E)-N-(1-(2-fluoro-4-(pentafluoro-λ⁶-sulfanyl)phenyl)ethylidene)-2-methylpropane-2-sulfinamide (450 mg, 1.22 mmol) was dissolved in tetrahydrofuran (20 mL) and cooled to −50° C. Sodium borohydride (125 mg, 3.67 mmol) was added. The mixture stirred for half an hour while being held at the current temperature. After the reaction was completed, the reaction solution was quenched with a saturated brine and extracted twice with ethyl acetate. The organic phases were combined, washed with a saturated brine, dried over anhydrous sodium sulfate, concentrated to dryness, and then separated by column chromatography [eluent: petroleum ether-petroleum ether/ethyl acetate (60%)) to obtain (R)—N—((R)-1-(2-fluoro-4-(pentafluoro-$\lambda^6$-sulfanyl)phenyl)ethyl)-2-methylpropane-2-sulfinamide (380 mg, yield: 84%). MS m/z (ESI): 370 [M+H]$^+$.

Step 3: Synthesis of (R)-1-(2-fluoro-4-(pentafluoro-$\lambda^6$-sulfanyl)phenyl)ethan-1-amine

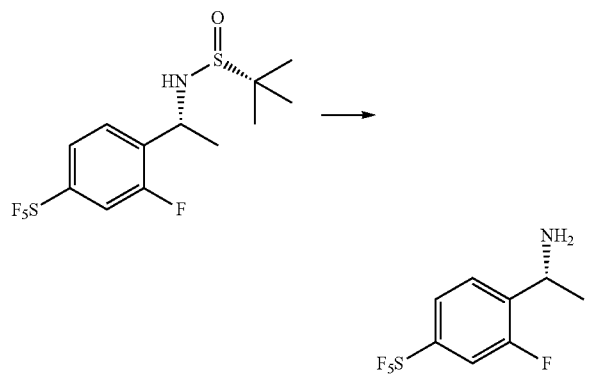

(R)—N—((R)-1-(2-fluoro-4-(pentafluoro-$\lambda^6$-sulfanyl)phenyl)ethyl)-2-methylpropane-2-sulfinamide (380 mg, 1.03 mmol) was dissolved in a dioxane hydrochloride solution (2N, 30 mL), and stirred at room temperature for 4 hours. After the reaction was completed, the reaction solution was concentrated to dryness to obtain (R)-1-(2-fluoro-4-(pentafluoro-$\lambda^6$-sulfanyl)phenyl)ethan-1-amine (300 mg, yield: 96%). MS m/z (ESI): 266 [M+H]$^+$.

Preparation of Intermediate 7 (2-(pentafluoro-$\lambda^6$-sulfanyl)phenyl)methylamine hydrochloride

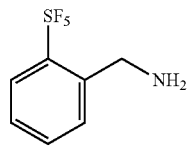

Step 1: Synthesis of (2-(pentafluoro-$\lambda^6$-sulfanyl)phenyl)hydrazine hydrochloride

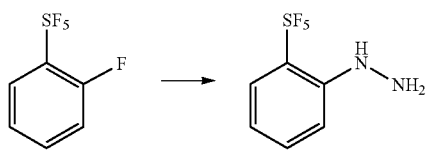

Pentafluoro(2-fluorophenyl)-$\lambda^6$-sulfane (3.0 g, 13.5 mmol) was dissolved in dimethyl sulfoxide (15 mL). Hydrazine hydrate (30 mL) was added. The reaction solution was reacted in a sealed tube at 100° C. for 20 hours. The reaction solution was cooled to room temperature. 1 N aqueous sodium hydroxide solution (150 mL) and saturated water (150 mL) were added. The mixture was extracted with methyl tert-butyl ether (2*100 mL), washed with a saturated brine (3*100 mL), dried over anhydrous sodium sulfate and filtered. The filtrate was added with a dioxane hydrochloride solution (4 N, 5 mL, 20 mmol), stirred at room temperature for 20 minutes, and concentrated to dryness to obtain (2-(pentafluoro-$\lambda^6$-sulfanyl)phenyl)hydrazine hydrochloride (3.5 g, yield: 96%). MS m/z (ESI): 235 [M+H]$^+$.

Step 2: Synthesis of 2-(pentafluoro-$\lambda^6$-sulfanyl)aniline hydrochloride

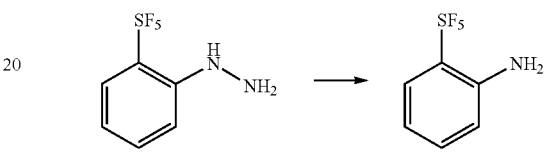

(2-(pentafluoro-$\lambda^6$-sulfanyl)phenyl)hydrazine hydrochloride was dissolved in methanol (50 mL). Raney nickel was added. The reaction solution was stirred overnight at room temperature in the presence of hydrogen. The reaction solution was filtered. The filter cake was washed with methanol (20 mL). The filtrate was added with a dioxane hydrochloride solution (4 N, 5 mL, 20 mmol), stirred at room temperature for 20 minutes, and concentrated to dryness to obtain 2-(pentafluoro-$\lambda^6$-sulfanyl)aniline hydrochloride (3.7 g crude product), which was directly used in the next step of reaction. MS m/z (ESI): 220 [M+H]$^+$.

Step 3: Synthesis of pentafluoro(2-iodophenyl)-$\lambda^6$-sulfane

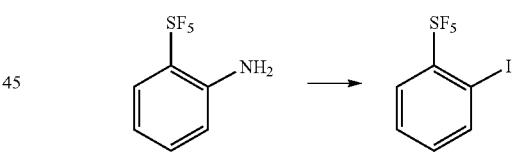

2-(pentafluoro-$\lambda^6$-sulfanyl)aniline hydrochloride (3.7 g crude product) was dissolved in a tetrafluoroboric acid solution (30 mL) and heated to dissolve completely. The reaction solution was cooled to 0° C. (under an ice bath). A sodium nitrite solution (2.0 g, 29 mmol, 10 mL of water) was added dropwise under cooling and stirring in the ice bath, after which the reaction solution was continuously stirred for 30 minutes under stirring in the ice bath. A potassium iodide solution (7.2 g, 43.4 mmol, 15 mL of water) was added slowly, after which the ice bath was removed. The reaction solution was stirred for reaction at room temperature for 30 minutes. The reaction solution was extracted with ethyl acetate (2*100 mL), and washed with a saturated sodium bicarbonate solution and a sodium thiosulfate solution (2*100 mL). The organic phase was concentrated, and the residue was separated by column chromatography [eluent: petroleum ether/ethyl acetate=0-5%] to obtain pentafluoro(2-iodophenyl)-$\lambda^6$-sulfane (3.3 g, two-step yield: 77%).

¹H NMR (400 MHz, Chloroform-d) 8.15 (d, J=7.9 Hz, 1H), 7.81 (dd, J=8.4, 1.5 Hz, 1H), 7.45 (t, J=8.0 Hz, 1H), 7.13 (t, J=7.6 Hz, 1H).

Step 4: Synthesis of 2-(pentafluoro-λ⁶-sulfanyl) benzonitrile

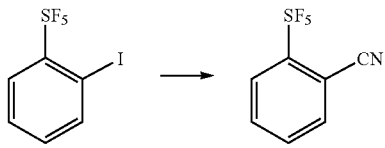

A mixture (12 mL) of pentafluoro(2-iodophenyl)-λ⁶-sulfane (1.85 g, 5.6 mmol) and cuprous cyanide (2.0 g, 22.4 mmol) in N-methylpyrrolidone was reacted under microwave at 100° C. for 2.5 hours. Ethyl acetate (100 mL), concentrated ammonia water (15 mL) and water (100 mL) were added to the reaction solution, which was stirred at room temperature for 10 minutes and then dispensed. The organic layer was washed with a saturated brine (100 mL) and concentrated, and the residue was separated by column chromatography [eluent: petroleum ether/ethyl acetate=0-10%] to obtain 2-(pentafluoro-λ⁶-sulfanyl)benzonitrile (0.94 g, yield: 73%).

¹H NMR (400 MHz, Chloroform-d) δ 7.95 (d, J=8.3 Hz, 1H), 7.86 (d, J=7.6 Hz, 1H), 7.74 (t, J=8.0 Hz, 1H), 7.66 (t, J=7.6 Hz, 1H).

Step 5: Synthesis of (2-(pentafluoro-λ⁶-sulfanyl) phenyl)methylamine hydrochloride

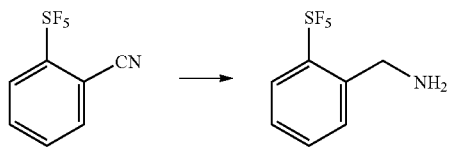

2-(Pentafluoro-λ⁶-sulfanyl)benzonitrile (1.88 g, 8.2 mmol) was dissolved in tetrahydrofuran (5 mL). A borane tetrahydrofuran complex solution (1 N, 50 mL, 50 mmol) was added. The reaction solution was refluxed for reaction for 20 hours. The borane tetrahydrofuran complex solution (1 N, 50 mL, 50 mmol) was replenished, and the reaction solution was continuously refluxed for reaction for 20 hours. The reaction solution was cooled to room temperature, and methanol (30 mL) and a dioxane hydrochloride solution (4 N, 4 mL, 16 mmol) were slowly added, after which the reaction solution was continuously fluxed for reaction 1 hour and then concentrated by rotary evaporation. N-pentane (50 mL) was added to the residue, which was stirred at room temperature for half an hour and filtered with suction. The filter cake was washed with n-pentane (20 mL), and dried to obtain (2-(pentafluoro-λ⁶-sulfanyl)phenyl)methylamine hydrochloride (2.22 g), which was used directly in the next step of reaction. MS m/z (ESI): 234 [M+H]⁺.

Preparation of Intermediate 8
(R)-5-fluoro-2,3-dihydro-1H-inden-1-amine

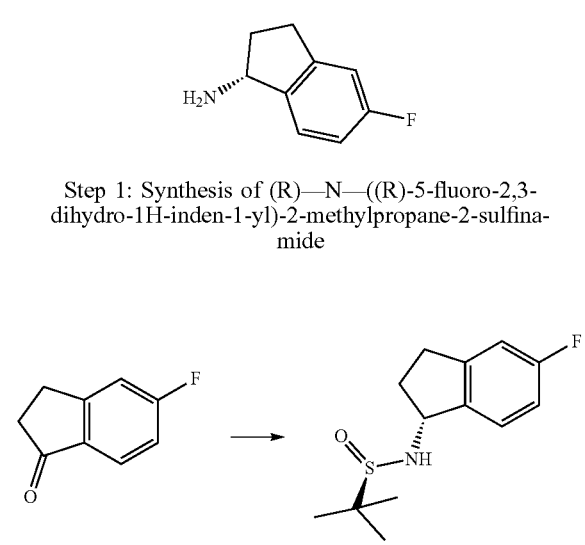

Step 1: Synthesis of (R)—N—((R)-5-fluoro-2,3-dihydro-1H-inden-1-yl)-2-methylpropane-2-sulfinamide 5-fluoro-2,3-dihydro-1H-inden-1-one (5.0 g, 33.3 mmol) was dissolved in anhydrous tetrahydrofuran (100 mL). (R)-2-methylpropane-2-sulfinamide (8.07 g, 66.6 mmol) and tetraisopropyl titanate (37.86 g, 133.2 mmol) were added. The reaction solution was heated to reflux for 24 h under a nitrogen atmosphere. After the reaction was completed, the reaction solution was cooled to 0° C., added with sodium borohydride (5.04 g, 133.2 mmol) in batches, and stirred at 0° C. for 3 hours. After the reaction of the intermediate was complete, a saturated brine was added dropwise to quench the reaction. After the reaction system was filtered, the filtrate was concentrated, and the crude product was separated by silica gel column chromatography [eluent: petroleum ether/ethyl acetate=70/30] to obtain (R)—N—((R)-5-fluoro-2,3-dihydro-1H-inden-1-yl)-2-methylpropane-2-sulfinamide (2.4 g, yield: 28%), with MS m/z (ESI): 256 [M+H]⁺.

Step 2: Synthesis of
(R)-5-fluoro-2,3-dihydro-1H-inden-1-amine

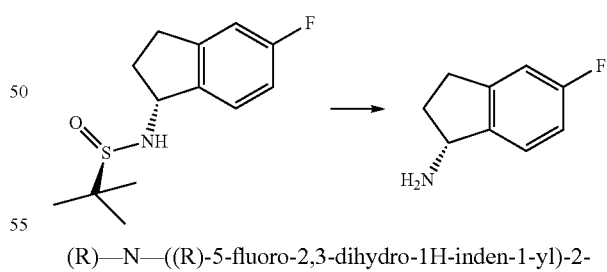

(R)—N—((R)-5-fluoro-2,3-dihydro-1H-inden-1-yl)-2-methylpropane-2-sulfinamide (2.4 g, 9.40 mmol) was dissolved in methanol (10 mL). A methanol hydrochloride solution (4 M, 10 mL) was added under stirring. The reaction solution was continuously stirred at room temperature for 1 hour. After the reaction system was concentrated, water (10 mL) and ethyl acetate (10 mL) were added, and the aqueous phase was separated and lyophilized to obtain (R)-5-fluoro-2,3-dihydro-1H-inden-1-amine hydrochloride (1.6 g, yield: 91%), with MS m/z (ESI): 135 [M+H–NH₃]⁺.

Intermediates 9-12 were prepared according to the synthesis method of Intermediate 8.

| Intermediate No. | Structural Formula | Chemical Name | MS. m/z (ESI): |
|---|---|---|---|
| 9 | | (R)-6-fluoro-2,3-dihydro-1H-inden-1-amine | 150, [M + H − H$_2$]$^+$ |
| 10 | | (R)-5,6-difluoro-2,3-dihydro-1H-inden-1-amine | 153, [M + H − NH$_3$]$^+$ |
| 11 | | (R)-5-chloro-2,3-dihydro-1H-inden-1-amine | 166, [M + H − H$_2$]$^+$ |
| 12 | | (R)-5-trifluoromethyl-2,3-dihydro-1H-inden-1-amine | 185, [M + H − NH$_3$]$^+$ |

Preparation of Intermediate 13
(S)-5-fluoro-2,3-dihydro-1H-inden-1-amine

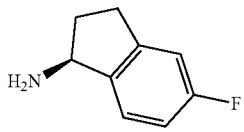 [SMILES: N[C@H]1CCc2cc(F)ccc21]

Step 1: Synthesis of (S)—N—((S)-5-fluoro-2,3-dihydro-1H-inden-1-yl)-2-methylpropane-2-sulfinamide

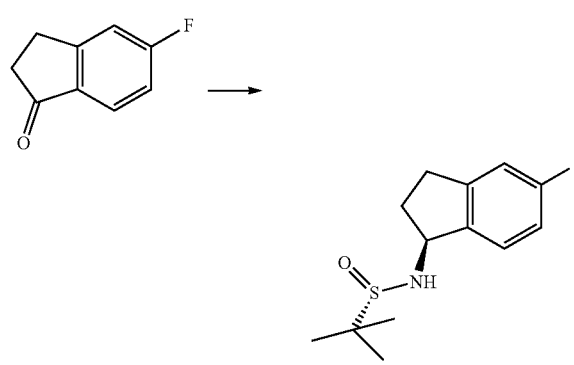

5-fluoro-2,3-dihydro-1H-inden-1-one (5.0 g, 33.3 mmol) was dissolved in anhydrous tetrahydrofuran (100 mL). (S)-2-methylpropane-2-sulfinamide (8.07 g, 66.6 mmol) and tetraisopropyl titanate (37.86 g, 133.2 mmol) were added. The reaction solution was heated to reflux for 24 h under nitrogen atmosphere. After the reaction was completed, the reaction solution was cooled to 0° C., and sodium borohydride (5.04 g, 133.2 mmol) was added in batches. The reaction solution was stirred at 0° C. for 3 hours. After the reaction of the intermediate was complete, a saturated brine was added dropwise to quench the reaction. After the reaction system was filtered, the filtrate was concentrated, and the crude product was separated by silica gel column chromatography [eluent: petroleum ether/ethyl acetate (70/30)] to obtain (S)—N—((S)-5-fluoro-2,3-dihydro-1H-inden-1-yl)-2-methylpropane-2-sulfinamide (2.4 g, yield: 28%), with MS m/z (ESI): 256 [M+H]$^+$.

Step 2: Synthesis of
(S)-5-fluoro-2,3-dihydro-1H-inden-1-amine

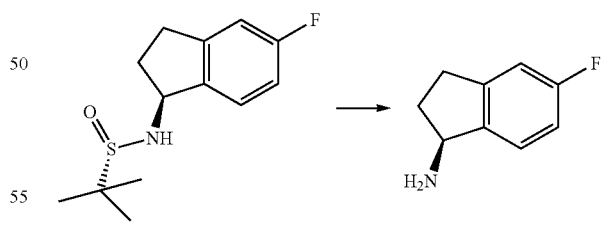

(S)—N—((S)-5-fluoro-2,3-dihydro-1H-inden-1-yl)-2-methylpropane-2-sulfinamide (2.4 g, 9.40 mmol) was dissolved in methanol (10 mL). A methanol hydrochloride solution (4 M, 10 mL) was added under stirring. The reaction solution was continuously stirred for 1 hour at room temperature. After the reaction system was concentrated, water (10 mL) and ethyl acetate (10 mL) were added, and the aqueous phase was separated and lyophilized to obtain (S)-5-fluoro-2,3-dihydro-1H-inden-1-amine hydrochloride (1.5 g, yield: 85%), with MS m/z (ESI): 135 [M+H−NH$_3$]$^+$.

Intermediates 14-17 were Prepared According to the Synthesis Method of Intermediate 13

| Intermediate No. | Structural Formula | Chemical Name | MS, m/z (ESI): |
|---|---|---|---|
| 14 | | (S)-6-fluoro-2,3-dihydro-1H-inden-1-amine | 150, $[M + H - H_2]^+$ |
| 15 | | (S)-5,6-difluoro-2,3-dihydro-1H-inden-1-amine | 153, $[M + H - NH_3]^+$ |
| 16 | | (S)-5-chloro-2,3-dihydro-1H-inden-1-amine | 166, $[M + H - H_2]^+$ |
| 17 | | (S)-5-trifluoromethyl-2,3-dihydro-1H-inden-1-amine | 185, $[M + H - NH_3]^+$ |

Preparation of Intermediate 18
(R)—N-methyl-2,3-dihydro-1H-inden-1-amine

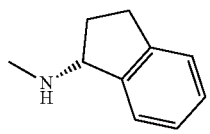

Step 1: Synthesis of
(R)—N-Boc-2,3-dihydro-1H-inden-1-amine

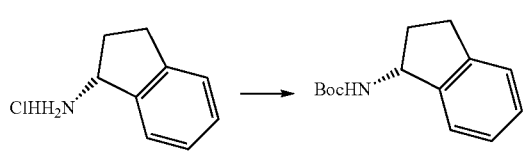

(R)-2,3-dihydro-1H-inden-1-amine hydrochloride (1.0 g, 5.89 mmol) was dissolved in tetrahydrofuran (15 mL). Triethylamine (1.79 g, 17.68 mmol) and Boc anhydride (1.42 g, 6.48 mmol) were added. The reaction was successively stirred overnight at room temperature. After the reaction was completed, the reaction system was directly concentrated, and the crude product was separated by column chromatography [eluent: ethyl acetate/petroleum ether (5/95)] to obtain (R)—N-Boc-2,3-dihydro-1H-inden-1-amine (1.38 g, yield: 100%).

Step 2: Synthesis of tert-butyl (R)-(2,3-dihydro-1H-inden-1-yl)(methyl)carbamate

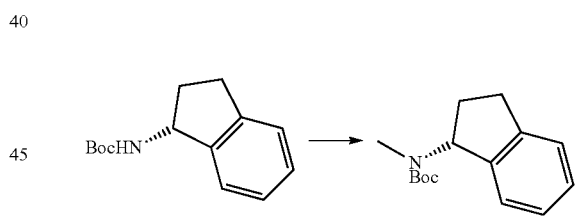

(R)—N-Boc-2,3-dihydro-1H-inden-1-amine (1.38 g, 5.89 mmol) was dissolved in anhydrous N,N-dimethylformamide (8 mL). Sodium hydride (60%, 355 mg, 8.87 mmol) was added at 0° C. After the reaction was stirred at 0° C. for 30 minutes, iodomethane (2.52 g, 17.74 mmol) was added, and the reaction solution was heated to room temperature and continuously stirred for three hours. The reaction was quenched with water (50 mL), and the reaction solution was extracted with ethyl acetate (50 mL*3). The organic phases were combined, washed with water, dried and concentrated. The crude product was separated by column chromatography [eluent: ethyl acetate/petroleum ether (10/90)] to obtain tert-butyl (R)-(2,3-dihydro-1H-inden-1-yl)(methyl)carbamate (1.3 g, yield: 89%).

Step 3: Synthesis of (R)—N-methyl-2,3-dihydro-1H-inden-1-amine

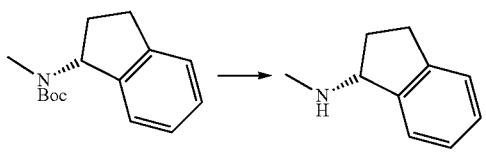

Tert-butyl(R)-(2,3-dihydro-1H-inden-1-yl)(methyl)carbamate (1.3 g, 5.26 mmol) was dissolved in acetonitrile (10 mL). Concentrated hydrochloric acid (5 mL) was added. The reaction solution was stirred at room temperature for three hours and then underwent pressure reduction to remove most of the acetonitrile. The aqueous phase was lyophilized to obtain (R)—N-methyl-2,3-dihydro-1H-inden-1-amine (950 mg, yield: 98%), with MS m/z (ESI): 148 [M+H]$^+$.

Intermediate 19 was Prepared According to the Synthesis Method of Intermediate 18

| Intermediate No. | Structural Formula | Chemical Name | MS, m/z (ESI): |
|---|---|---|---|
| 19 | | (S)-N-methyl-2,3-dihydro-1H-inden-1-amine | 148, [M + H]$^+$ |

Preparation of Intermediate 20 7-((3aR,4R,6aS)-4-(tert-butoxymethyl)-2,2-dimethyl-3a, 6a-dihydro-4H-cyclopenta[d][1,3]dioxol-6-yl)-2,4-dichloropyrrolo[2,1-f][1,2,4]triazine

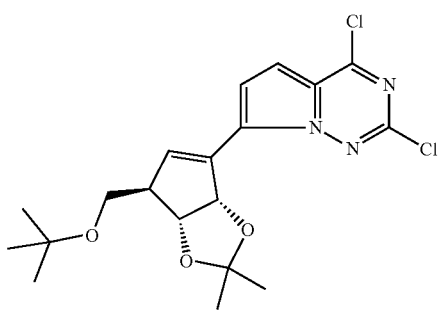

Step 1: Synthesis of (3aR,6R,6aR)-6-(tert-butoxymethyl)-2,2-dimethyltetrahydro-4H-cyclopenta[d][1,3]dioxol-4-one

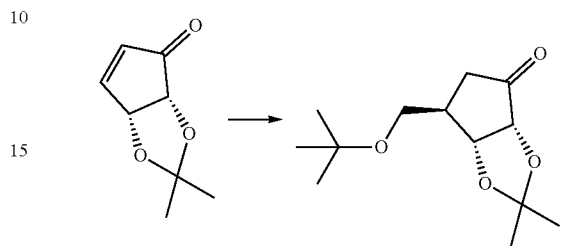

Sec-butyllithium (74.6 mL, 97 mmol) was added dropwise to potassium tert-butoxide (10.9 g, 97 mmol) in a methyl tert-butyl ether solution (400 mL) at −70° C. under the protection of nitrogen. After the reaction solution was stirred for 3 hours at −70° C. lithium bromide (16.82 g, 190 mmol) in a tetrahydrofuran solution (100 mL) was added. The reaction solution was heated to the temperature of −15° C. and stirred for 30 minutes. The temperature of the reaction solution was decreased to −70° C. again, and a cuprous bromide dimethylsulfide complex (9.98 g, 48 mmol) in a diisopropyl sulfide solution (70 mL) was added. The reaction solution was stirred for minutes, and then, (3aR,6aR)-2,2-dimethyl-3a,6a-dihydro-4H-cyclopenta[d][1,3]dioxol-4-one (5 g, 32 mmol) in a tetrahydrofuran solution (50 mL) was added. The reaction solution was heated to the temperature of −30° C. and stirred for 30 minutes. After the reaction was completed, a mixed solution (50 mL) of methanol and acetic acid (1:1) was used for quenching, a mixed solution of ammonium chloride and 3% ammonia water (1:1) was poured in. The water layer was removed. The organic layer was washed with a mixed solution of a saturated ammonium chloride solution and 3% ammonia water (1:1) and a brine water, dried over anhydrous sodium sulfate, concentrated and then separated by column chromatography [eluent: petroleum ether-petroleum ether/ethyl acetate (15%)] to obtain (3aR,6R,6aR)-6-(tert-butoxymethyl)-2,2-dimethyltetrahydro-4H-cyclopenta[d][1,3]dioxol-4-one (6.8 g, yield: 85%).

Step 2: Synthesis of (3aR,6R,6aR)-6-(tert-butoxymethyl)-4-(2,4-dichloropyrrolo[2,1-f][1,2,4]triazin-7-yl)-2,2-dimethyltetrahydro-4H-cyclopenta[d][1,3]dioxol-4-ol

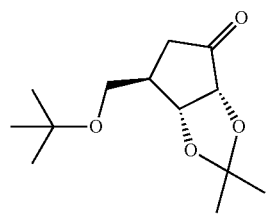

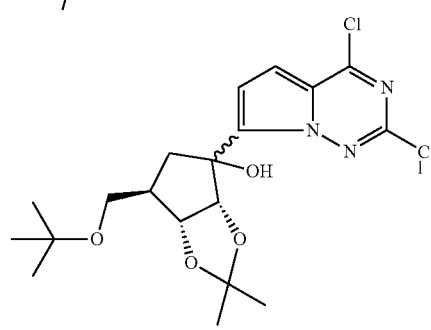

N-butyllithium (22.8 mL, 56.9 mmol) was added dropwise to 2,4-dichloro-7-iodopyrrolo[2,1-f][1,2,4]triazine (13.7 g, 43.8 mmol) in a tetrahydrofuran (300 mL) at −70° C. under the protection of nitrogen. After the reaction solution was stirred at −70° C. for 2 hours, (3aR,6R,6aR)-6-(tert-butoxymethyl)-2,2-dimethyltetrahydro-4H-cyclopenta[d][1,3]dioxol-4-one (10.6 g, 43.8 mmol) in a tetrahydrofuran solution (40 mL) was added, and the reaction solution was continuously stirred at −70° C. for 1 hour. After the reaction was complete d, a saturated ammonium chloride solution was used for quenching. The reaction solution was extracted with ethyl acetate, and the organic layer was concentrated and then separated by column chromatography [eluent: petroleum ether-petroleum ether/ethyl acetate (15%)] to obtain (3aR,6R,6aR)-6-(tert-butoxymethyl)-4-(2,4-dichloropyrrolo[2,1-f][1,2,4]triazin-7-yl)-2,2-dimethyltetrahydro-4H-cyclopenta[d][1,3]dioxol-4-ol (12 g, yield: 64%). MS m/z (ESI): 430 [M+H]+.

Step 3: Synthesis of 7-((3aR,4R,6aS)-4-(tert-butoxymethyl)-2,2-dimethyl-3a,6a-dihydro-4H-cyclonta[d][1,3]dioxol-6-yl)-2,4-dichloropyrrolo[2,1-f][1,2,4]triazine

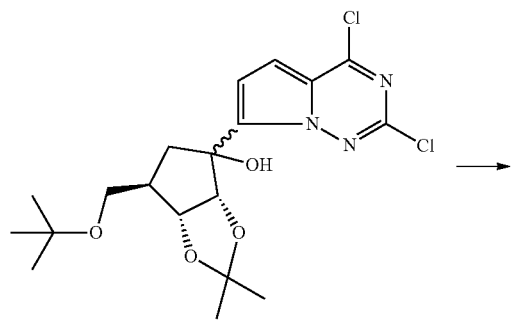

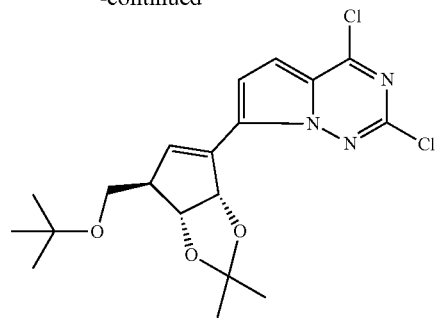

A Burgess reagent (14.3 g, 56 mmol) was added to (3aR,6R,6aR)-6-(tert-butoxymethyl)-4-(2,4-dichloropyrrolo[2,1-f][1,2,4]triazin-7-yl)-2,2-dimeth yltetrahydro-4H-cyclopenta[d][1,3]dioxol-4-ol (12 g, 28 mmol) in a tetrahydrofuran solution (200 mL), which was then heated to 50° C. and stirred for 4 hours. After the reaction was completed, the reaction solution was concentrated to dryness and separated by column chromatography [petroleum ether-petroleum ether/ethyl acetate (15%)] to obtain 7-((3aR,4R,6aS)-4-(tert-butoxymethyl)-2,2-dimethyl-3a,6a-dihydro-4H-cyclopenta[d][1,3]dioxo 1-6-yl)-2,4-dichloropyrrolo[2,1-f][1,2,4]triazine (7 g, yield: 61%). MS m/z (ESI):412 [M+H]+.

Preparation of Intermediate 21 (2R,3R,4R,5R)-2-(acetoxymethyl)-5-(4,6-dichloro-1H-pyrazolo[3,4-b]pyridin-1-yl)tetrahydrofuran-3,4-diyl diacetate

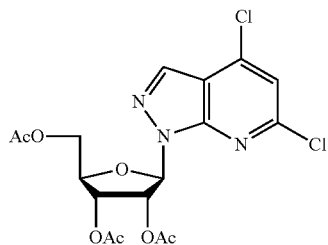

Step 1: Synthesis of ethyl 5-amino-1-(4-methoxybenzyl)-1H-pyrazole-4-carboxylate

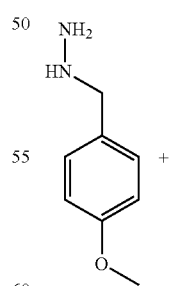

+

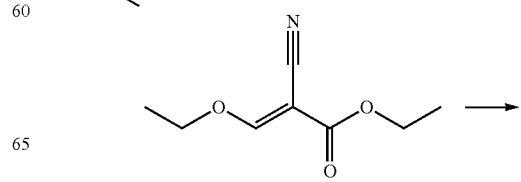

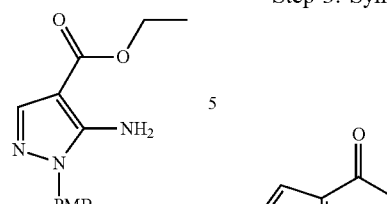

(4-methoxybenzyl)hydrazine hydrochloride (100.0 g, 0.53 mol) was dissolved in absolute ethanol (1.6 L), and triethylamine (81.0 g, 0.80 mol) was added. The reaction solution was stirred at room temperature for 30 minutes, and ethyl (ethoxymethylene)cyanoacetate (98.0 g, 0.58 mol) was added. The reaction mixture was stirred under reflux overnight, and concentrated to remove ethanol. Water (500 mL) was added to the solid residue, which was then extracted with ethyl acetate (2*500 mL). The organic phases were combined, washed with a saturated brine (300 mL), dried with anhydrous sodium sulfate, and filtered with suction. The filtrate was concentrated to obtain ethyl 5-amino-1-(4-methoxybenzyl)-1H-pyrazole-4-carboxylate (135.0 g, yield: 92%). MS m/z (ESI): 276 [M+H]$^+$.

Step 2: Synthesis of ethyl 1-(4-methoxybenzyl)-4,6-dioxo-4,5,6,7-tetrahydro-1H-pyrazolo[3,4-b]pyridin-5-carboxylate

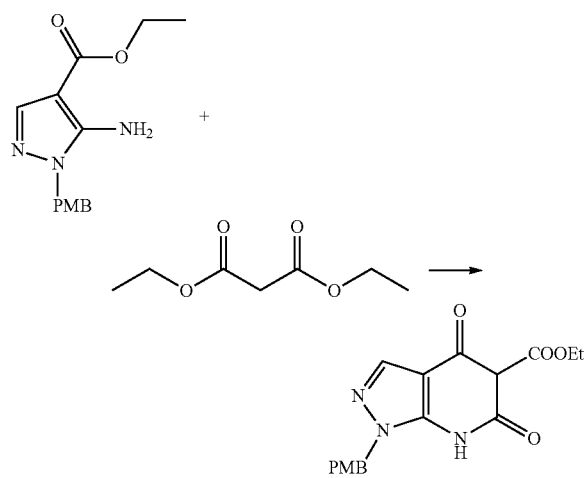

Sodium ethoxide (84.0 g, 1.24 mmol) was dissolved in ethanol (600 mL) and cooled to 0° C. (in an ice bath). Diethyl malonate (198 g, 1.24 mol) was added, and the ice bath was removed. The reaction solution was stirred at room temperature for 20 minutes. Ethyl 5-amino-1-(4-methoxybenzyl)-1H-pyrazole-4-carboxylate (85 g, 0.31 mol) was added, and the reaction mixture was stirred under reflux for 4 days. The reaction mixture was concentrated under reduced pressure to remove ethanol. The residue was added with water (1.5 L) and neutralized to pH −5 with acetic acid. The resulting white solid was filtered off with suction, washed with water (500 mL), and dried under vacuum to obtain ethyl 1-(4-methoxybenzyl)-4,6-dioxo-4,5,6,7-tetrahydro-1H-pyrazolo[3,4-b]pyridin-5-carboxylate (100.8 g, yield: 95%). MS m/z (ESI): 344 [M+H]$^+$.

Step 3: Synthesis of 1-(4-methoxybenzyl)-1H-pyrazolo[3,4-b]pyridin-4,6-diol

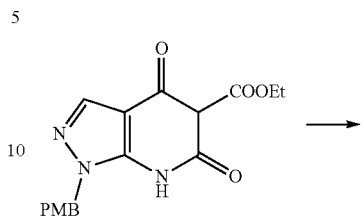

Ethyl 1-(4-methoxybenzyl)-4,6-dioxo-4,5,6,7-tetrahydro-1H-pyrazolo[3,4-b]pyridin-5-carboxylate (100.8 g, 0.29 mol) was dissolved in 25% NaOH aqueous solution (700 mL) and reacted under reflux for 15 hours. The reaction solution was cooled to 0° C., diluted with water (1 L), and slowly neutralized to pH −5 with acetic acid. The resulting white solid was filtered off with suction, and washed with water (1 L). The filter cake was dried under vacuum to obtain 1-(4-methoxybenzyl)-1H-pyrazolo[3,4-b]pyridin-4,6-diol (78.0 g, yield: 98%). MS m/z (ESI): 272 [M+H]$^+$.

Step 4: Synthesis of 4,6-dichloro-1-(4-methoxybenzyl)-1H-pyrazolo[3,4-b]pyridine

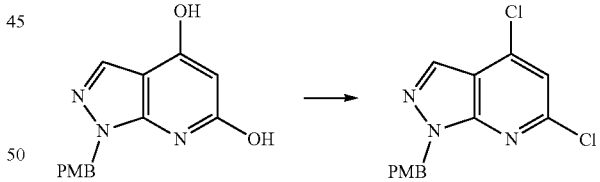

1-(4-methoxybenzyl)-1H-pyrazolo[3,4-b]pyridin-4,6-diol (30.0 g, 110 mmol) and phen ylphosphonic dichloride (62.7 mL, 442 mmol) was stirred at 170° C. to react for 7 hours. The reaction solution was cooled to room temperature, and diluted with dichloromethane (200 mL). The resulting mixed solution was slowly poured into an ice-water mixture that was under vigorous stirring, neutralized to PH −7 with concentrated ammonia water, extracted with dichloromethane (2*300 mL), dried with anhydrous sodium sulfate, and filtered. The filtrate was concentrated. Column chromatography [petroleum ether/ethyl acetate=0-8%] was performed on the residue to obtain 4,6-dichloro-1-(4-methoxybenzyl)-1H-pyrazolo[3,4-b]pyridine (18.3 g, yield: 53%). MS m/z (ESI): 308/310 [M+H]$^+$.

Step 5: Synthesis of 4,6-dichloro-1H-pyrazolo[3,4-b]pyridine

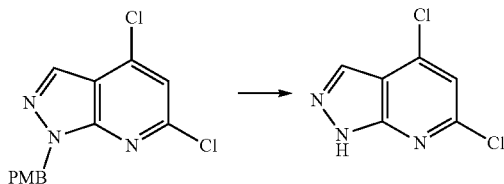

4,6-dichloro-1-(4-methoxybenzyl)-1H-pyrazolo[3,4-b]pyridine (28.0 g, 90.9 mmol) was dissolved in trifluoroacetic acid (84 mL), and stirred at 60° C. to react for 17 hours. The reaction solution was concentrated, the residue was diluted with ethyl acetate (500 mL) and washed with a saturated sodium bicarbonate solution (200 mL), and the organic phase was dried over anhydrous sodium sulfate and filtered with suction. The filtrate was concentrated, and the residue was separated by column chromatography [eluent: petroleum ether/ethyl acetate=0-8%] to obtain 4,6-dichloro-1H-pyrazolo[3,4-b]pyridine (15.3 g, yield: 90/). MS m/z (ESI): 188/190 $[M+H]^+$.

Step 6: Synthesis of (2R,3R,4R,5R)-2-(acetoxymethyl)-5-(4,6-dichloro-1H-pyrazolo[3,4-b]pyridin-1-yl)tetrahydrofuran-3,4-diyl diacetate

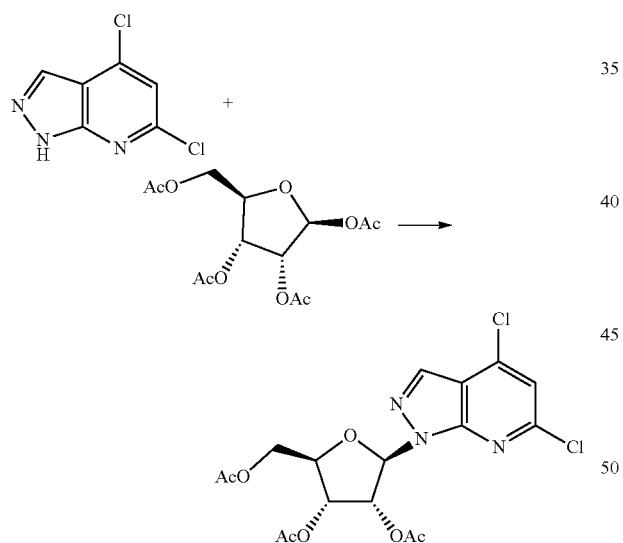

4,6-dichloro-1H-pyrazolo[3,4-b]pyridine (3.0 g, 16.0 mmol) was dissolved in hexamethyldisilazane (30 mL). Ammonium sulfate (421 mg, 3.2 mmol) was added. The reaction solution was stirred at 150° C. to react for 3.5 hours, and underwent rotary evaporation under reduced pressure to remove hexamethyldisilazane. The residue was dissolved in acetonitrile (60 mL), and (2S,3R,4R,5R)-5-(acetoxymethyl)tetrahydrofuran-2,3,4-triyltriacetate (5.59 g, 17.6 mmol) was added. The reaction solution was cooled to 0° C. (in an ice bath), and trimethylsilyl trifluoromethanesulfonate (4.33 mL, 24.0 mmol) was slowly added dropwise, after which, the reaction solution was slowly heated to room temperature and stirred overnight. The reaction solution was concentrated under reduced pressure, and the residue was added with ethyl acetate (150 mL) and washed with a saturated sodium bicarbonate solution (150 mL) for dispensing. The aqueous phase was extracted with ethyl acetate (2*100 mL). The organic phases were combined, dried over anhydrous sodium sulfate, and filtered with suction. The filtrate was concentrated, and the residue was subjected to column chromatography [eluent: petroleum ether/ethyl acetate=0-15%] to obtain (2R,3R,4R,5R)-2-(acetoxymethyl)-5-(4,6-dichloro-1H-pyrazolo[3,4-b]pyridin-1-yl)tetrahydro furan-3,4-diyl diacetate (4.98 g, yield: 70%). MS m/z (ESI): 446/448 $[M+H]^+$.

Preparation of Intermediate 22 (2R,3R,4R,5R)-2-(acetoxymethyl)-5-(4,6-dichloro-1H-pyrazolo[3,4-d]pyrimidin-1-yl)tetrahydrofuran-3,4-diyl diacetate

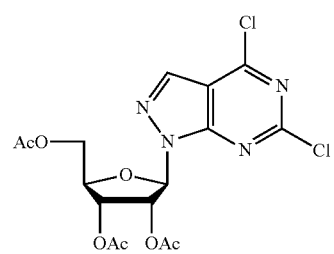

Step 1: Synthesis of (2R,3R,4R,5R)-2-(acetoxymethyl)-5-(4,6-dichloro-1H-pyrazolo[3,4-d]pyrimidin-1-yl)tetrahydrofuran-3,4-diyl diacetate

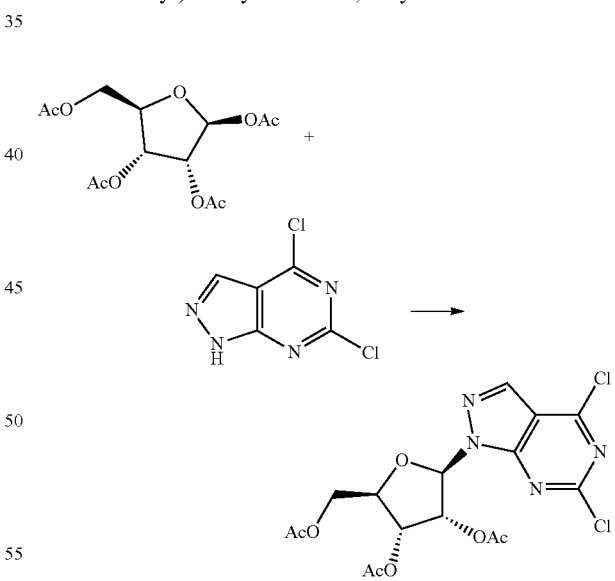

4,6-dichloro-1H-pyrazolo[3,4-d]pyrimidin (2.5 g, 13.2 mmol) was dissolved in hexamethyldisilamine (15 mL). Ammonium sulfate (20 mg, 0.15 mmol) at a catalytic amount was added. Then, the reaction solution was heated to reflux (at 135° C.) for 3 hours. Then, the reaction solution was spun to dryness. Acetonitrile (30 mL) and (2S,3R,4R,5R)-5-(acetoxymethyl)tetrahydrofuran-2,3,4-triyltriacetate (5.06 g, 15.9 mmol) was added. The reaction solution was cooled to 0° C. Trimethylsilyl trifluoromethanesulfonate (2.7 mL) was added. Then, the reaction solution was heated to room temperature and stirred for 24 hours. After the reaction was completed, a saturated brine was used for quenching. The reaction solution was extracted twice with ethyl acetate. The organic phases were combined, washed with a saturated brine, dried over anhydrous sodium sulfate, concentrated, and subjected to column chromatography to obtain (2R,3R,4R,5R)-2-(acetoxymethyl)-5-(4,6-dichloro-1H-pyrazolo[3,4-d]pyrimidin-1-yl)tetrahydro furan-3,4-diyl diacetate (5.0 g, 84%). MS m/z (ESI): 447 [M+H]+.

II. Preparation of Compounds of Specific Examples

Example 1 Preparation of (((((2R,3S,4R,5R)-5-(6-chloro-4-(((R)-1-(4-(pentafluoro-λ6-sulfanyl)phenyl)ethyl)amino)-1H-pyrazolo[3,4-d]pyrimidin-1-yl)-3,4-dihydroxytetrahydrofuran-2-yl)methoxy)(hydroxy)phosphoryl)methyl)phosphonic acid Step 1: Synthesis of (2R,3R,4R,5R)-2-(acetoxymethyl)-5-(6-chloro-4-(((R)-1-(4-(pentafluoro-λ6-sulfanyl)phenyl)ethyl)amino)-1H-pyrazolo[3,4-d]pyrimidin-1-yl)tetrahydrofuran-3,4-diyl diacetate (2R,3R,4R,5R)-2-(acetoxymethyl)-5-(4,6-dichloro-1H-pyrazolo[3,4-d]pyrimidin-1-yl)tetra hydrofuran-3,4-diyl-diacetate (200 mg, 0.55 mmol) and (R)-1-(4-(pentafluoro-λ6-sulfanyl)phenyl)ethan-1-amine (140 mg, 0.46 mmol) were dissolved in tetrahydrofuran (5 mL). Then. N,N-diisopropylethylamine (217 mg, 1.68 mmol) was added. The reaction solution was heated to 60° C. and stirred for 2 hours. After the reaction was completed, the reaction solution was concentrated to dryness to obtain (2R,3R,4R,5R)-2-(acetoxymethyl)-5-(6-chloro-4-(((R)-1-(4-(pentafluoro-λ6-sulfanyl)phenyl)eth yl)amino)-1H-pyrazolo[3,4-d]pyrimidin-1-yl)tetrahydrofuran-3,4-diyl diacetate, which was directly used in the next step of reaction. MS m/z (ESI): 658 [M+H]+.

Step 2: Synthesis of (2R,3R,4S,5R)-2-(6-chloro-4-(((R)-1-(4-(pentafluoro-λ6-sulfanyl)phenyl)ethyl)amino)-1H-pyrazolo[3,4-d]pyrimidin-1-yl)-5-(hydroxymethyl)tetrahydrofuran-3,4-diol

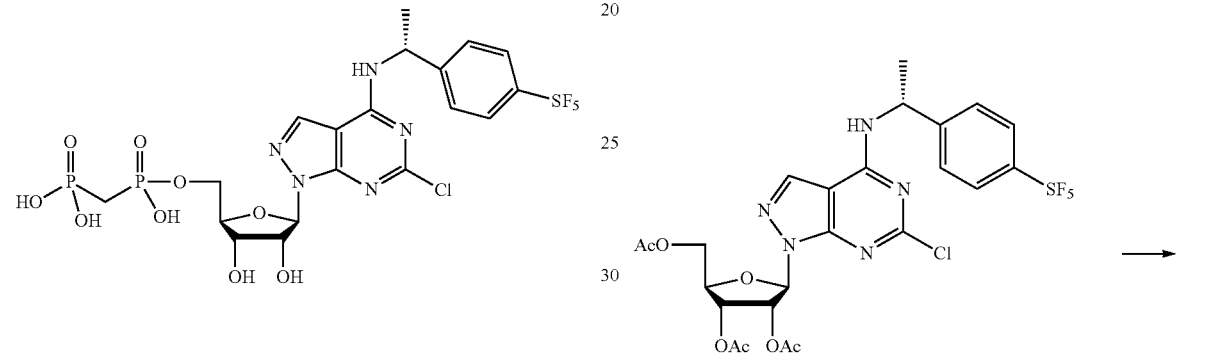

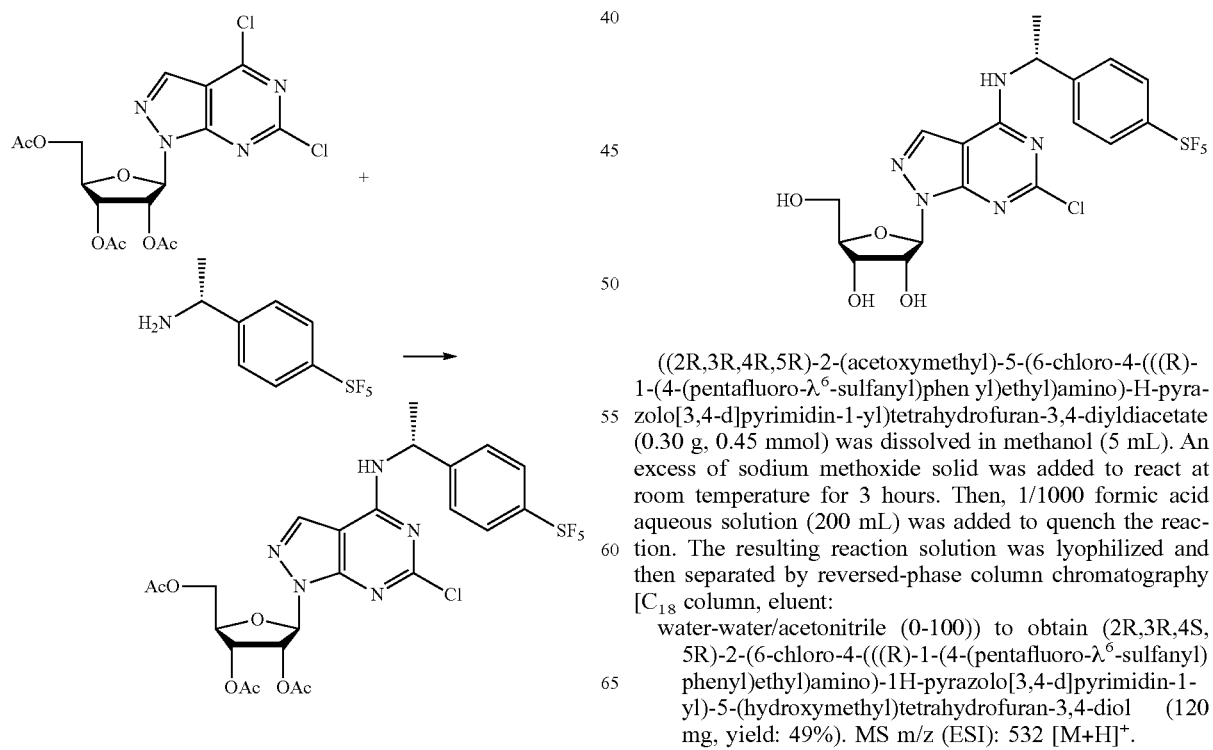

((2R,3R,4R,5R)-2-(acetoxymethyl)-5-(6-chloro-4-(((R)-1-(4-(pentafluoro-λ6-sulfanyl)phen yl)ethyl)amino)-H-pyrazolo[3,4-d]pyrimidin-1-yl)tetrahydrofuran-3,4-diyldiacetate (0.30 g, 0.45 mmol) was dissolved in methanol (5 mL). An excess of sodium methoxide solid was added to react at room temperature for 3 hours. Then, 1/1000 formic acid aqueous solution (200 mL) was added to quench the reaction. The resulting reaction solution was lyophilized and then separated by reversed-phase column chromatography [C18 column, eluent:
water-water/acetonitrile (0-100)) to obtain (2R,3R,4S,5R)-2-(6-chloro-4-(((R)-1-(4-(pentafluoro-λ6-sulfanyl)phenyl)ethyl)amino)-1H-pyrazolo[3,4-d]pyrimidin-1-yl)-5-(hydroxymethyl)tetrahydrofuran-3,4-diol (120 mg, yield: 49%). MS m/z (ESI): 532 [M+H]+.

Step 3: Synthesis of (((((2R,3S,4R,5R)-5-(6-chloro-4-(((R)-1-(4-(pentafluoro-λ⁶-sulfanyl)phenyl)ethyl)amino)-1H-pyrazolo[3,4-d]pyrimidin-1-yl)-3,4-dihydroxytetrahydrofuran-2-yl) methoxy)(hydroxy)phosphol)methyl)phosphonic acid

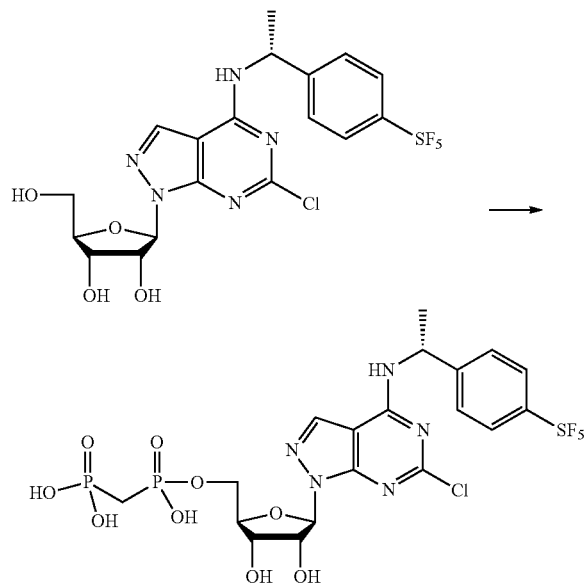

(2R,3R,4S,5R)-2-(6-chloro-4-(((R)-1-(4-(pentafluoro-λ⁶-sulfanyl)phenyl)ethyl)amino)-1H-pyrazolo[3,4-d]pyrimidin-1-yl)-5-(hydroxymethyl)tetrahydrofuran-3,4-diol (60 mg, 0.12 mmol) was dissolved in trimethyl phosphate (2.5 mL). Methylene phosphonium bischloride (112 mg, 0.48 mmol) in a trimethyl phosphate solution (0.5 mL) was added dropwise at 0° C., after which the temperature was held to react for 3 hours. A small quantity of ice was added to quench the reaction. Then, the reaction solution was separated by reversed-phase column chromatography [CIs column, eluent: water-water/acetonitrile (5:1)] to obtain (((((2R,3S,4R,5R)-5-(6-chloro-4-(((R)-1-(4-(pentafluoro-λ⁶-sulfanyl)phenyl)ethyl)amino)-1H-pyrazolo[3,4-d]pyrimidin-1-yl)-3,4-dihydroxytetrahydrofuran-2-yl)methoxy)(hydroxy)phosphoryl)methyl)phosphonic acid (30 mg, yield: 18%). MS mi/z (ESI): 690 [M+H]⁺.

¹H NMR (400 MHz, D₂O) δ 8.14 (s, 11H), 7.81-7.60 (mi, 2H), 7.57-7.35 (m, 2H), 6.21-5.88 (in, 1H), 5.44-5.16 (m, 1H), 4.99-4.76 (m, 1H), 4.54-4.40 (m, 1H), 4.26-4.11 (m, 1H), 4.02-3.83 (m, 2H), 2.13 (t, J=20.1 Hz, 2H), 1.73-1.30 (mi, 31H).

The compounds of Examples 2-4 were prepared according to the synthesis method of Example 1:

| Examples | Structural Formula | Name | [M + H]⁺ |
| --- | --- | --- | --- |
| 2 |  | (((((2R,3S,4R,5R)-5-(6-chloro-4-(((S)-1-(4-(pentafluoro-λ⁶-sulfanyl)phenyl)ethyl)amino)-1H-pyrazolo[3,4-d]pyrimidin-1-yl)-3,4-dihydroxytetrahydrofuran-2-yl)methoxy)(hydroxy)phosphoryl)methyl)phosphonic acid | 690 |
| 3 |  | (((((2R,3S,4R,5R)-5-(6-chloro-4-(((R)-1-(2-fluoro-4-(pentafluoro-λ⁶-sulfanyl)phenyl)ethyl)amino)-1H-pyrazolo[3,4-d]pyrimidin-1-yl)-3,4-dihydroxytetrahydrofuran-2-yl)methoxy)(hydroxy)phosphoryl)methyl)phosphonic acid | 708 |

-continued

| Examples | Structural Formula | Name | [M + H]+ |
|---|---|---|---|
| 4 | | (((((2R,3S,4R,5R)-5-(6-chloro-4-(((S)-1-(2-fluoro-4-(pentafluoro-λ⁶-sulfanyl)phenyl)ethyl)amino)-1H-pyrazolo[3,4-d]pyrimidin-1-yl)-3,4-dihydroxytetrahydrofuran-2-yl)methoxy)(hydroxy)phosphoryl)methyl)phosphonic acid | 708 |

The nuclear magnetic resonance data of the compounds prepared in the examples above are as follows:

| Examples | NMR |
|---|---|
| 2 | ¹HNMR (400 MHz, DMSO-$d_6$ + $D_2O$) δ 8.32 (s, 1H), 7.87 (d, J = 8.4 Hz, 2H), 7.61 (d, J = 8.4 Hz, 2H), 6.02 (d, J = 4.3 Hz, 1H), 5.44 (q, J = 6.9 Hz, 1H), 4.51 (t, J = 4.1 Hz, 1H), 4.28 (t, J = 4.8 Hz, 1H), 4.09 (dp, J = 13.2, 5.0 Hz, 1H), 3.91 (dt, J = 12.9, 6.2 Hz, 2H), 2.21 (t, J = 20.1 Hz, 2H), 1.56 (d, J = 7.0 Hz, 3H). |
| 3 | ¹HNMR (400 MHz, DMSO-$d_6$ + $D_2O$) δ 8.33 (s, 1H), 7.90 (d, J = 10.8 Hz, 1H), 7.73 (d, J = 8.0 Hz, 1H), 7.66-7.64 (m, 1H), 6.00 (s, 1H), 5.56-5.54 (m, 1H), 4.56-4.53 (m, 1H), 4.28-4.26 (m, 1H), 4.04-4.02 (m, 2H), 3.83-3.80 (m, 1H), 2.08 (t, J = 18.6 Hz, 2H), 1.56 (d, J = 5.2 Hz, 3H). |
| 4 | ¹H NMR (400 MHz, DMSO-$d_6$ + $D_2O$) δ 8.40 (s, 1H), 7.97 (d, J = 10.4 Hz, 1H), 7.82 (d, J = 8.4 Hz, 1H), 7.73-7.69 (m, 1H), 6.09 (d, J = 4.4 Hz, 1H), 5.63-5.63 (m, 1H), 4.58-4.56 (m, 1H), 4.34-4.33 (m, 1H), 4.14-4.12 (m, 2H), 3.97-3.96 (m, 1H), 2.24 (t, J = 20.0 Hz, 2H), 1.64 (d, J = 7.6 Hz, 3H). |

Example 5 Preparation of (((((2R,3S,4R,5R)-5-(6-chloro-4-(((S)-1-(2-fluoro-4-(pentafluoro-2-sulfanyl)phenyl)ethyl)amino)-1H-pyrazolo[3,4-b]pyridin-1-yl)-3,4-dihydroxy tetrahydrofuran-2-yl)methoxy)(hydroxy)phosphoryl)methyl)phosphonic acid Step 1: Synthesis of (2R,3R,4R,5R)-2-(acetoxymethyl)-5-(6-chloro-4-(((S)-1-(2-fluoro-4-(pentafluoro-λ⁶-sulfanyl)phenyl)ethyl)amino)-1H-pyrazolo[3,4-b]pyridin-1-yl)tetrahydrofuran-3,4-diyl diacetate

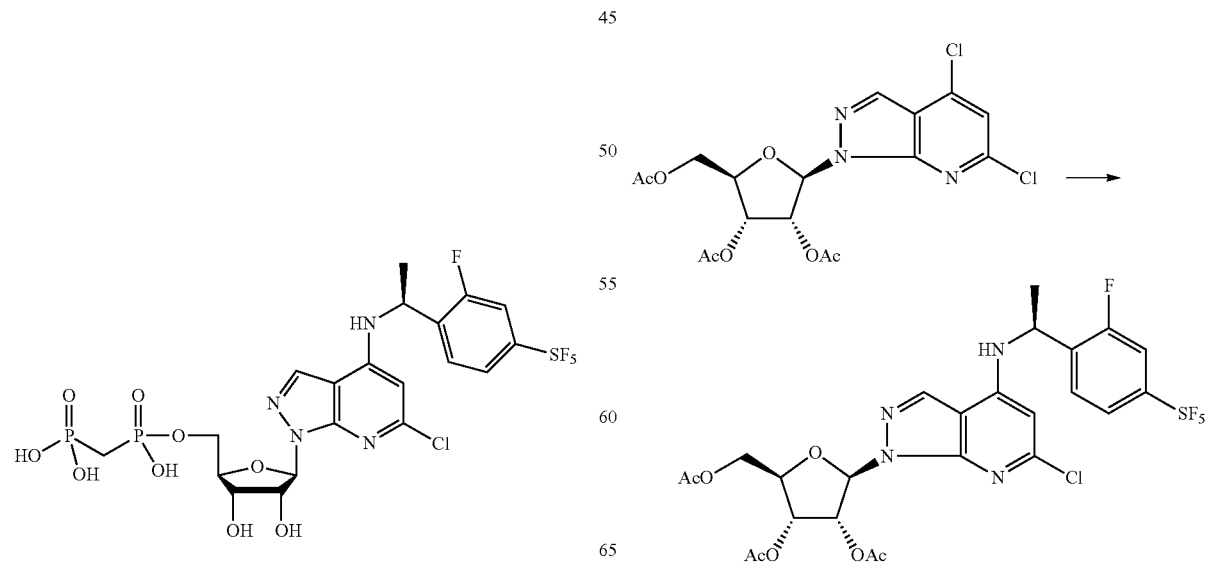

(2R,3R,4R,5R)-2-(acetoxymethyl)-5-(4,6-dichloro-1H-pyrazolo[3,4-b]pyridin-1-yl)tetrahydrofuran-3,4-diyl diacetate (730 mg, 1.65 mmol) and (S)-1-(2-fluoro-4-(pentafluoro-λ⁶-sulfanyl)phenyl)ethan-1-amine (600 mg, 1.98 mmol) were dissolved in N-methylpyrrolidone (15 mL), and then N,N-diisopropylethylamine (608 mg, 4.95 mmol) was added. The reaction solution was heated to 90° C. and stirred for 40 hours. After the reaction was completed, the reaction solution was diluted with water and extracted with ethyl acetate. The organic phases were combined, concentrated and separated by column chromatography [eluent: petroleum ether-petroleum ether/ethyl acetate (40%)] to obtain (2R,3R,4R,5R)-2-(acetoxymethyl)-5-(6-chloro-4-(((S)-1-(2-fluoro-4-(pentafluoro-λ⁶-sulfanyl)phenyl)ethyl)amino)-1H-pyrazolo[3,4-b]pyridin-1-yl)tetrahydrofuran-3,4-diyl diacetate (360 mg, yield: 32%). MS m/z (ESI): 675 [M+H]⁺.

Step 2: Synthesis of (2R,3R,4S,5R)-2-(6-chloro-4-(((S)-1-(2-fluoro-4-(pentafluoro-λ⁶-sulfanyl)phenyl)ethyl)amino)-1H-pyrazolo[3,4-b]pyridin-1-yl)-5-(hydroxymethyl)tetrahydrofuran-3,4-diol

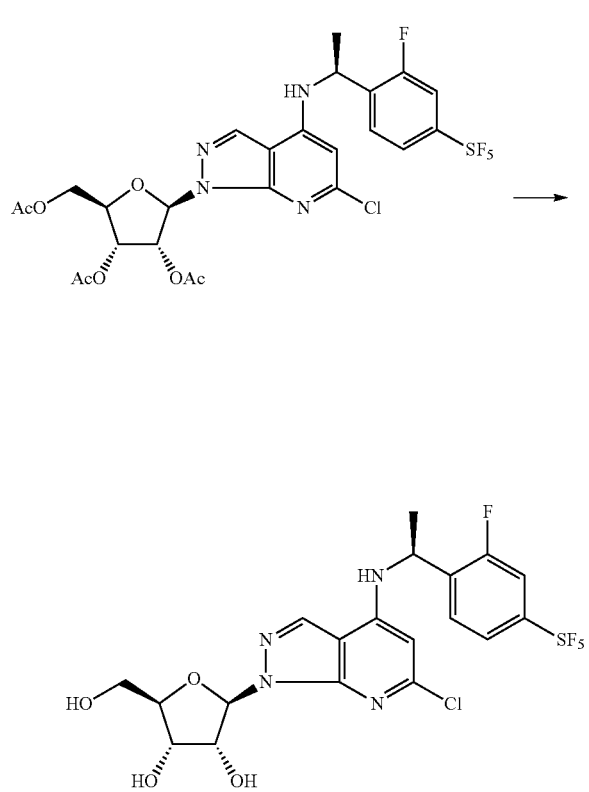

(2R,3R,4R,5R)-2-(acetoxymethyl)-5-(6-chloro-4-(((S)-1-(2-fluoro-4-(pentafluoro-λ⁶-sulfanyl)phenyl)ethyl)amino)-1H-pyrazolo[3,4-b]pyridin-1-yl)tetrahydrofuran-3,4-diyl diacetate (0.32 g, 0.48 mmol) was dissolved in methanol (20 mL). Potassium carbonate (0.19 g, 1.44 mmol) was added to react at room temperature for 1 hour. Then, 1/1000 of formic acid aqueous solution (200 mL) was added to quench the reaction. The resulting reaction solution was lyophilized and then separated by reversed-phase column chromatography [C₁₈ column, eluent: water-water/acetonitrile (0-70%)] to obtain (2R,3R,4S,5R)-2-(6-chloro-4-(((S)-1-(2-fluoro-4-(pentafluoro-λ⁶-sulfanyl)phenyl)ethyl)amino)-1H-pyrazolo[3,4-b]pyridin-1-yl)-5-(hydroxymethyl)tetrahydrofuran-3,4-diol (240 mg, yield: 91%). MS m/z (ESI): 549 [M+H]⁺.

Step 3: Synthesis of (((((2R,3S,4R,5R)-5-(6-chloro-4-(((S)-1-(2-fluoro-4-(pentafluoro-λ⁶-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid

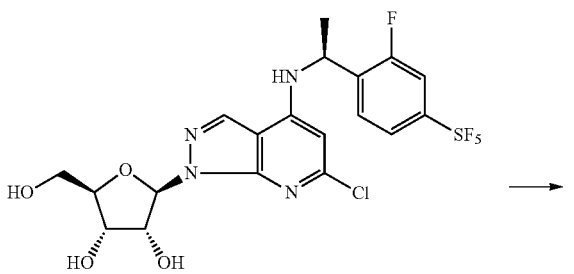

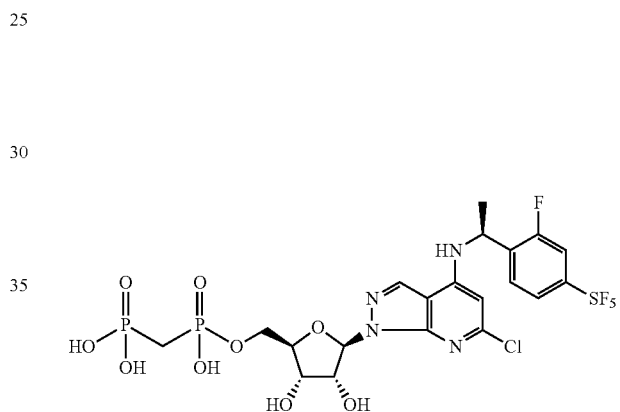

(2R,3R,4S,5R)-2-(6-chloro-4-(((S)-1-(2-fluoro-4-(pentafluoro-λ⁶-sulfanyl)phenyl)ethyl)amino)-1H-pyrazolo[3,4-b]pyridin-1-yl)-5-(hydroxymethyl)tetrahydrofuran-3,4-diol (240 mg, 0.44 mmol) was dissolved in trimethyl phosphate (3 mL). Methylene phosphonium bischloride (436 mg, 1.75 mmol) in a trimethyl phosphate solution (0.5 mL) was added dropwise at 0° C., after which the temperature was held to react for 3 hours. A small quantity of ice was added to quench the reaction. Then, the reaction solution was separated by reversed-phase column chromatography [C₁₈ column, eluent: water-water/acetonitrile (5:1)] to obtain (((((2R,3S,4R,5R)-5-(6-chloro-4-(((S)-1-(2-fluoro-4-(pentafluoro-λ⁶-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid (90 mg, yield: 29%). MS m/z (ESI): 707 [M+H]⁺.

¹H NMR (400 MHz, DMSO-d₆+D₂O) δ 8.38 (s, 1H), 7.96 (dd, J=10.4, 1.6 Hz, 1H), 7.76 (dd, J=8.4, 1.6 Hz, 1H), 7.62 (t, J=8.0 Hz, 1H), 6.08 (d, J=4.4 Hz, 1H), 6.03 (s, 1H), 5.15-5.13 (m, 1H), 4.53 (t, J=4.8 Hz, 1H), 4.26 (t, J=4.0 Hz, 1H), 4.04-4.02 (m, 2H), 3.86-3.83 (m, 1H), 2.12 (t, J=20.0 Hz, 2H), 1.59 (d, J=6.8 Hz, 3H).

The compounds of Examples 6-22 were prepared according to the synthesis method of Example 5:

| Examples | Structural Formula | Name | [M + H]+ |
|---|---|---|---|
| 6 | | (((((2R,3S,4R,5R)-5-(6-chloro-4-(((S)-1-(4-(pentafluoro-λ6-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 689 |
| 7 | | (((((2R,3S,4R,5R)-5-(6-chloro-4-(((R)-1-(4-(pentafluoro-λ6-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 689 |
| 8 | | (((((2R,3S,4R,5R)-5-(6-chloro-4-(((S)-1-(3-(pentafluoro-λ6-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 689 |
| 9 | | (((((2R,3S,4R,5R)-5-(6-chloro-4-(((R)-1-(3-(pentafluoro-λ6-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 689 |

| Examples | Structural Formula | Name | [M + H]⁺ |
| --- | --- | --- | --- |
| 10 | | (((((2R,3S,4R,5R)-5-(6-chloro-4-((2-(pentafluoro-$\lambda^6$-sulfanyl)phenylmethyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 675 |
| 11 | | (((((2R,3S,4R,5R)-5-(6-chloro-4-(((R)-1-(2-fluoro-4-(pentafluoro-$\lambda^6$-sulfanyl)phenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 707 |
| 12 | | (((((2R,3S,4R,5R)-5-(6-chloro-4-(((S)-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 575 |
| 13 | | (((((2R,3S,4R,5R)-5-(6-chloro-4-(((R)-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 575 |

-continued

| Examples | Structural Formula | Name | [M + H]+ |
|---|---|---|---|
| 14 | | (((((2R,3S,4R,5R)-5-(6-chloro-4-(((S)-2,3-dihydro-1H-inden-1-yl)(methyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 589 |
| 15 | | (((((2R,3S,4R,5R)-5-(6-chloro-4-(((R)-2,3-dihydro-1H-inden-1-yl)(methyl)amino)-1H-pyrazolo[3,4-b]pyridin-1-yl)-3,4-dihydroxytetrahydrofuran-2-yl)methoxy)(hydroxy)phosphoryl)methyl)phosphonic acid | 589 |
| 16 | | (((((2R,3S,4R,5R)-5-(6-chloro-4-(((R)-5-fluoro-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 593 |
| 17 | | (((((2R,3S,4R,5R)-5-(6-chloro-4-(((R)-6-fluoro-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 593 |

-continued

| Examples | Structural Formula | Name | [M + H]⁺ |
| --- | --- | --- | --- |
| 18 | | (((((2R,3S,4R,5R)-5-(6-chloro-4-(((R)-5-chloro-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 609 |
| 19 | | (((((2R,3S,4R,5R)-5-(6-chloro-4-(((R)-5-(trifluoromethyl)-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 643 |
| 20 | | (((((2R,3S,4R,5R)-5-(6-chloro-4-(((R)-6-(trifluoromethyl)-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 643 |
| 21 | | (((((2R,3S,4R,5R)-5-(6-chloro-4-(((R)-5,7-difluoro-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 611 |

| Examples | Structural Formula | Name | [M + H]⁺ |
|---|---|---|---|
| 22 | | (((((2R,3S,4R,5R)-5-(6-chloro-4-(((R)-5,6-difluoro-2,3-dihydro-1H-inden-1-yl)amino)-1H-pyrazolo[3,4-b]pyridin-1-yl)-3,4-dihydroxytetrahydrofuran-2-yl)methoxy)(hydroxy)phosphoryl)methyl)phosphonic acid | 611 |

The nuclear magnetic resonance data of the compounds prepared in the examples above are as follows:

| Examples | NMR |
|---|---|
| 6 | $^1$H NMR (400 MHz, D$_2$O) δ 8.21 (s, 1H), 7.76-7.65 (m, 2H), 7.54-7.43 (m, 2H), 6.16 (d, J = 5.5 Hz, 1H), 6.04 (d, J = 8.0 Hz, 1H), 4.88-4.83 (m, 2H), 4.49 (t, J = 4.7 Hz, 1H), 4.22 (q, J = 4.5 Hz, 1H), 3.96 (t, J = 5.3 Hz, 2H), 2.06 (t, J = 19.9 Hz, 2H), 1.53 (t, J = 6.2 Hz, 3H). |
| 7 | $^1$H NMR (400 MHz, Methanol-d$_4$) δ 8.23 (s, 1H), 7.80 (d, 2H), 7.58 (d, J = 8.4 Hz, 2H), 6.28 (d, J = 3.9 Hz, 1H), 6.02 (s, 1H), 4.99-4.89 (m, 1H), 4.74 (t, J = 4.6 Hz, 1H), 4.58 (t, J = 4.9 Hz, 1H), 4.18 (d, J = 6.0 Hz, 2H), 4.15-4.03 (m, 1H), 2.30 (td, J = 20.3, 3.1 Hz, 2H), 1.63 (d, J = 6.8 Hz, 3H). |
| 8 | $^1$H NMR (400 MHz, Methanol-d$_4$) δ 8.25 (s, 1H), 7.88 (t, J = 1.9 Hz, 1H), 7.72 (d, J = 8.3 Hz, 1H), 7.66 (d, J = 7.8 Hz, 1H), 7.54 (t, J = 8.0 Hz, 1H), 6.28 (d, J = 4.0 Hz, 1H), 6.03 (s, 1H), 4.96-4.88 (m, 1H), 4.78-4.73 (m, 1H), 4.64-4.55 (m, 1H), 4.20 (q, J = 5.2 Hz, 1H), 4.14-4.01 (m, 2H), 2.21 (t, J = 19.0 Hz, 2H), 1.64 (d, J = 6.8 Hz, 3H). |
| 9 | $^1$H NMR (400 MHz, Methanol-d$_4$) δ 8.24 (s, 1H), 7.88 (s, 1H), 7.72 (d, J = 7.5 Hz, 1H), 7.65 (d, J = 7.8 Hz, 1H), 7.54 (t, J = 8.0 Hz, 1H), 6.28 (d, J = 3.5 Hz, 1H), 6.07 (s, 1H), 4.70 (s, 1H), 4.56 (s, 1H), 4.29 (s, 1H), 4.20 (s, 2H), 2.68 (s, 1H), 2.42 (t, J = 21.0 Hz, 2H), 1.64 (d, J = 6.8 Hz, 3H). |
| 10 | $^1$H NMR (400 MHz, Methanol-d$_4$) δ 8.06 (s, 1H), 7.86 (d, J = 8.3 Hz, 1H), 7.53 (d, J = 7.8 Hz, 1H), 7.46 (t, J = 7.5 Hz, 1H), 7.40 (t, J = 7.9 Hz, 1H), 6.22 (d, J = 3.6 Hz, 1H), 5.91 (s, 1H), 4.80 (s, 2H), 4.63 (t, J = 4.6 Hz, 1H), 4.49 (t, J = 5.3 Hz, 1H), 4.20-4.02 (m, 3H), 2.29 (s, J = 20.8 Hz, 2H). |
| 11 | $^1$H NMR (400 MHz, DMSO-d$_6$ + D$_2$O) δ 8.38 (s, 1H), 7.96 (d, J = 10.4, 1H), 7.75 (d, J = 8.4 Hz, 1H), 7.64-7.60 (m, 1H), 6.07 (d, J = 4.4 Hz, 1H), 6.03-6.00 (m, 1H), 5.14 (s, 1H), 4.58-4.57 (m, 1H), 4.27-4.25 (m, 1H), 3.98 (d, J = 4.4 Hz, 1H), 3.88-3.87 (m, 1H), 3.76-3.74 (m, 1H), 1.93 (t, J = 19.2 Hz, 2H), 1.58 (d, J = 6.4 Hz, 3H). |
| 12 | $^1$H NMR (400 MHz, Methanol-d$_4$) δ 8.17 (s, 1H), 7.35-7.15 (m, 4H), 6.49 (s, 1H), 6.31 (d, J = 3.8 Hz, 1H), 5.30 (s, 1H), 4.72 (t, J = 4.6 Hz, 1H), 4.57 (t, J = 5.0 Hz, 1H), 4.28-4.17 (m, 2H), 4.16-4.07 (m, 1H), 3.15-3.03 (m, 1H), 3.03-2.90 (m, 1H), 2.73-2.57 (m, 1H), 2.35 (t, J = 20.6 Hz, 2H), 2.04 (dq, J = 15.0, 7.8 Hz, 1H). |
| 13 | $^1$H NMR (400 MHz, Methanol-d$_4$) δ 8.17 (s, 1H), 7.39-7.09 (m, 4H), 6.49 (s, 1H), 6.31 (d, J = 3.7 Hz, 1H), 5.30 (s, 1H), 4.71 (s, 1H), 4.57 (s, 1H), 4.31-4.38 (m, 2H), 4.18-4.08 (m, 1H), 3.15-3.03 (m, 1H), 3.03-2.87 (m, 1H), 2.73-2.57 (m, 1H), 2.38 (t, J = 20.6 Hz, 2H), 2.03 (m, 1H) |
| 14 | $^1$H NMR (400 MHz, Methanol-d$_4$) δ 8.24 (s, 1H), 7.39-7.12 (m, 4H), 6.50 (s, 1H), 6.36 (s, 1H), 5.91 (s, 1H), 4.76 (s, 1H), 4.63 (s, 1H), 4.21 (s, 1H), 4.08 (s, 2H), 3.14-3.01 (m, 2H), 2.94 (s, 3H), 2.65 (s, 1H), 2.26-2.04 (m, 3H). |
| 15 | $^1$H NMR (400 MHz, Methanol-d$_4$) δ 8.24 (s, 1H), 7.35-7.13 (m, 4H), 6.50 (s, 1H), 6.36 (d, J = 3.8 Hz, 1H), 5.91 (t, J = 7.8 Hz, 1H), 4.74 (t, J = 5.3 Hz, 1H), 4.63 (t, J = 5.3 Hz, 1H), 4.25-4.15 (m, 2H), 4.15-4.01 (m, 2H), 3.17-2.97 (m, 2H), 2.94 (s, 3H), 2.70-2.58 (m, 1H), 2.23-2.05 (m, 3H). |
| 16 | $^1$H NMR (400 MHz, Methanol-d$_4$) δ 8.17 (s, 1H), 7.31 (dd, J = 8.4, 5.2 Hz, 1H), 7.02 (dd, J = 9.0, 2.3 Hz, 1H), 6.94 (td, J = 8.8, 2.4 Hz, 1H), 6.49 (s, 1H), 6.32 (d, J = 3.7 Hz, 1H), 5.28 (t, J = 6.1 Hz, 1H), 4.71 (t, J = 4.5 Hz, 1H), 4.57 (t, J = 5.2 Hz, 1H), 4.32-4.17 (m, 2H), 4.14 (m, J = 11.0, 6.2 Hz, 1H), 3.09 (ddd, J = 16.3, 8.7, 4.4 Hz, 1H), 2.96 (m, J = 16.1, 7.9 Hz, 1H), 2.75-2.62 (m, 1H), 2.39 (t, J = 20.8 Hz, 2H), 2.15-2.01 (m, 1H). |
| 17 | $^1$H NMR (400 MHz, Methanol-d$_4$) δ 8.19 (s, 1H), 7.28 (dd, J = 8.3, 5.1 Hz, 1H), 7.00 (ddd, J = 17.9, 8.9, 2.4 Hz, 2H), 6.50 (s, 1H), 6.33 (d, J = 3.7 Hz, 1H), 5.32 (t, J = 7.3 Hz, 1H), 4.71 (dd, J = 5.2, 3.8 Hz, 1H), 4.57 (t, J = 5.2 Hz, 1H), 4.30 (ddd, J = 11.0, 7.3, 3.8 Hz, 1H), 4.25-4.08 (m, 2H), 3.05 (ddd, J = 16.1, 8.7, 3.9 Hz, 1H), 2.93 (dt, J = 15.9, 8.0 |

-continued

| Examples | NMR |
|---|---|
| | Hz, 1H), 2.70 (dtd, J = 11.9, 7.6 4.0 Hz, 1H), 2.42 (t, J = 21.0 Hz, 2H), 2.07 (dq, J = 12.9, 8.0 Hz, 1H). |
| 18 | $^1$H NMR (400 MHz, Methanol-d$_4$) δ 8.17 (s, 1H), 7.31 (s, 1H), 7.29 (d, J = 8.1 Hz, 1H), 7.21(d, J = 8.1 Hz, 1H), 6.49 (s, 1H), 6.31 (d, J = 3.7 Hz, 1H), 5.29 (t, J = 7.0 Hz, 1H), 4.74-4.67 (m, 1H), 4.57 (t, J = 5.2 Hz, 1H), 4.32-4.08 (m, 3H), 3.13-3.01 (m, 1H), 3.02-2.89 (m, 1H), 2.74-2.61 (m, 1H), 2.38 (t, J = 20.8 Hz, 2H), 2.13-1.99 (m, 1H). |
| 19 | $^1$H NMR (400 MHz, Methanol-d$_4$) δ 8.17 (s, 1H), 7.60 (s, 1H), 7.51 (q, J = 8.3 Hz, 2H), 6.52 (s, 1H), 6.32 (d, J = 3.5 Hz, 1H), 5.39 (s, 1H), 4.58 (s, 1H), 4.21 (s, 2H), 4.11 (s, 1H), 3.16-3.09 (m, 1H), 3.09-2.97 (m, 2H), 2.31 (t, J = 19.5 Hz, 2H), 2.10 (dd, J = 12.8, 7.9 Hz, 1H). |
| 20 | $^1$H NMR (400 MHz, Methanol-d$_4$) δ 8.18 (s, 1H), 7.60 (s, 1H), 7.58 (d, J = 8.1Hz, 1H), 7.49 (d, J = 8.1 Hz, 1H), 6.52 (s, 1H), 6.32 (d, J = 3.9 Hz, 1H), 5.39 (t, J = 7.2 Hz, 1H), 4.76-4.69 (m, 1H), 4.57 (t, J = 5.1 Hz, 1H), 4.30-4.18 (m, 2H), 4.18-4.09 (m, 1H), 3.22-3.10 (m, 1H). 3.10-2.97 (m, 1H), 2.80-2.67 (m, 1H), 2.40 (t, J = 20.8 Hz, 2H), 2.15-2.01 (m, 1H). |
| 21 | $^1$H NMR (400 MHz, Methanol-d$_4$) δ 8.15 (s, 1H), 6.92 (d, J = 8.3 Hz, 1H), 6.78 (t, J = 9.5 Hz, 1H), 6.45 (s, 1H), 6.31 (d, J = 3.8 Hz, 1H), 5.43 (s, 1H), 4.72 (t, J = 4.7 Hz, 1H), 4.57 (t, J = 4.9 Hz, 1H), 4.28-4.17 (m, 2H), 4.17-4.07 (m, 1H), 3.18 (td, J = 15.0, 13.8, 6.7 Hz, 1H), 2.98 (dq, J = 15.7, 5.6 Hz, 1H), 2.66-2.59 (m, 1H), 2.36 (t, J = 20.4 Hz, 2H), 2.17 (ddt, J = 12.5, 8.0, 4.0 Hz, 1H). |
| 22 | $^1$H NMR (400 MHz, Methanol-d$_4$) δ 8.17 (s, 1H), 7.19 (t, J = 8.9 Hz, 2H), 6.48 (s, 1H), 6.32 (d, J = 3.8 Hz 1H) 5.30 (t, J = 7.2 Hz, 1H), 4.73 (t, J4.6 Hz, 1H), 4.58 (t, J = 5.1 Hz, 1H), 4.23 (dp, J = 12.6, 4.5 Hz, 2H), 4.13 (dt, J = 10.3, 4.9 Hz, 1H), 3.06 (ddd, J = 13.5, 8.7, 4.2 Hz, 1H), 2.94 (dt, J = 16.0, 7.9 Hz, 1H), 2.70 (dtd, J = 12.2, 7.6, 4.2 Hz, 1H), 2.36 (t, J = 20.7 Hz, 2H), 2.14-2.00 (m, 1H). |

Example 23 Preparation of (((((2R,3S,4R,5R)-5-(4-(((R)-5,7-difluoro-2,3-dihydro-1H-inden-1-yl) amino)-6-methyl-1H-pyrazolo[3,4-b]pyridin-1-yl)-3, 4-dihydroxytetrahydrofuran-2-yl)methoxy)(hydroxy) phosphoryl)methyl)phosphonic acid

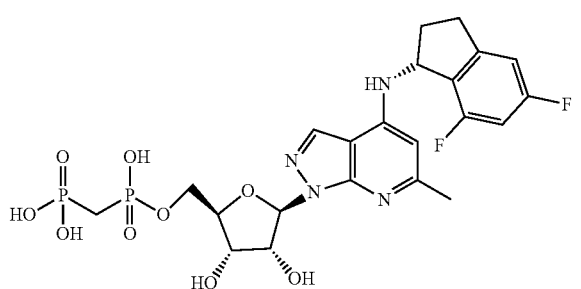

Step 1: Synthesis of (2R,3R,4S,5R)-2-(4-(((R)-5,7-difluoro-2,3-dihydro-1H-inden-1-yl)amino)-6-methyl-1H-pyrazolo[3,4-b]pyridin-1-yl)-5-(hydroxymethyl)tetrahydrofuran-3,4-diol

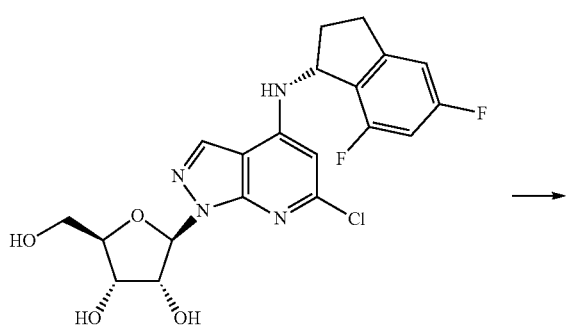

-continued

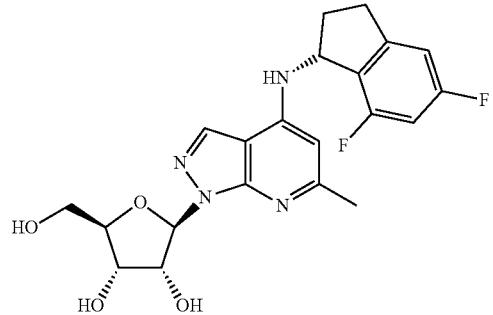

(2R,3R,4S,5R)-2-(6-chloro-4-(((R)-5,7-difluoro-2,3-dihydro-1H-inden-1-yl)amino)-1H-pyrazolo[3,4-b]pyridin-1-yl)-5-(hydroxymethyl)tetrahydrofuran-3,4-diol (0.48 g, 1.06 mmol) was dissolved in dioxane/water (8 mL/2 mL). Potassium carbonate (0.44 g, 3.18 mmol), tetrakistriphenylphosphine palladium (0.37 g, 0.32 mmol) and 2,4,6-trimethyl-, 3,5,2,4,6-trioxatriborocyclohexane (0.40 g, 3.18 mmol) were added in the presence of nitrogen. The re action solution was sealed and reacted under microwave at 130° C. for 3 hours. Ethyl acetate (30 mL) was added to the reaction solution, which was then washed with water an d a saturated brine, dried over sodium sulfate, filtered, concentrated, and then separated by reversed-phase column chromatography [C$_{18}$ column, eluent: water-water/acetonitrile (0-100%)] to obtain (2R,3R,4S,5R)-2-(4-(((R)-5,7-difluoro-2,3-dihydro-1H-inden-1-yl)amino)-6-methyl-1H-pyrazolo[3,4-b]pyridin-1-yl)-5-(hydroxymethyl)tetrahydrofuran-3,4-diol (255 mg, yield: 53%). MS m/z (ESI): 433 [M+H]$^+$.

Step 2: Synthesis of (((((2R,3S,4R,5R)-5-(4-(((R)-5,7-difluoro-2,3-dihydro-1H-inden-1-yl) amino)-6-methyl-1H-pyrazolo[3,4-b]pyridin-1-yl)-3,4-dihydroxytetrahydrofuran-2-yl)meth oxy)(hydroxy)phosphoryl)methyl)phosphonic acid

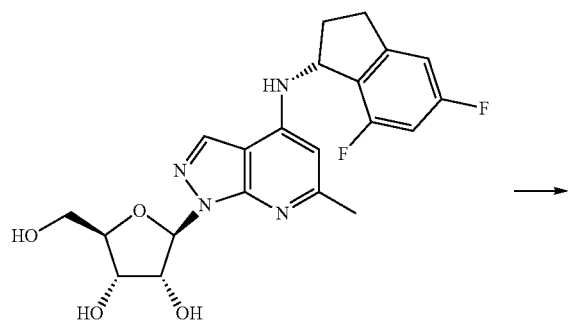

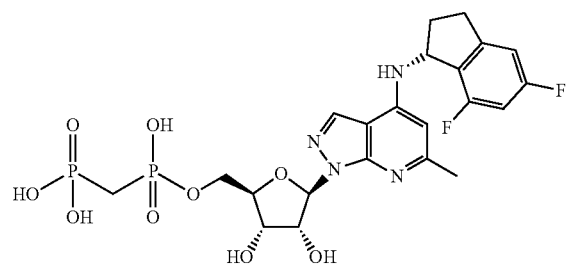

(2R,3R,4S,5R)-2-(4-(((R)-5,7-difluoro-2,3-dihydro-1H-inden-1-yl)amino)-6-methyl-1H-pyrazolo[3,4-b]pyridin-1-yl)-5-(hydroxymethyl)tetrahydrofuran-3,4-diol (255 mg, 0.59 mmol) was dissolved in trimethyl phosphate (3.0 mL). Methylene phosphonium bischloride (515 mg, 2.06 mmol) in a trimethyl phosphate solution (2.0 mL) was added dropwise at 0° C., after which the temperature was held to react for 3 hours. A small quantity of ice was added to quench the reaction, and the reaction solution was stirred for 10 minutes while being held at the current temperature. A saturated sodium bicarbonate solution was added to adjust pH to be pH ≥8, and the reaction solution was stirred at room temperature for 5 hours, and then separated by reversed-phase column chromatography [$C_{18}$ column, eluent: water-water/acetonitrile (5:1)] to obtain (((((2R,3S,4R,5R)-5-(4-(((R)-5,7-difluoro-2,3-dihydro-1H-inden-1-yl)amino)-6-methyl-1H-pyrazolo[3,4-b]pyridin-1-yl)-3,4-dihydroxytetrahydrofuran-2-yl)methoxy)(hydroxy)phosphoryl)methyl)phosphonic acid (136.5 mg, yield: 35%). MS m/z (ESI): 591 [M+H]$^+$.

$^1$H NMR (400 MHz, $D_2O$) δ 8.15 (s, 1H), 6.99 (d, J=8.8 Hz, 1H), 6.83 (t, J=9.8 Hz, 1H), 6.48 (d, J=3.0 Hz, 1H), 6.39 (d, J=5.4 Hz, 1H), 5.51 (s, 1H), 4.93 (t, J=5.6 Hz, 1H), 4.62 (t, J=5.0 Hz, 1H), 4.33 (q, J=4.9 Hz, 1H), 4.07 (hept, J=5.4 Hz, 2H), 3.24-3.11 (m, 1H), 3.04-2.93 (m, 1H), 2.64 (dq, J=15.4, 8.1, 7.4 Hz, 1H), 2.53 (s, 3H), 2.25-2.15 (m, 1H), 2.05 (t, J=19.6 Hz, 2H).

The compound of Example 24 was prepared according to the synthesis method of Example 23:

| Examples | Structural Formula | Name | [M + H]$^+$ |
|---|---|---|---|
| 24 | | (((((2R,3S,4R,5R)-5-(4-(((R)-5-fluoro-2,3-dihydro-1H-inden-1-yl)amino)-6-methyl-1H-pyrazolo[3,4-b]pyridin-1-yl)-3,4-dihydroxytetrhydrofuran-2-yl)methoxy)(hydroxy)phosphoryl)methyl)phosphonic acid | 573 |

The nuclear magnetic resonance data of the compounds prepared in the examples above are as follows:

| Examples | NMR | [M + H]$^+$ |
|---|---|---|
| 24 | $^1$H NMR (400 MHz, Methanol-$d_4$) δ 8.33 (s, 1H), 7.34 (t, J = 6.8 Hz, 1H), 7.06 (d, J = 9.0 Hz, 1H), 6.97 (t, J = 8.6 Hz, 1H), 6.70 (s, 1H), 6.17 (s, 1H), 5.51 (s, 1H), 4.59-4.52 (m, 1H), 4.25 (d, J = 4.6 Hz, 1H), 4.18-4.00 (m, 2H), 3.20-3.08 (m, 1H), 3.00 (dt, J = 16.0, 7.6 Hz, 1H), 2.79-2.72 (m, 1H), 2.66 (s, 3H), 2.25-2.06 (m, 3H). | 573 |

Example 25 Preparation of (((((1R,2R,3S,4S)-4-(2-chloro-4-(((R)-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid

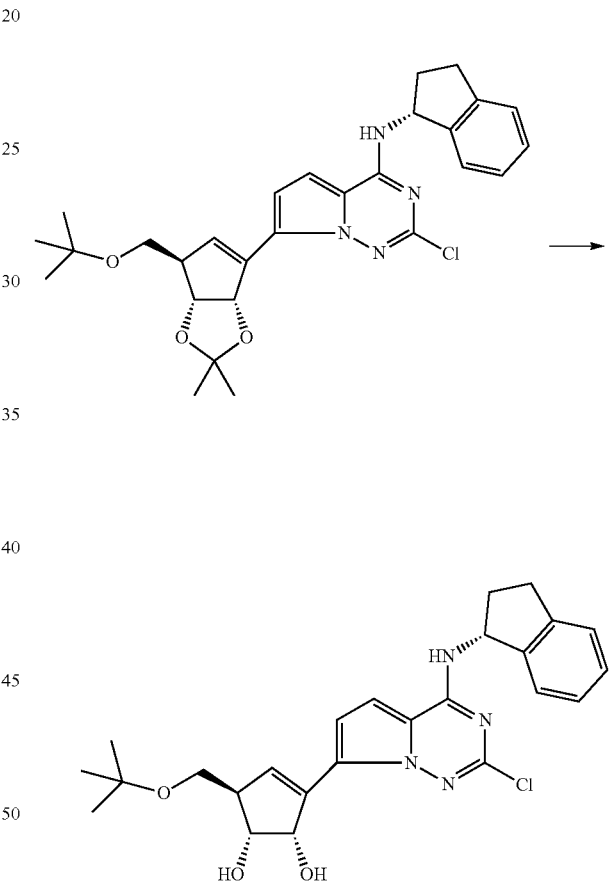

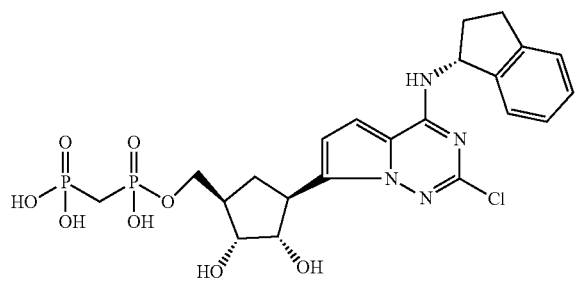 [SMILES: O=P(O)(O)CP(=O)(O)OC[C@H]1C[C@@H](c2ccc3c(N[C@@H]4CCc5ccccc54)nc(Cl)nn23)[C@H](O)[C@@H]1O]

Step 1: Synthesis of 7-((3aR,4R,6aS)-4-(tert-butoxymethyl)-2,2-dimethyl-3a,6a-dihydro-4H-cyclopenta[d][1,3]dioxol-6-yl)-2-chloro-N—((R)-2,3-dihydro-1H-inden-1-yl)pyrrolo[2,1-f][1,2,4]triazin-4-amine

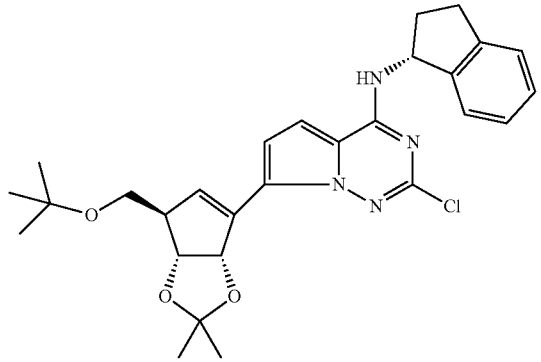

7-((3aR,4R,6aS)-4-(tert-butoxymethyl)-2,2-dimethyl-3a,6a-dihydro-4H-cyclopenta[d][1,3]dioxol-6-yl)-2,4-dichloropyrrolo[2,1-f][1,2,4]triazine (500 mg, 1.21 mmol) and (R)-2,3-dihydro-1H-inden-1-amine (326 mg, 2.42 mmol) was dissolved in 1,4-dioxane (20 mL), and then N,N-diisopropylethylamine (446 mg, 3.63 mmol) was added. The reaction solution was stirred at room temperature for 4 hours. After the reaction was completed, the resulting reaction solution was diluted with water and extracted with ethyl acetate. The organic phases were combined, concentrated and separated by column chromatography [eluent: petroleum ether-petroleum ether/ethyl acetate (20%)] to obtain 7-((3aR,4R,6aS)-4-(tert-butoxymethyl)-2,2-dimethyl-3a,6a-dihydro-4H-cyclopenta[d][1,3]dioxo 1-6-yl)-2-chloro-N—((R)-2,3-dihydro-1H-inden-1-yl)pyrrolo[2,1-f][1,2,4]triazin-4-amine (670 mg, yield: 91%). MS m/z (ESI): 509 [M+H]$^+$.

Step 2: Synthesis of (1R,2S,5R)-5-(tert-butoxymethyl)-3-(2-chloro-4-(((R)-2,3-dihydro-1H-inden-1-yl)amino)pyrrolo[2,1-f][1,2,4]triazin-7-yl)cyclopent-3-ene-1,2-diol

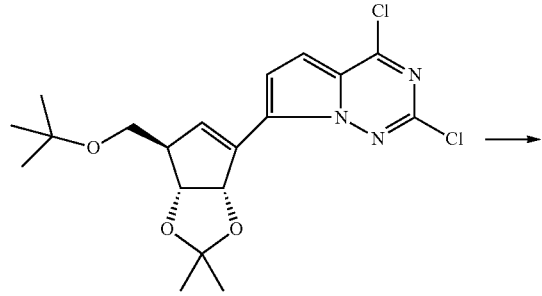

7-((3aR,4R,6aS)-4-(tert-butoxymethyl)-2,2-dimethyl-3a,6a-dihydro-4H-cyclopenta[d][1,3]dioxol-6-yl)-2-chloro-N—((R)-2,3-dihydro-1H-inden-1-yl)pyrrolo[2,1-f][1,2,4]triazin-4-amine (670 mg, 1.31 mmol) was dissolved in 90% acetic acid (40 mL), heated to 60° C. and stirred for 16 hours. After the reaction was completed, the reaction solution was concentrate d and then separated by column chromatography [eluent: dichloromethane-dichloromethane/methanol (10%)] to obtain (1R,2S,5R)-5-(tert-butoxymethyl)-3-(2-chloro-4-(((R)-2,3-dihydro-1H-inden-1-yl)amino)pyrrolo[2,1-f][1,2,4]triazin-7-yl)cyclopent-3-ene-1,2-diol (600 mg, yield: 97%). MS m/z (ESI): 469 [M+H]$^+$.

Step 3: Synthesis of (1S,2R,3R,5S)-3-(tert-butoxymethyl)-5-(2-chloro-4-(((R)-2,3-dihydro-1H-inden-1-yl)amino)pyrrolo[2,1-f][1,2,4]triazin-7-yl)cyclopentane-1,2-diol

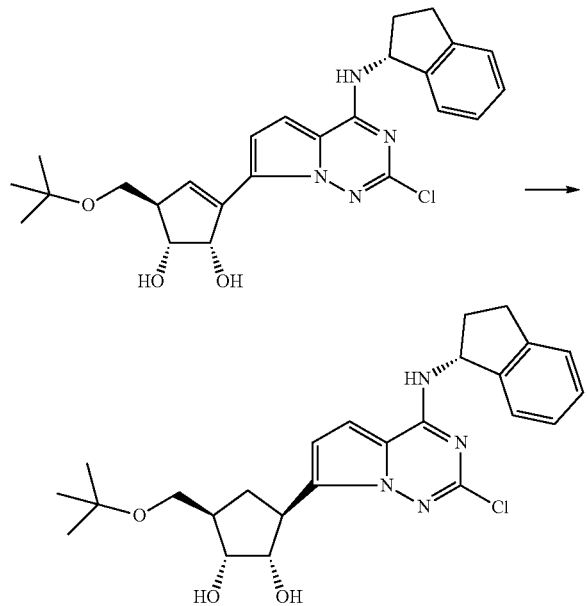

(1R,2S,5R)-5-(tert-butoxymethyl)-3-(2-chloro-4-(((R)-2,3-dihydro-1H-inden-1-yl)amino)pyrrolo[2,1-f][1,2,4]triazin-7-yl)cyclopent-3-ene-1,2-diol (600 mg, 1.28 mmol) and a Crabtree catalyst (100 mg) were dissolved in dichloromethane (100 mL), and then hydrogenated at room temperature and stirred for 16 hours. After the reaction was completed, the reaction solution was concentrated and then separated by column chromatography [eluent: petroleum ether-petroleum ether/ethyl acetate (50%)) to obtain (1S,2R,3R,5S)-3-(tert-butoxymethyl)-5-(2-chloro-4-(((R)-2,3-dihydro-1H-inden-1-yl)amino)pyrrolo[2,1-f][1,2,4]triazin-7-yl)cyclopentane-1,2-diol (500 mg, yield: 83%). MS m/z (ESI): 471 [M+H]$^+$.

Step 4: Synthesis of (1R,2S,3S,5R)-3-(2-chloro-4-(((R)-2,3-dihydro-1H-inden-1-yl)amino)pyrrolo[2,1-f][1,2,4]triazin-7-yl)-5-(hydroxymethyl)cyclopentane-1,2-diol

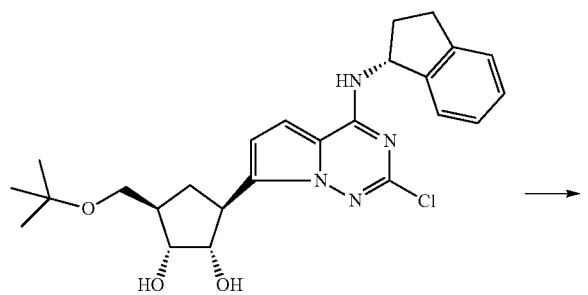

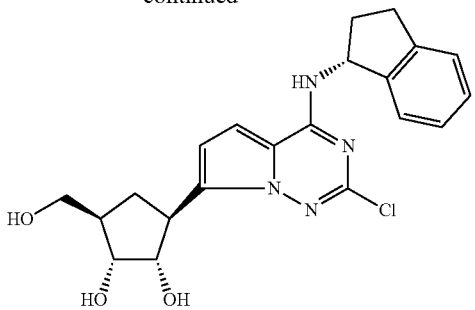

(1S,2R,3R,5S)-3-(tert-butoxymethyl)-5-(2-chloro-4-(((R)-2,3-dihydro-1H-inden-1-yl)amino)pyrrolo[2,1-f][1,2,4]triazin-7-yl)cyclopentane-1,2-diol (500 mg, 1.06 mmol) was dissolved in acetonitrile (4 mL). A dioxane hydrochloride solution (4 mL, 1N) was added to react at room temperature for 1 hour. Then, the reaction solution was concentrated and then separated by reversed-phase column chromatography [C$_{18}$ column, eluent: water-water/acetonitrile (0-50%)] to obtain (1R,2S,3S,5R)-3-(2-chloro-4-(((R)-2,3-dihydro-1H-inden-1-yl)amino)pyrrolo[2,1-f][1,2,4]triazin-7-yl)-5-(hydroxymethyl)cyclopentane-1,2-diol (200 mg, yield: 46%). MS m/z (ESI): 415 [M+H]$^+$.

Step 5: Synthesis of (((((1R,2R,3S,4S)-4-(2-chloro-4-(((R)-2,3-dihydro-1H-inden-1-yl)amino)pyrrolo[2,1-f][1,2,4]triazin-7-yl)-2,3-dihydroxycyclopentyl)methoxy)(hydroxy)phosphorylmethyl)phosphonic acid

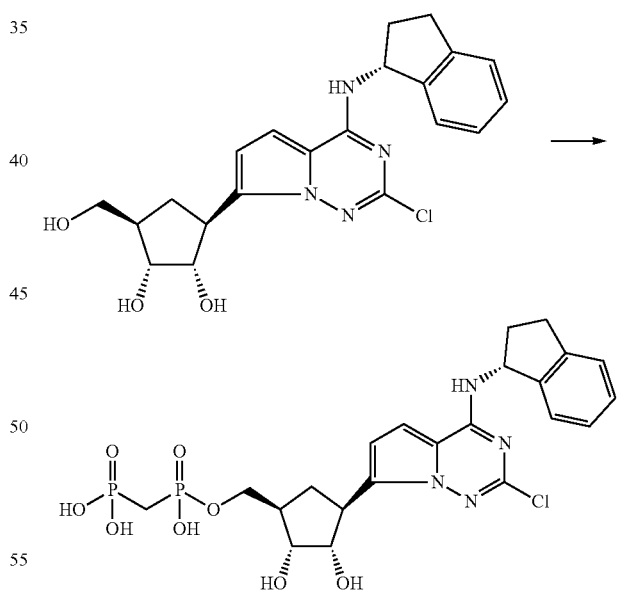

(1R,2S,3S,5R)-3-(2-chloro-4-(((R)-2,3-dihydro-1H-inden-1-yl)amino)pyrrolo[2,1-f][1,2,4]triazin-7-yl)-5-(hydroxymethyl)cyclopentane-1,2-diol (200 mg, 0.48 mmol) was dissolved in trimethyl phosphate (3 mL). Methylene phosphonium bischloride (481 mg, 1.93 mmol) in a trimethyl phosphate solution (0.5 mL) was added dropwise at 0° C., after which the temperature was held to react for 3 hours. A small quantity of ice was added to quench the reaction. Then, the reaction solution was separated by reversed-phase column chromatography [C$_{18}$ column, eluent: water-water/ acetonitrile (5:1)] to obtain (((((1R,2R,3S,4S)-4-(2-chloro-4-(((R)-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid (65 mg, yield: 24%). MS m/z (ESI): 573 [M+H]$^+$.

$^1$H NMR (400 MHz, DMSO-d$_6$+D$_2$O) δ 7.31-7.17 (m, 4H), 6.99 (d, J=4.4 Hz, 1H), 6.54 (d, J=4.4 Hz, 1H), 5.82 (t, J=8.0 Hz, 1H), 4.00-3.90 (m, 3H), 3.80-3.78 (m, 1H), 3.59-3.51 (m, 1H), 3.05-3.00 (m, 1H), 2.93-2.85 (m, 1H), 2.56-2.51 (m, 2H), 2.33-2.19 (m, 3H), 2.04-2.00 (m, 1H), 1.30-1.27 (m, 1H).

The compounds of Examples 26-39 were prepared according to the synthesis method of Example 25:

| Examples | Structural Formula | Name | [M + H]$^+$ |
|---|---|---|---|
| 26 | | (((((1R,2R,3S,4S)-4-(2-chloro-4-(((S)-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 573 |
| 27 | | (((((1R,2R,3S,4S)-4-(2-chloro-4-(((S)-5-fluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 591 |
| 28 | | (((((1R,2R,3S,4S)-4-(2-chloro-4-(((R)-5-fluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 591 |

-continued

| Examples | Structural Formula | Name | [M + H]⁺ |
|---|---|---|---|
| 29 | | (((((1R,2R,3S,4S)-4-(2-chloro-4-(((S)-6-fluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 591 |
| 30 | | (((((1R,2R,3S,4S)-4-(2-chloro-4-(((R)-6-fluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 591 |
| 31 | | (((((1R,2R,3S,4S)-4-(2-chloro-4-(((S)-5,6-difluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 609 |
| 32 | | (((((1R,2R,3S,4S)-4-(2-chloro-4-(((R)-5,6-difluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 609 |

| Examples | Structural Formula | Name | [M + H]+ |
|---|---|---|---|
| 33 | | (((((1R,2R,3S,4S)-4-(2-chloro-4-(((S)-5,7-difluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 609 |
| 34 | | (((((1R,2R,3S,4S)-4-(2-chloro-4-(((R)-5,7-difluoro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 609 |
| 35 | | (((((1R,2R,3S,4S)-4-(2-chloro-4-(((S)-6-(trifluoromethyl)-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 641 |
| 36 | | (((((1R,2R,3S,4S)-4-(2-chloro-4-(((R)-6-(trifluoromethyl)-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 641 |

-continued

| Examples | Structural Formula | Name | [M + H]+ |
|---|---|---|---|
| 37 | | (((((1R,2R,3S,4S)-4-(2-chloro-4-(((S)-5-chloro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 607 |
| 38 | | (((((1R,2R,3S,4S)-4-(2-chloro-4-(((R)-5-chloro-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 607 |
| 39 | | (((((1R,2R,3S,4S)-4-(2-chloro-4-(((R)-5-(trifluoromethyl)-2,3-dihydro-1H-inden-1-yl)amino)pyrrolo[2,1-f][1,2,4]triazin-7-yl)-2,3-dihydroxycyclopentyl)methoxy)(hydroxy)phosphoryl)methyl)phosphonic acid | 641 |

The nuclear magnetic resonance data of the compounds prepared in the examples above are as follows:

| Examples | NMR |
|---|---|
| 26 | $^1$H NMR (400 MHz, DMSO-d$_6$ + D$_2$O) δ 7.29-7.14 (m, 4H), 6.78-6.77 (m, 1H), 6.60-6.59 (m, 1H), 5.68 (t, J = 7.2 Hz, 1H), 4.20-4.14 (m, 1H), 4.04-4.02 (m, 1H), 3.88-3.81 (m, 2H), 3.73-3.70 (m, 1H), 3.61-3.54 (m, 1H) 3.01-2.96 (m, 1H), 2.90-2.81 (m, 1H), 2.57-2.52 (m, 1H), 2.37-2.29 (m, 1H), 2.06 (t, J = 7.2 Hz, 2H), 1.37-1.36 (m, 1H), 1.22-1.19 (m, 1H). |
| 27 | $^1$H NMR (400 MHz, Methanol-d$_4$) δ 7.29 (dd, J = 8.3, 5.3 Hz, 1H), 7.02 (d, J = 9.1 Hz, 1H), 6.97-6.86 (m, 2H), 6.57 (d, J = 4.5 Hz, 1H), 5.91 (t, J = 7.5 Hz, 1H), 4.24-4.18 (m, 1H), 4.15 (t, J = 5.7 Hz, 2H), 4.07 (t, J = 5.0 Hz, 1H), 3.77-3.66 (m, 1H), 3.18-3.06 (m, 1H), 3.02-2.89 (m, 1H), 2.74-2.61 (m, 1H), 2.51-2.36 (m, 4H), 2.18-2.04 (m, 1H), 1.67-1.55 (m, 1H). |
| 28 | $^1$H NMR (400 MHz, DMSO-d$_6$ + D$_2$O) δ 7.28-7.25 (m, 1H), 7.14-7.12 (m, 1H), 7.01-6.98 (m, 2H), 6.54 (d, J = 4.0 Hz, 1H), 5.80-5.78 (m, 1H), 4.00-3.91 (m, 3H), 3.80-3.78 (m, 1H), 3.55-3.52 (m, 1H), 3.02-3.01 (m, 1H), 2.92-2.88 (m, 1H), 2.57-2.53 (m, 2H), 2.23-2.14 (m, 3H), 2.09-2.04 (m, 1H), 1.30-1.23 (m, 1H). |

-continued

| Examples | NMR |
|---|---|
| 29 | $^1$H NMR (400 MHz, Methanol-d$_4$) δ 7.25 (dd, J = 8.3, 5.0 Hz, 1H), 7.04-6.90 (m, 2H), 6.88 (d, J = 4.5 Hz, 1H), 6.56 (d, J = 4.5 Hz, 1H), 5.91 (t, J = 7.7 Hz, 1H), 4.19 (dd, J = 7.4, 5.4 Hz, 1H), 4.13 (t, J = 5.7 Hz, 2H), 4.05 (t, J = 4.9 Hz, 1H), 3.75-3.64 (m, 1H), 3.10-3.00 (m, 1H), 2.96-2.84 (m, 1H), 2.72-2.61 (m, 1H), 2.48-2.34 (m, 4H), 2.15-2.03 (m, 1H), 1.65-1.50 (m, 1H). |
| 30 | $^1$H NMR (400 MHz, Methanol-d$_4$) δ 7.25 (dd, J = 8.2, 5.1 Hz, 1H), 7.02-6.91 (m, 2H), 6.88 (d, J = 4.5 Hz, 1H), 6.56 (d, J = 4.6 Hz, 1H), 5.91 (t, J = 7.7 Hz, 1H), 4.21 (dd, J = 7.4, 5.4 Hz, 1H), 4.15 (t, J = 5.7 Hz, 2H), 4.05 (t, J = 5.0 Hz, 1H), 3.70 (dt, J = 9.4, 7.4 Hz, 1H), 3.05 (ddd, J = 15.9. 8.9, 3.6 Hz, 1H), 2.90 (dt, J = 15.8, 8.2 Hz, 1H), 2.62-2.70 (mm, 1H), 2.55-2.28 (m, 4H), 2.09 (dq, J = 12.9, 8.4 Hz, 1H), 1.65-1.53 (m, 1H). |
| 31 | $^1$H NMR (400 MHz, Methanol-d$_4$) δ 7.05 (t, J = 8.9 Hz, 2H), 6.76 (d, J = 4.5 Hz, 1H), 6.47 (d, J = 4.5 Hz, 1H), 5.77 (t, J = 7.7 Hz, 1H), 4.07 (dd, J = 7.4, 5.4 Hz, 1H), 4.03-3.89 (m, 3H), 3.60 (q, J = 8.1 Hz, 1H), 3.04-2.91 (m, 1H), 2.87-2.73 (m, 1H), 2.62-2.49 (m, 1H), 2.34-2.22 (m, 2H), 2.21 (t, J = 20.2 Hz, 2H), 2.07-1.92 (m, 1H), 1.52-1.40 (m, 1H). |
| 32 | $^1$H NMR (400 MHz, DMSO-d$_6$ + D$_2$O) δ 7.37-7.25 (m, 2H), 6.97 (d, J = 3.6 Hz, 1H), 6.55 (d, J = 4.4 Hz, 1H), 5.77-5.75 (m, 1H), 3.99-3.90 (m, 4H), 3.56-3.50 (m, 1H), 3.03-2.98 (m, 1H), 2.88-2.82 (m, 1H), 2.52-2.50 (m, 2H), 2.22-2.17 (m, 3H), 2.12-2.07 (m, 1H), 1.29-1.22 (m, 1H). |
| 33 | $^1$H NMR (400 MHz, Methanol-d$_4$) δ 6.89 (d, J = 8.5 Hz, 1H), 6.83 (d, J = 4.5 Hz, 1H), 6.74 (td, J = 9.5, 2.1 Hz, 1H), 6.53 (d, J = 4.5 Hz, 1H), 6.15-5.93 (m, 1H), 4.19 (dd, J = 7.3, 5.5 Hz, 1H), 4.14 (t, J = 5.6 Hz, 2H), 4.05 (t, J = 5.0 Hz, 1H), 3.79-3.62 (m, 1H), 3.18 (ddd, J = 15.6, 8.8, 5.8 Hz, 1H), 3.03-2.87 (m, 1H), 2.65 (dtd, J = 13.8, 8.3, 5.5 Hz, 1H), 2.55-2.31 (m, 4H), 2.13 (ddt, J = 14.2, 8.9, 5.9 Hz, 1H), 1.63-1.47 (m, 1H). |
| 34 | $^1$H NMR (400 MHz, Methanol-d$_4$) δ 6.89 (d, J = 8.4 Hz, 1H), 6.83 (d, J = 4.5 Hz, 1H), 6.74 (td, J = 9.5, 2.1 Hz, 1H), 6.53 (d, J = 4.5 Hz, 1H), 6.04 (t, J = 6.7 Hz, 1H), 4.19 (dd, J = 7.4, 5.3 Hz, 1H), 4.14 (t, J = 5.7 Hz, 2H), 4.05 (t, J = 5.0 Hz, 1H), 3.73-3.63 (m, 1H), 3.23-3.12 (m, 1H), 3.01-2.89 (m, 1H), 2.72-2.59 (m, 1H), 2.43 (t, J = 20.6 Hz, 2H), 2.42-2.33 (m, 2H), 2.18-2.07 (m, 1H), 1.63-1.50 (m, 1H). |
| 35 | $^1$H NMR (400 MHz, Methanol-d$_4$) δ 7.55 (s, 1H), 7.54 (d, J = 11.6 Hz, 1H), 7.46 (d, J = 7.9 Hz, 1H), 6.89 (d, J = 4.6 Hz, 1H), 6.58 (d, J = 4.5 Hz, 1H). 5.97 (t, J = 7.7 Hz, 1H), 4.20 (dd, J = 7.4, 5.4 Hz, 1H), 4.15 (t, J = 5.7, Hz, 2H), 4.05 (t, J = 4.9 Hz, 1H), 3.72 (q, J = 8.1 Hz, 1H), 3.22-3.12 (m, 1H), 3.01 (dt, J = 16.5, 8.3 Hz, 1H), 2.69 (dtd, J = 12.1, 8.0, 3.7 Hz, 1H), 2.48-2.28 (m, 4H), 2.12 (dq, J = 13.0, 8.4 Hz, 1H), 1.64-1.52 (m, 1H). |
| 36 | $^1$H NMR (400 MHz, DMSO-d$_6$ + D$_2$O) δ 7.68 (d, J = 8.0 Hz, 1H), 7.65 (s, 1H). 7.60 (d, J = 8.0 Hz, 1H), 7.06 (d, J = 4.0 Hz, 1H), 6.64 (d, J = 4.0 Hz, 1H), 5.95-5.91 (m, 1H), 4.06-4.03 (m, 1H), 3.95-3.93 (m, 2H). 3.89-3.86 (m, 1H), 3.60-3.58 (m, 1H), 3.21-3.15 (m, 1H), 3.09-3.02 (m, 1H), 2.68-2.63 (m, 1H), 2.32-2.12 (m, 5H), 1.37-1.29 (m, 1H). |
| 37 | $^1$H NMR (400 MHz, D$_2$O) δ 7.30 (s, 1H), 7.19 (q, J = 8.2 Hz, 2H), 6.79 (d, J = 4.7 Hz, 1H), 6.62 (d, J = 3.9 Hz, 1H), 5.67 (t, J = 7.8 Hz, 1H), 4.18 (t, J = 7.3 Hz, 1H), 4.10-4.06 (m, 1H), 3.96-3.87 (m, 1H), 3.84-3.76 (m, 1H), 3.63-3.55 (m, 1H), 3.41-3.26 (m, 1H), 3.03-2.94 (m, 1H), 2.91-2.82 (m, 1H), 2.64-2.54 (m, 1H), 2.37-2.29 (m, 2H), 1.93 (t, J = 19.7 Hz, 1H). |
| 38 | $^1$H NMR (400 MHz, Methanol-d$_4$) δ 7.27 (s, 1H), 7.25 (d, J = 8.1 Hz, 1H), 7.18 (dd. J = 8.1, 1.9 Hz, 1H), 6.86 (d, J = 4.5 Hz, 1H), 6.57 (d, J = 4.6 Hz, 1H), 5.90 (t, J = 7.7 Hz, 1H), 4.18 (dd, J = 7.4, 5.3 Hz, 1H), 4.12- 4.01 (m, 3H), 3.70 (q, J = 8.1 Hz, 1H), 3.15-3.03 (m, 1H), 2.99-2.87 (m, 1H), 2.69-2.59 (m, 1H), 2.43-2.36 (m, 2H), 2.36-2.24 (m, 2H), 2.14-2.02 (m, 1H), 1.62-1.50 (m, 1H). |
| 39 | $^1$H NMR (400 MHz, Methanol-d$_4$) δ 7.57 (s, 1H), 7.51-7.41 (m, 2H), 6.87 (d, J = 4.5 Hz, 1H), 6.56 (d, J = 4.5 Hz, 1H), 6.00 (t, J = 8.0 Hz, 1H), 4.20 (dd, J = 7.4, 5.4 Hz, 1H), 4.14 (t, J = 5.7 Hz, 2H), 4.05 (t, J = 5.0 Hz, 1H), 3.75-3.65 (m, 1H), 3.20-3.11 (m, 1H), 3.07-2.96 (m, 1H), 2.74-2.65 (m, 1H), 2.49-2.34 (m, 4H), 2.18-2.06 (m, 1H), 1.63-1.51 (m, 1H). |

Biological Test Evaluation

I. In Vitro Enzymatic Activity Against CD73

The malachite green test using soluble CD73, which is synthesized in vitro was used in the present invention to determine the characteristics of inhibitory activity of the compounds against CD73. The specific experimental procedures were as following:

1. The enzyme reaction in this experiment was carried out in 384-well plates, and CD73 (R&D systems #5795-EN-010) at a concentration of 36 ng/mL, the compounds at different concentrations and 50 μM AMP were incubated for 30 minutes at 25° C. in a 40 uL reaction system (consisting of 25 mM Tris pH 7.5, 5 mM MgCl$_2$, and 0.005% Tween-20);

2. Then, 10 μL of malachite green solution (Sigma) was added to each well to terminate the reaction;

3. The concentration of resulting inorganic phosphate was determined according to the instructions of the reagent manufacturer;

4. The enzymatic activity of CD73 was calculated based on the concentration of the product, and then IC$_{50}$ values were determined by non-linear regression analysis of the inhibition percentage of the compounds of the present invention at different concentrations. The results of the examples of the present invention were shown in Table 1.

II. Inhibition of CD73 Enzymatic Activity on the Cell Surface (Cell Titer Glo (CTG) Experiment)

Human breast cancer cells MDA-MB-231 that endogenously express CD73 were used in the present invention to evaluate the inhibition of the compound against the CD73 enzymatic activity expressed on the cell surface. The cells used were from the Cell Bank of the Chinese Academy of Sciences. The specific experimental procedures were as follows:

1. Before the test, MDA-MB231 cells were seeded to a 96-well plate at 20000 cells/well;
2. In RPMI1640, 10% fetal bovine serum (Gibco, 10099-141), placed in a 5% $CO_2$ incubator at 37° C. overnight (the cells were washed three times by using a serum-free RPMI medium right before the test):
3. 50 μl of serum-free media containing the compounds at different concentrations were added to the cells and incubated for 15 minutes;
4. 25 μL of 1.2 mM AMP was added for incubation at 37° C. for 2 hours, 25 μL of supernatant was then collected from the cells and mix with 25 μL of 100 μM ATP, and then the concentration of AMP in the samples was determined by CTG (Promega, #G7573);
5. Then, a reduction ratio of the substrate AMP level in the cell culture supernatant collected after the reaction was quantitatively determined to evaluate the inhibitory effects of the examples of the present invention and the positive compounds against the CD73 enzymatic activity on the cell surface;
6. Finally, the concentration of the compound leading to half maximal inhibition of enzymatic activity (IC50) was determined using a four-parameter non-linear logistic model curve fit in Graphpad Prism. The results of the examples of the present invention were shown in Table 1.

TABLE 1

Biological test results

| Examples No. | Enzymatic activity $IC_{50}$ (nM) | Cellular activity $IC_{50}$ (nM) | Examples No. | Enzymatic activity $IC_{50}$ (nM) | Cellular activity $IC_{50}$ (nM) |
|---|---|---|---|---|---|
| Example 1 | 6.8 | 0.373 | Example 21 | 0.21 | 0.21 |
| Example 2 | 20.6 | 0.73 | Example 22 | 0.26 | 0.151 |
| Example 3 | 1.6 | 0.722 | Example 23 | 0.89 | 0.245 |
| Example 4 | 23.4 | 0.9 | Example 24 | 1.26 | 0.256 |
| Example 5 | 36.5 | 0.49 | Example 25 | 5.5 | 0.55 |
| Example 6 | 2.4 | 0.302 | Example 26 | NT | 3.182 |
| Example 7 | 15.1 | 1.61 | Example 27 | 82.6 | 2.54 |
| Example 8 | 2.0 | 0.59 | Example 28 | 3.95 | 0.252 |
| Example 9 | 4.8 | 1.45 | Example 29 | 15.0 | 0.71 |
| Example 10 | 3.1 | 0.21 | Example 30 | 3.4 | 0.19 |
| Example 11 | 31.6 | 0.99 | Example 31 | 48.6 | 0.95 |
| Example 12 | 0.26 | 0.26 | Example 32 | 4.08 | 0.27 |
| Example 13 | 0.42 | 0.13 | Example 33 | 27.9 | 2.4 |
| Example 14 | 0.16 | 0.45 | Example 34 | 1.01 | 0.22 |
| Example 15 | 0.97 | 0.121 | Example 35 | 354.2 | 5.73 |
| Example 16 | 0.34 | 0.176 | Example 36 | 21.7 | 0.63 |
| Example 17 | 0.32 | 0.14 | Example 37 | >1000 | 59.97 |
| Example 18 | 1.67 | 0.24 | Example 38 | 7.8 | 0.266 |
| Example 19 | 11.81 | 0.54 | Example 39 | 63.0 | 0.743 |
| Example 20 | 0.71 | 0.27 | WO2017120508 | 3.37 | 0.508 |
| | | | Example 127 | | |

Note
"NT", i.e., "Not Tested", means that the compound was not tested.

It can be seen from the activity data of specific examples that the series of compounds of the present invention have a strong inhibitory effect on the enzymatic and cellular activities of CD73.

All documents mentioned in the present application are hereby incorporated by reference in their entirety, just as each document is cited separately as a reference. In addition, it should be understood that various modifications and changes may be made by those skilled in the art after reading the above teachings of the present invention and these equivalent forms also fall within the scope defined by the claims appended hereto.

We claim:

1. A compound having the formula (IIa), formula (IIb) or formula (IIc):

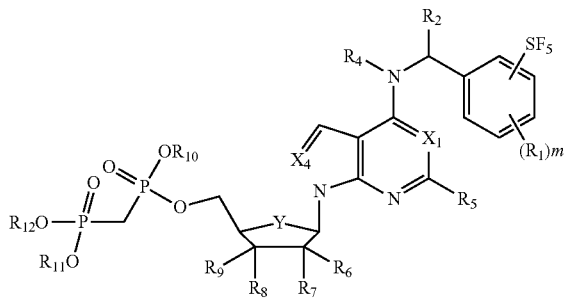

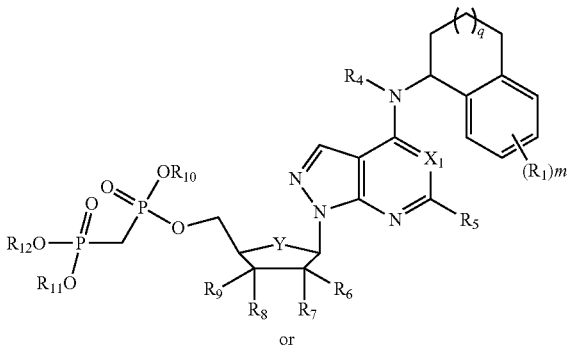

or

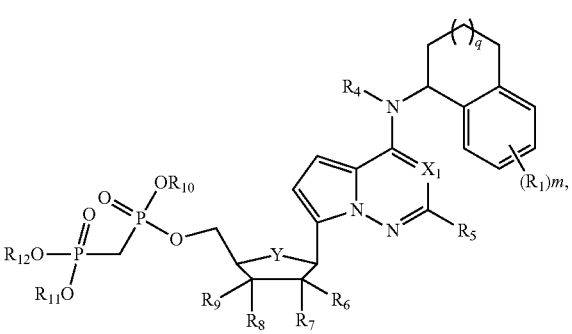

wherein,
in formula (IIa), $X_1$ is CH or N, $X_4$ is N, and Y is O;
in formula (IIb), $X_1$ is CH and Y is O;
in formula (IIc), $X_1$ is N and Y is $CH_2$; and
each $R_1$ is independently selected from the group consisting of hydrogen, deuterium, halogen, cyano, nitro, $C_{1-4}$ alkyl, $C_{3-6}$ cycloalkyl, 3-6 membered heterocyclyl, $C_{5-6}$ aryl, 5-6 membered heteroaryl, —$SF_5$, —$S(O)_rR_{19}$, —O—$R_{20}$, —C(O)O$R_{20}$, —C(O)$R_{21}$, —O—C(O)$R_{21}$ and —$NR_{22}R_{23}$, or, when m≥2, two of $R_1$ together with the moiety directly attached thereto form 5-6 membered cycloalkyl, 5-6 membered aryl, 5-6 membered heterocyclyl or 5-6 membered heteroaryl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-6}$ aryl, 5-6 membered heteroaryl, =O, —S(O)$_r$R$_{19}$, —O—R$_{20}$, —C(O)OR$_{20}$, —C(O)R$_{21}$, —O—C(O)R$_{21}$ and —NR$_{22}$R$_{23}$;

$R_2$ is selected from the group consisting of hydrogen, deuterium, F, Cl, cyano, methyl, ethyl, isopropyl, allyl, ethynyl, cyclopropyl, hydroxymethyl, cyanomethyl, trifluoromethyl, trideuteriomethyl, methoxy, trifluoromethoxy, trideuteriomethoxy, amino, methylamino and dimethylamino;

each $R_4$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-6}$ aryl and 5-6 membered heteroaryl, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-6}$ aryl, 5-6 membered heteroaryl, =O, —S(O)$_r$R$_{19}$, —O—R$_{20}$, —C(O)OR$_{20}$, —C(O)R$_{21}$, —O—C(O)R$_{21}$ and —NR$_{22}$R$_{23}$;

each $R_5$ is independently selected from the group consisting of hydrogen, deuterium, halogen, cyano, $C_{1-4}$ alkyl, $C_{3-6}$ cycloalkyl, 3-6 membered heterocyclyl, phenyl, 5-6 membered heteroaryl, —SF$_5$, methylthio, methylsulfonyl, isopropylsulfonyl, aminosulfonyl, methoxy, ethyoxyl, isopropoxy, hydroxy, —C(O)OH, methoxycarbonyl, ethoxycarbonyl, formyl, acetyl, acetoxyl, amino, dimethylamino, —C(=NR$_{22}$)R$_{21}$, —N(R$_{22}$)—C(=NR$_{23}$)R$_{21}$, aminocarbonyl, dimethylaminocarbonyl and acetylamino, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, phenyl, 5-6 membered heteroaryl, =O, methylthio, methylsulfonyl, isopropylsulfonyl, aminosulfonyl, methoxy, ethyoxyl, isopropoxy, hydroxy, —C(O)OH, methoxycarbonyl, ethoxycarbonyl, formyl, acetyl, acetoxyl, amino, dimethylamino, aminocarbonyl, dimethylaminocarbonyl and acetylamino;

$R_6$ and $R_7$ are each independently selected from the group consisting of hydrogen, deuterium, halogen, cyano, nitro, azido, methyl, ethyl, n-propyl, isopropyl, vinyl, 1-propenyl, 2-propenyl, ethynyl, hydroxy, methoxy and acetoxyl, above groups are optionally further substituted by one or more substituents selected from the group consisting of deuterium, halogen, cyano, methyl, ethyl, n-propyl, isopropyl, vinyl, ethynyl, cyclopropyl, trifluoromethyl, trideuteriomethyl, hydroxy, methoxy and acetoxyl;

$R_8$ and $R_9$ are each independently selected from the group consisting of hydrogen, deuterium, halogen, cyano, nitro, azido, methyl, ethyl, n-propyl, isopropyl, vinyl, 1-propenyl, 2-propenyl, ethynyl, cyclopropyl, hydroxy, methoxy and acetoxyl, above groups are optionally further substituted by one or more substituents selected from the group consisting of deuterium, halogen, cyano, methyl, ethyl, n-propyl, isopropyl, vinyl, ethynyl, cyclopropyl, trifluoromethyl, trideuteriomethyl, hydroxy, methoxy and acetoxyl;

$R_{10}$, $R_{11}$ and $R_{12}$ are each independently selected from the group consisting of hydrogen, deuterium, $C_{1-4}$ alkyl, $C_{3-6}$ cycloalkyl, 3-6 membered heterocyclyl, $C_{5-6}$ aryl, 5-6 membered heteroaryl, —C(O)OR$_{20}$, —C(O)R$_{21}$ and —C(O)NR$_{22}$R$_{23}$, above groups are optionally further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{5-6}$ aryl, 5-6 membered heteroaryl, =O, —S(O)$_r$R$_{19}$, —O—R$_{20}$, —C(O)OR$_{20}$, —C(O)R$_{21}$, —O—C(O)R$_{21}$, —NR$_{22}$R$_{23}$, —C(O)NR$_{22}$R$_{23}$ and —N(R$_{22}$)—C(O)R$_{21}$;

each $R_{19}$ is independently selected from the group consisting of hydrogen, deuterium, hydroxy, $C_{1-4}$ alkyl, $C_{2-6}$ alkenyl, $C_{3-6}$ cycloalkyl, 3-6 membered heterocyclyl, $C_{5-6}$ aryl, 5-6 membered heteroaryl and —NR$_{22}$R$_{23}$, above groups are optionally further substituted by one or more substituents selected from the group consisting of deuterium, halogen, hydroxy, =O, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —NR$_{22}$R$_{23}$;

each $R_{20}$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-6}$ aryl and 5-6 membered heteroaryl, above groups are optionally further substituted by one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —NR$_{22}$R$_{23}$;

each $R_{21}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —NR$_{22}$R$_{23}$, above groups are optionally further substituted by one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy and —NR$_{22}$R$_{23}$;

$R_{22}$ and $R_{23}$ are each independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{5-6}$ aryl, 5-6 membered heteroaryl, sulfonyl, methylsulfonyl, isopropylsulfonyl, cyclopropylsulfonyl, p-toluenesulfonyl, amino, monoalkylamino, dialkylamino and $C_{1-4}$ alkanoyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy, amino, monoalkylamino, dialkylamino and $C_{1-4}$ alkanoyl; or $R_{22}$ and $R_{23}$, together with the nitrogen atom directly attached thereto, form 4-6 membered heterocyclyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkoxy, 3-6 membered heterocyclyl, 3-6 membered heterocyclyloxy, $C_{5-6}$ aryl, $C_{5-6}$ aryloxy, 5-6 membered heteroaryl, 5-6 membered heteroaryloxy, amino, monoalkylamino, dialkylamino and $C_{1-4}$ alkanoyl;

each q is independently 0, 1, 2 or 3;

each m is independently 0, 1, 2 or 3; and each r is independently 0, 1 or 2; or a stereoisomer or pharmaceutically-acceptable salt thereof.

2. A compound according to claim 1, wherein, each $R_1$ is independently selected from the group consisting of hydrogen, deuterium, halogen, cyano, nitro, $C_{1-4}$ alkyl, $C_{3-6}$ cycloalkyl, 3-6 membered heterocyclyl, $C_{5-6}$ aryl, 5-6 membered heteroaryl, —$SF_5$, —$S(O)_rR_{19}$, —O—$R_{20}$, —$C(O)OR_{20}$, —$C(O)R_{21}$, —O—$C(O)R_{21}$ and —$NR_{22}R_{23}$, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —O—$R_{20}$, —$C(O)OR_{20}$ and —$C(O)R_{21}$;

each $R_4$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{5-6}$ aryl and 5-6 membered heteroaryl, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —O—$R_{20}$, —$C(O)OR_{20}$ and —$C(O)R_{21}$;

each $R_5$ is independently selected from the group consisting of hydrogen, deuterium, halogen, cyano, $C_{1-4}$ alkyl, $C_{3-6}$ cycloalkyl, 3-6 membered heterocyclyl, phenyl, 5-6 membered heteroaryl, —$SF_5$, methylthio, methylsulfonyl, isopropylsulfonyl, aminosulfonyl, methoxy, ethyoxyl, isopropoxy, hydroxy, —C(O)OH, methoxycarbonyl, ethoxycarbonyl, formyl, acetyl, acetoxyl, amino, dimethylamino, aminocarbonyl, dimethylaminocarbonyl and acetylamino, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, methoxy, ethyoxyl, isopropoxy, hydroxy, —C(O)OH, methoxycarbonyl, ethoxycarbonyl, formyl, acetyl and acetoxyl;

$R_6$ and $R_7$ are each independently selected from the group consisting of hydrogen, deuterium, halogen, cyano, nitro, azido, methyl, ethyl, n-propyl, isopropyl, hydroxy, methoxy and acetoxyl, above groups are optionally further substituted by one or more substituents selected from the group consisting of deuterium, halogen, cyano, methyl, ethyl, n-propyl, isopropyl, vinyl, ethynyl, cyclopropyl, trifluoromethyl, trideuteriomethyl, hydroxy, methoxy and acetoxyl;

$R_8$ and $R_9$ are each independently selected from the group consisting of hydrogen, deuterium, halogen, cyano, nitro, azido, methyl, ethyl, n-propyl, isopropyl, cyclopropyl, hydroxy, methoxy and acetoxyl, above groups are optionally further substituted by one or more substituents selected from the group consisting of deuterium, halogen, cyano, methyl, ethyl, n-propyl, isopropyl, cyclopropyl, trifluoromethyl, trideuteriomethyl, hydroxy, methoxy and acetoxyl;

$R_{10}$, $R_{11}$ and $R_{12}$ are each independently selected from the group consisting of hydrogen, deuterium, $C_{1-4}$ alkyl, $C_{3-6}$ cycloalkyl, 3-6 membered heterocyclyl, $C_{5-6}$ aryl, 5-6 membered heteroaryl, —$C(O)OR_{20}$, —$C(O)R_{21}$ and —$C(O)NR_{22}R_{23}$, above groups are optionally further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —$S(O)_rR_{19}$, —O—$R_{20}$, —$C(O)OR_{20}$, —$C(O)R_{21}$ and —O—$C(O)R_{21}$;

each $R_{19}$ is independently selected from the group consisting of hydrogen, deuterium, hydroxy, $C_{1-4}$ alkyl and $C_{3-6}$ cycloalkyl, above groups are optionally further substituted by one or more substituents selected from the group consisting of deuterium, halogen, hydroxy, =O, $C_{1-4}$ alkyl, $C_{1-4}$ alkoxy and $C_{3-6}$ cycloalkyl;

each $R_{20}$ is independently selected from the group consisting of hydrogen, deuterium, $C_{1-4}$ alkyl and $C_{3-6}$ cycloalkyl, above groups are optionally further substituted by one or more substituents selected from the group consisting of deuterium, halogen, hydroxy, =O, cyano, $C_{1-4}$ alkyl, $C_{1-4}$ alkoxy and $C_{3-6}$ cycloalkyl;

each $R_{21}$ is independently selected from the group consisting of hydrogen, deuterium, hydroxy, $C_{1-4}$ alkyl and $C_{1-4}$ alkoxy, above groups are optionally further substituted by one or more substituents selected from the group consisting of deuterium, halogen, hydroxy, cyano, $C_{1-4}$ alkyl, $C_{1-4}$ alkoxy and $C_{3-6}$ cycloalkyl;

$R_{22}$ and $R_{23}$ are each independently selected from the group consisting of hydrogen, deuterium, hydroxy, $C_{1-4}$ alkyl, $C_{3-6}$ cycloalkyl, 3-6 membered heterocyclyl and $C_{1-4}$ alkanoyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkoxy, 3-6 membered heterocyclyl and $C_{1-4}$ alkanoyl; or a stereoisomer or pharmaceutically-acceptable salt thereof.

3. A compound according to claim 1 having the formula (IIIb):

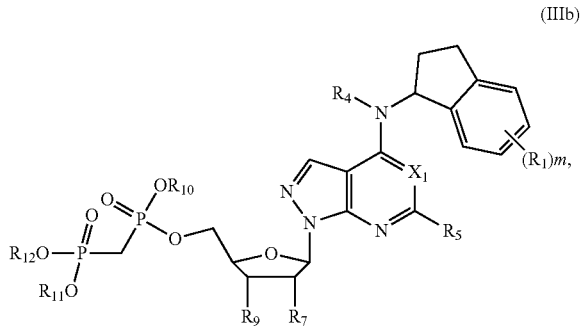

(IIIb)

wherein, $X_1$ is CH;

wherein, $R_1$ is selected from the group consisting of hydrogen, deuterium, F, Cl, cyano, methyl, ethyl, n-propyl, isopropyl, difluoromethyl, trifluoromethyl, dideuteriomethyl, trideuteriomethyl, $C_{3-6}$ cycloalkyl and 3-6 membered heterocyclyl;

R₄ is selected from the group consisting of hydrogen, deuterium, methyl, ethyl, n-propyl, isopropyl, C₂₋₄ alkenyl and C₃₋₆ cycloalkyl;

R₅ is selected from the group consisting of hydrogen, deuterium, F, Cl, cyano, azido, methyl, ethyl, n-propyl, isopropyl, C₂₋₆ alkenyl, C₂₋₆ alkynyl and C₃₋₆ cycloalkyl;

R₇ is selected from the group consisting of hydrogen, deuterium, halogen, methyl, ethyl, n-propyl, isopropyl and hydroxy;

R₉ is selected from the group consisting of hydrogen, deuterium, halogen, methyl, ethyl, n-propyl, isopropyl and hydroxy;

R₁₀, R₁₁ and R₁₂ are each independently selected from the group consisting of hydrogen, deuterium, methyl, ethyl, n-propyl and isopropyl; and m is 0, 1, 2 or 3; or a stereoisomer or pharmaceutically-acceptable salt thereof.

4. A compound according to claim 1 having the formula (IIIc):

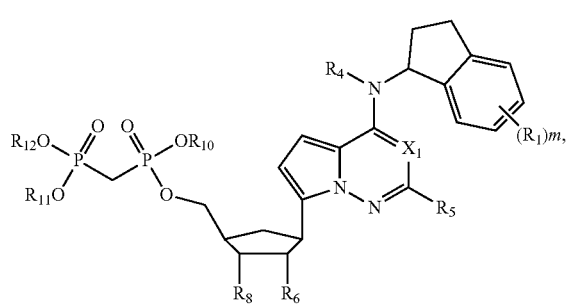

(IIIc)

wherein, X₁ is N;

R₁ is selected from the group consisting of hydrogen, deuterium, F, Cl, cyano, methyl, ethyl, n-propyl, isopropyl, difluoromethyl, trifluoromethyl, dideuteriomethyl, trideuteriomethyl, C₃₋₆ cycloalkyl and 3-6 membered heterocyclyl;

R₄ is selected from the group consisting of hydrogen, deuterium, methyl, ethyl, n-propyl, isopropyl, C₂₋₄ alkenyl and C₃₋₆ cycloalkyl;

R₅ is selected from the group consisting of hydrogen, deuterium, F, Cl, cyano, azido, methyl, ethyl, n-propyl, isopropyl, C₂₋₆ alkenyl, C₂₋₆ alkynyl and C₃₋₆ cycloalkyl;

R₆ is selected from the group consisting of hydrogen, deuterium, halogen, methyl, ethyl, n-propyl, isopropyl and hydroxy;

R₈ is selected from the group consisting of hydrogen, deuterium, halogen, methyl, ethyl, n-propyl, isopropyl and hydroxy;

R₁₀, R₁₁ and R₁₂ are each independently selected from the group consisting of hydrogen, deuterium, methyl, ethyl, n-propyl and isopropyl; and m is 0, 1, 2 or 3; or a stereoisomer or pharmaceutically-acceptable salt thereof.

5. A compound according to claim 2, wherein the compound is selected from the following compounds:

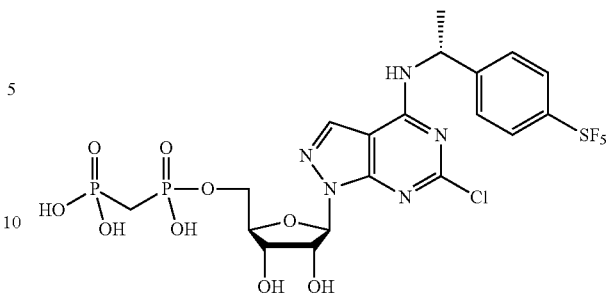

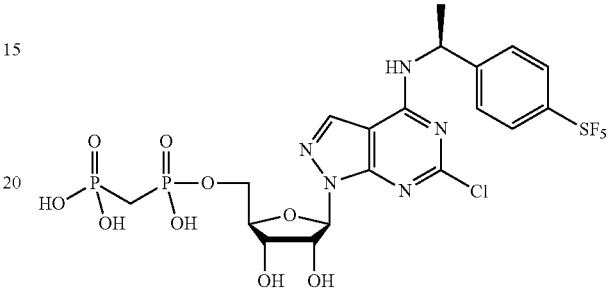

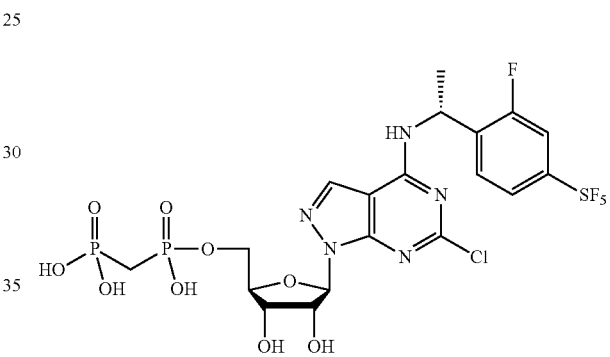

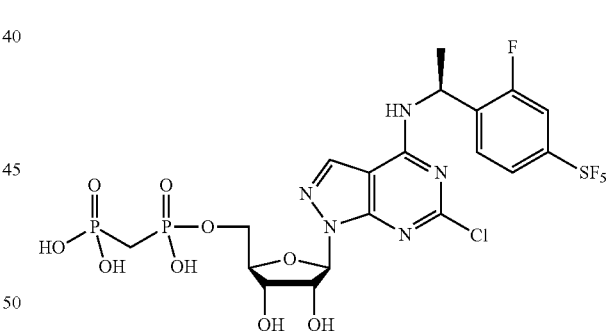

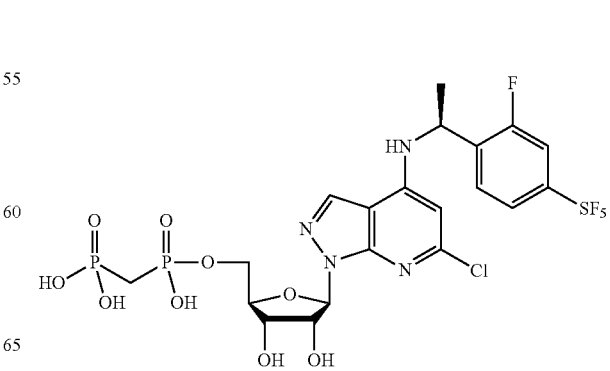

105
-continued
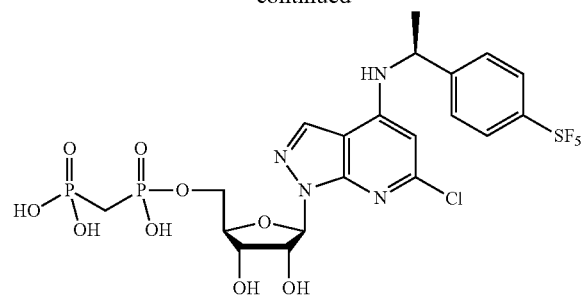
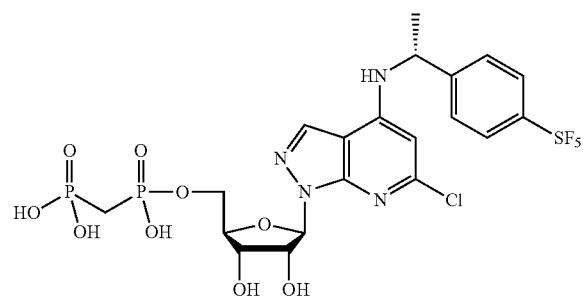
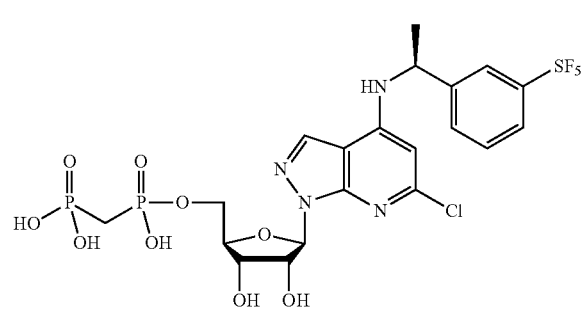
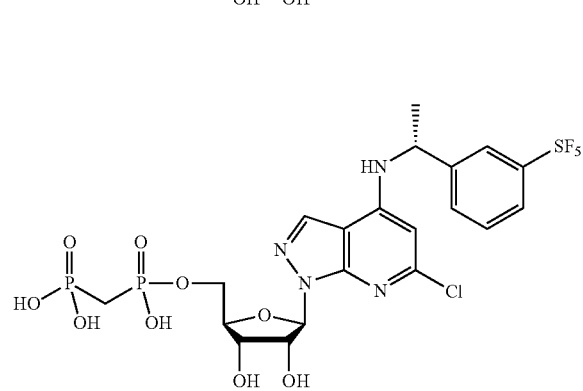
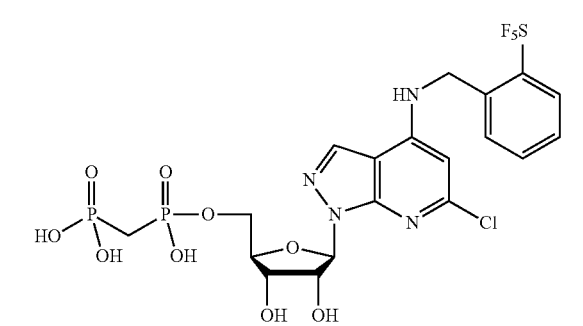
106
-continued
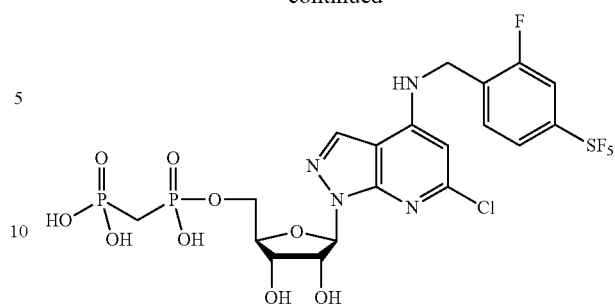
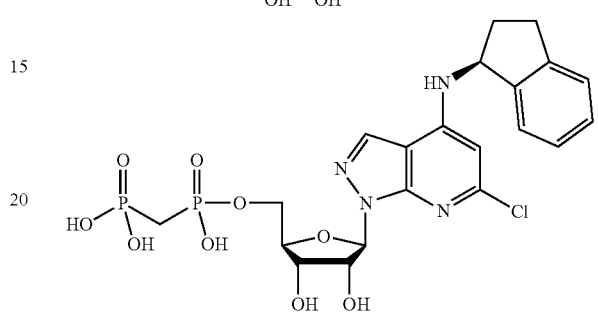
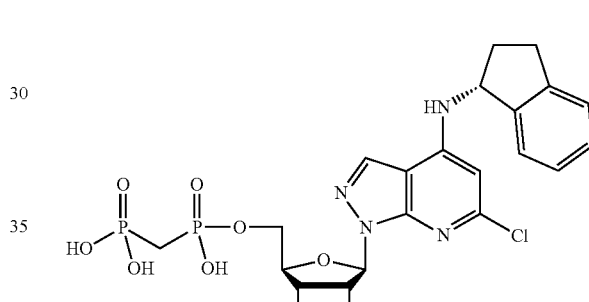
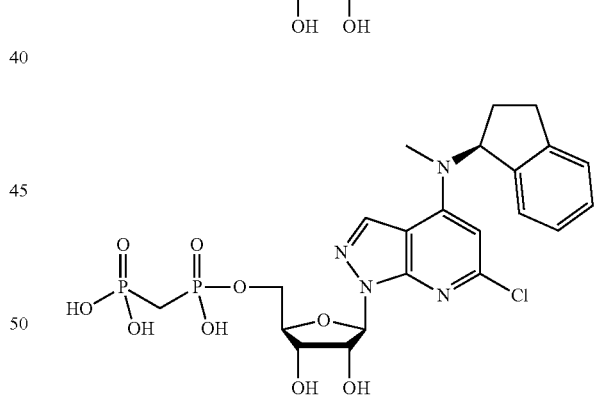
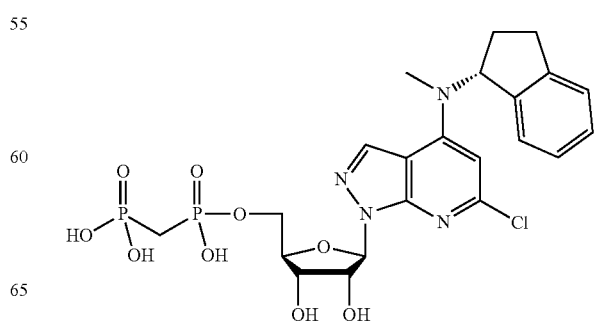

-continued
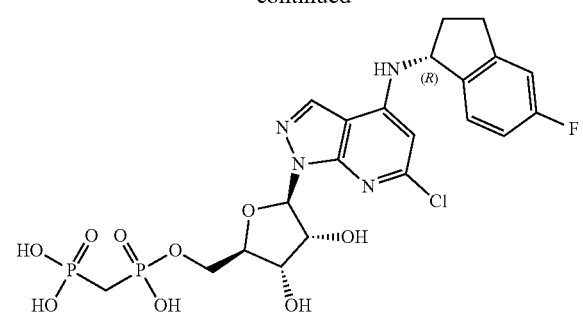
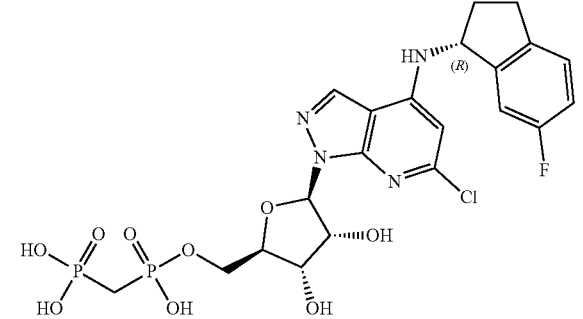
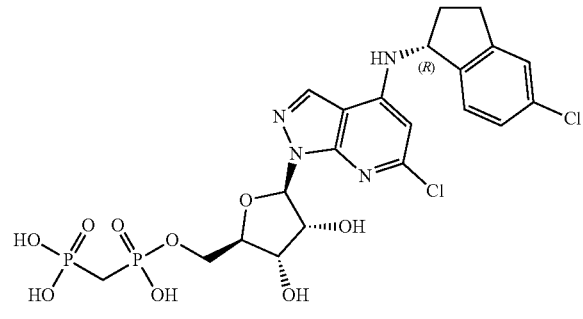
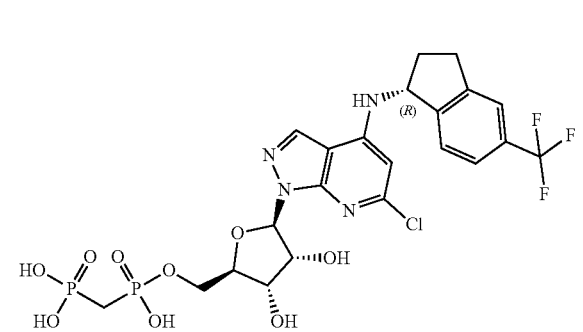
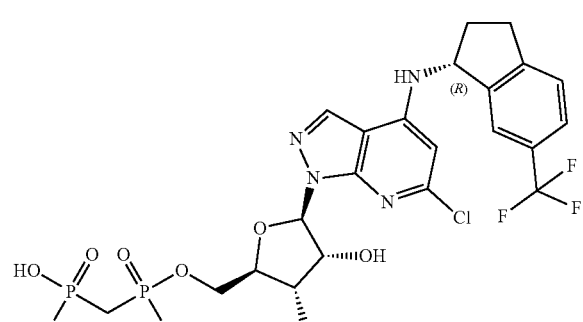
-continued
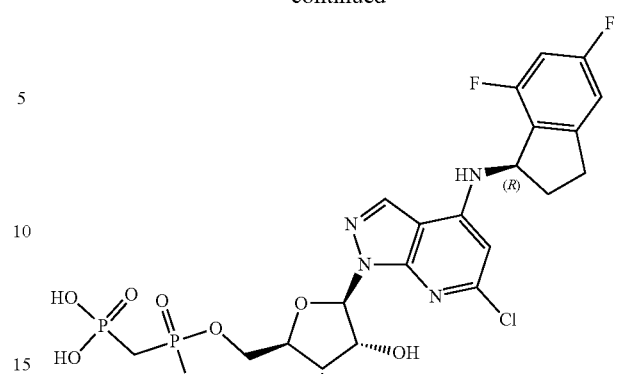
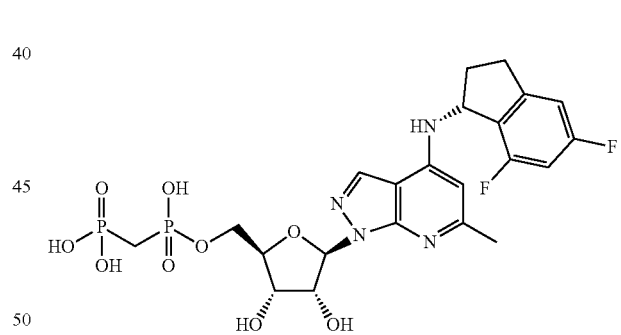
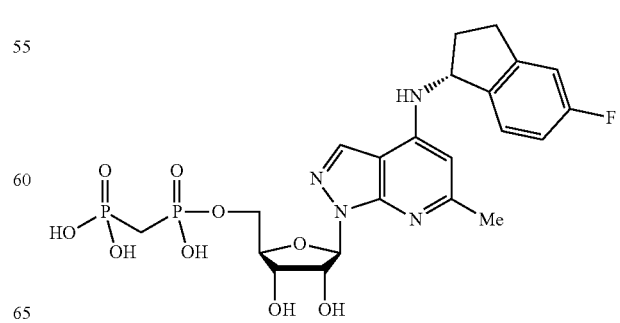

109
-continued
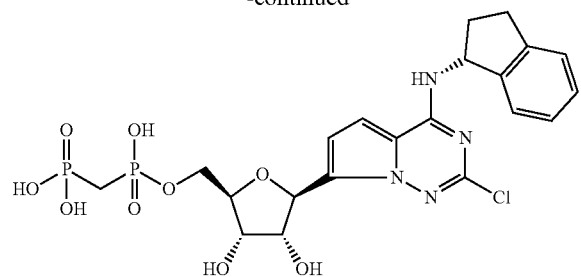
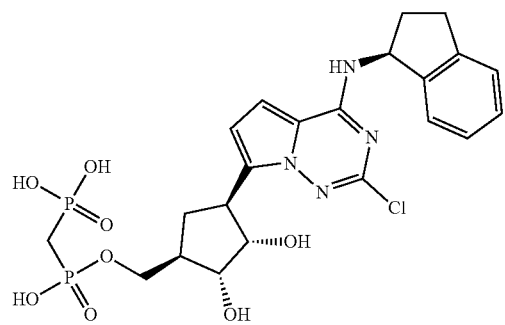
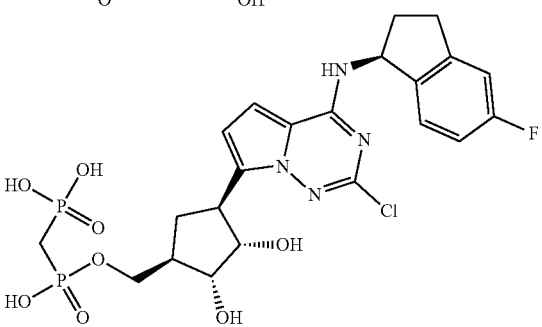
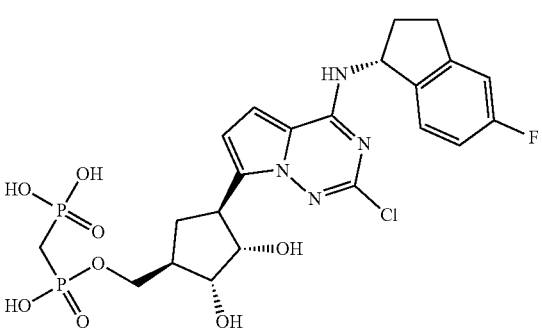
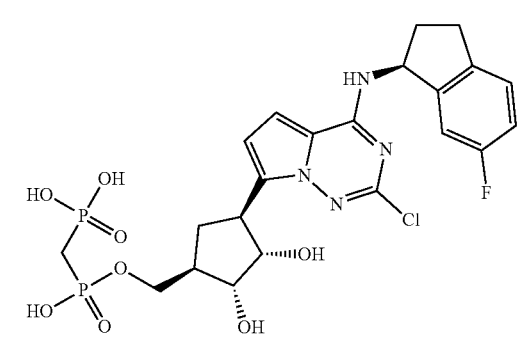
110
-continued
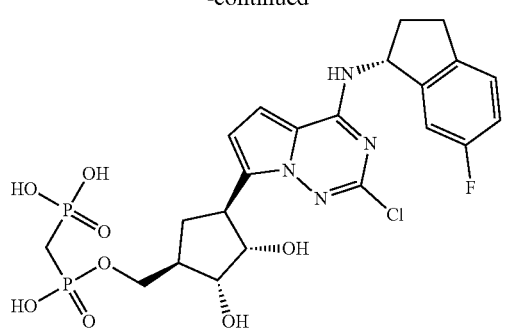
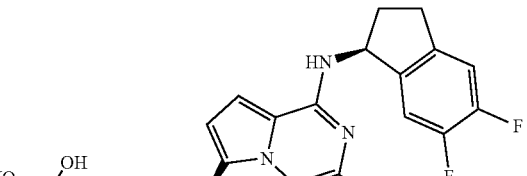
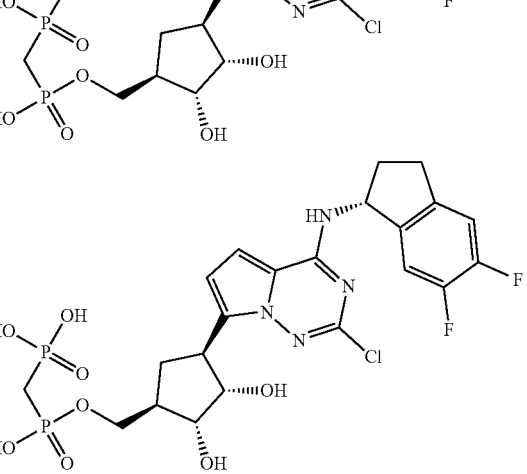
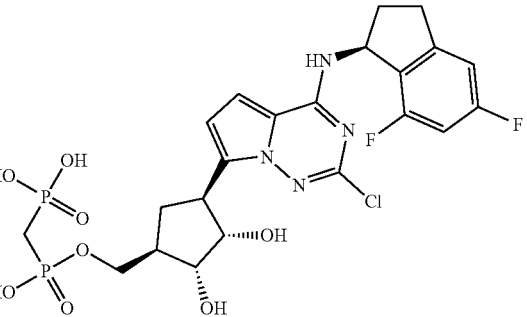
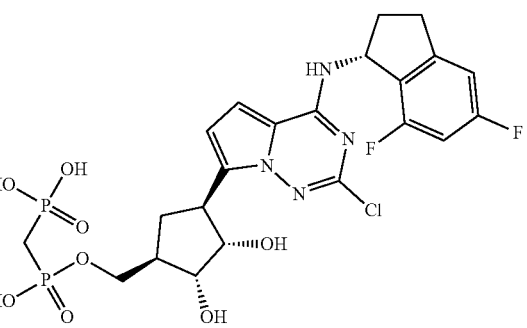

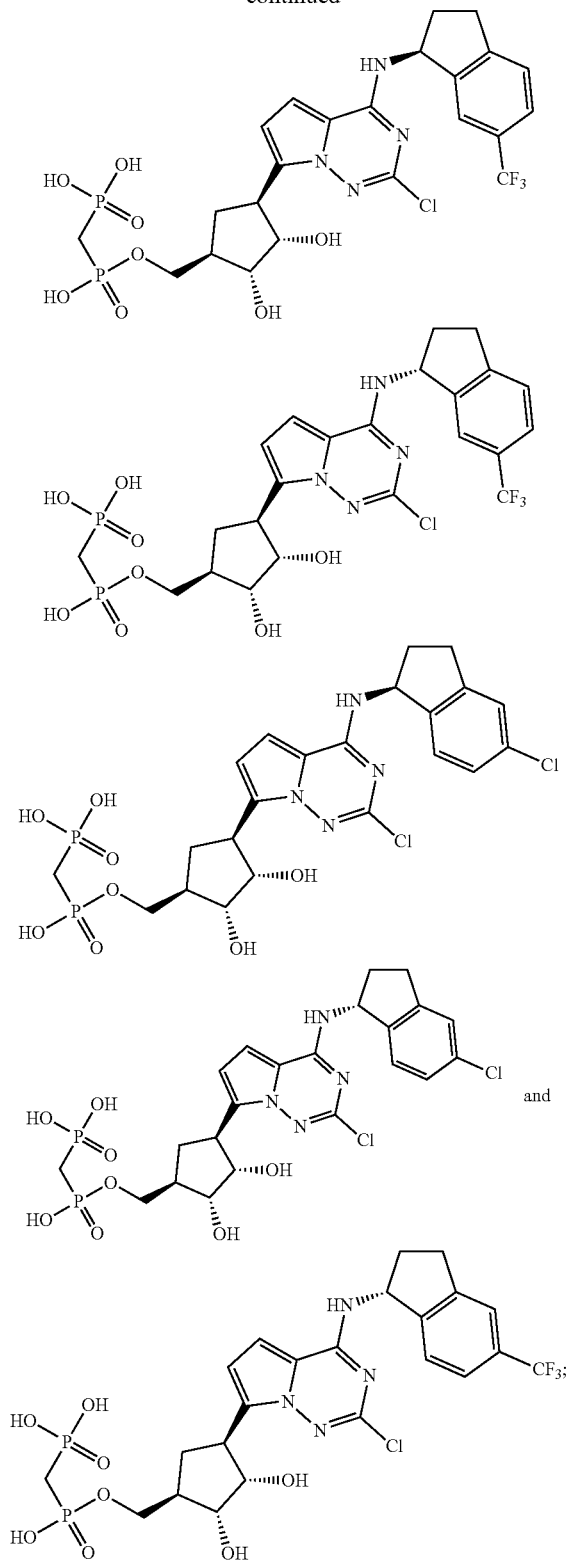

or a stereoisomer or pharmaceutically-acceptable salt thereof.

6. A process for preparing a compound of claim 1, or a stereoisomer or pharmaceutically-acceptable salt thereof, comprising the following steps:

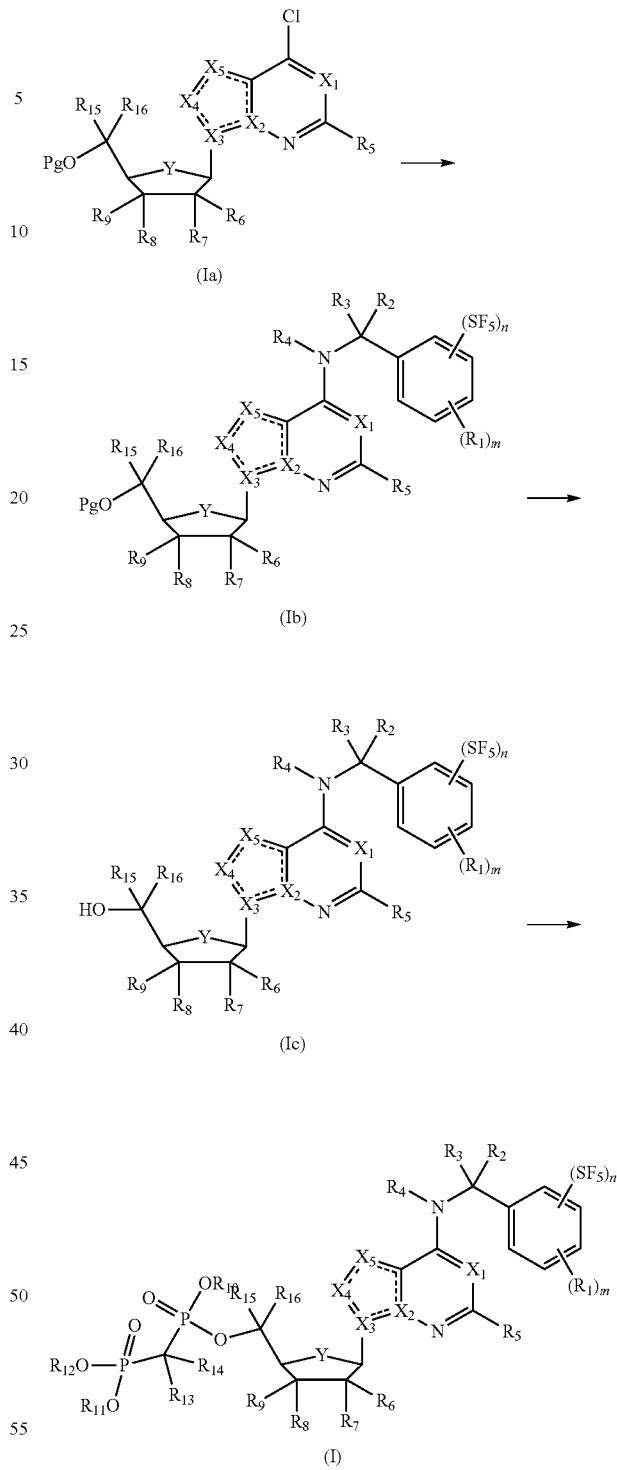

wherein, Pg is a hydroxy protecting group selected from the group consisting of an alkanoyl or silicane protecting group; $X_1$, $X_2$, $X_3$, $X_4$, $X_5$, Y, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, m and n are defined as in claim 1.

7. A pharmaceutical composition comprising a compound according to claim 1, or a stereoisomer or pharmaceutically-acceptable salt thereof, and a pharmaceutically acceptable carrier.

8. A compound having formula (IIIa1) or formula (IIIa2):

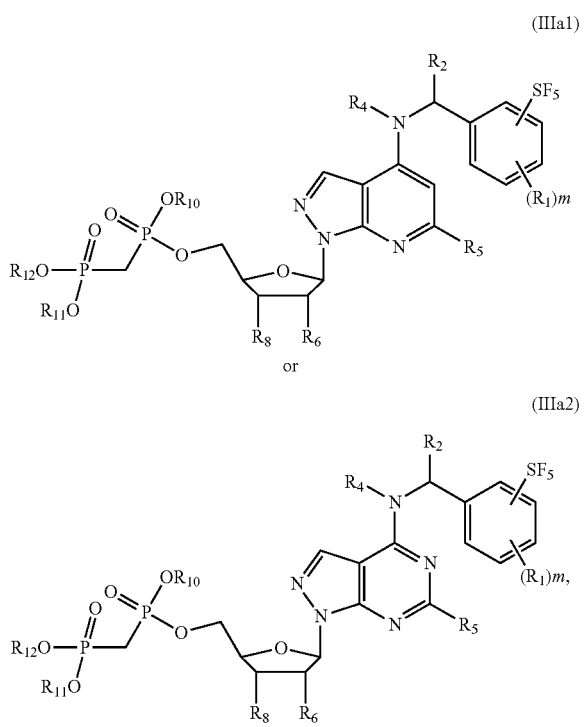

wherein, each $R_1$ is independently selected from the group consisting of hydrogen, deuterium, F, Cl, cyano, methyl, ethyl, n-propyl, isopropyl, difluoromethyl, trifluoromethyl, dideuterio methyl, trideuteriomethyl, $C_{3-6}$ cycloalkyl and 3-6 membered heterocyclyl;

each $R_2$ is independently selected from the group consisting of hydrogen, deuterium, F, Cl, cyano, methyl, ethyl, n-propyl, isopropyl, allyl, ethynyl, cyclopropyl and hydroxymethyl;

each $R_4$ is independently selected from the group consisting of hydrogen, deuterium, methyl, ethyl, n-propyl, isopropyl, $C_{2-4}$ alkenyl and $C_{3-6}$ cycloalkyl;

each $R_5$ is independently selected from the group consisting of hydrogen, deuterium, F, Cl, cyano, azido, methyl, ethyl, n-propyl, isopropyl, $C_{2-6}$ alkenyl, $C_{2-6}$ alkynyl and $C_{3-6}$ cycloalkyl;

each $R_6$ is independently selected from the group consisting of hydrogen, deuterium, halogen, methyl, ethyl, n-propyl, isopropyl and hydroxy;

each R& is independently selected from the group consisting of hydrogen, deuterium, halogen, methyl, ethyl, n-propyl, isopropyl and hydroxy;

$R_{10}$, $R_{11}$ and $R_{12}$ are each independently selected from the group consisting of hydrogen, deuterium, methyl, ethyl, n-propyl and isopropyl; and each m is independently 0, 1, 2 or 3; or a stereoisomer or pharmaceutically-acceptable salt thereof.

* * * * *